United States Patent
Fan et al.

(10) Patent No.: US 10,464,934 B2
(45) Date of Patent: *Nov. 5, 2019

(54) SUBSTITUTED TETRAHYDROPYRANS AS CCR2 MODULATORS

(71) Applicant: CHEMOCENTRYX, INC., Mountain View, CA (US)

(72) Inventors: Junfa Fan, Foster City, CA (US); Jaroslaw Kalisiak, Mountain View, CA (US); Rebecca M. Lui, Santa Clara, CA (US); Venkat Reddy Mali, Cupertino, CA (US); Jeffrey P. McMahon, San Francisco, CA (US); Jay P. Powers, Pacifica, CA (US); Hiroko Tanaka, Mountain View, CA (US); Yibin Zeng, Foster City, CA (US); Penglie Zhang, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/692,811

(22) Filed: Aug. 31, 2017

(65) Prior Publication Data

US 2018/0086756 A1 Mar. 29, 2018

Related U.S. Application Data

(63) Continuation of application No. 15/158,713, filed on May 19, 2016, now Pat. No. 9,783,540.

(60) Provisional application No. 62/164,957, filed on May 21, 2015.

(51) Int. Cl.
| | |
|---|---|
| *C07D 309/04* | (2006.01) |
| *C07D 471/04* | (2006.01) |
| *A61K 31/4545* | (2006.01) |
| *C07D 405/04* | (2006.01) |
| *A61K 31/453* | (2006.01) |
| *A61K 31/496* | (2006.01) |
| *C07D 413/14* | (2006.01) |
| *A61K 31/536* | (2006.01) |
| *C07D 405/14* | (2006.01) |
| *A61K 31/4725* | (2006.01) |
| *A61P 35/00* | (2006.01) |
| *A61P 37/00* | (2006.01) |
| *A61K 45/06* | (2006.01) |

(52) U.S. Cl.
CPC .......... *C07D 471/04* (2013.01); *A61K 31/453* (2013.01); *A61K 31/4545* (2013.01); *A61K 31/4725* (2013.01); *A61K 31/496* (2013.01); *A61K 31/536* (2013.01); *A61K 45/06* (2013.01); *A61P 35/00* (2018.01); *A61P 37/00* (2018.01); *C07D 405/04* (2013.01); *C07D 405/14* (2013.01); *C07D 413/14* (2013.01)

(58) Field of Classification Search
CPC .................................................. C07D 309/24
USPC .......................................................... 549/425
See application file for complete search history.

(56) References Cited

U.S. PATENT DOCUMENTS

| | | | |
|---|---|---|---|
| 6,949,546 | B2 | 9/2005 | Ko et al. |
| 8,629,133 | B2 | 1/2014 | Sugimoto |
| 9,783,540 | B2 | 10/2017 | Fan et al. |
| 2006/0030582 | A1 | 2/2006 | DeMartino et al. |
| 2010/0144695 | A1 | 6/2010 | Zhang et al. |
| 2012/0004252 | A1 | 1/2012 | Ebel et al. |
| 2012/0040960 | A1 | 2/2012 | Zhang et al. |

FOREIGN PATENT DOCUMENTS

| | | |
|---|---|---|
| WO | 02/13824 A1 | 2/2002 |
| WO | 03/092586 A2 | 11/2003 |
| WO | 03/093231 A2 | 11/2003 |
| WO | 03/093266 A1 | 11/2003 |
| WO | 2004/041777 A2 | 5/2004 |
| WO | 2004/076411 A2 | 9/2004 |
| WO | 2004/082682 A1 | 9/2004 |
| WO | 2004/092124 A2 | 10/2004 |
| WO | 2004/094371 A2 | 11/2004 |
| WO | 2004/110376 A2 | 12/2004 |
| WO | 2005/044264 A1 | 5/2005 |
| WO | 2005/044795 A1 | 5/2005 |

(Continued)

OTHER PUBLICATIONS

International Search Report and Written Opinion corresponding to PCT/US2016/033210 dated Aug. 16, 2016; 8 pages.

(Continued)

*Primary Examiner* — Douglas M Willis

(74) *Attorney, Agent, or Firm* — Mintz Levin Cohn Ferris Glovsky and Popeo PC

(57) ABSTRACT

Compounds are provided that are modulators of the CCR2 receptor. The compounds have the general formula (I):

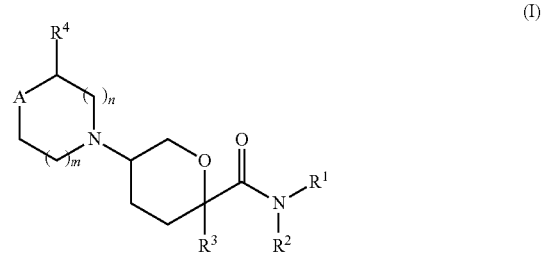

and are useful in pharmaceutical compositions, methods for the treatment of diseases and disorders involving the pathologic activation of CCR2 receptors.

13 Claims, 26 Drawing Sheets

(56) References Cited

FOREIGN PATENT DOCUMENTS

| WO | 2005/067502 A2 | 7/2005 |
| WO | 2005/080371 A1 | 9/2005 |
| WO | 2005/115392 A2 | 12/2005 |
| WO | 2006/073592 A2 | 7/2006 |
| WO | 2006/074265 A2 | 7/2006 |
| WO | 2010/121011 A1 | 10/2010 |
| WO | 2011/100227 A1 | 8/2011 |
| WO | 2011/159852 A1 | 12/2011 |

OTHER PUBLICATIONS

International Preliminary Report on Patentability corresponding to PCT/US2016/033210 dated Nov. 21, 2017; 6 pages.

Butora, Gabor et al., "3-Amino-1-alkyl-cyclopentane carboxamides as small molecule antagonists of the human and murine CC chemokine receptor 2," *Bioorganic & Medicinal Chemistry Letters* (Apr. 16, 2007); 17:3636-3641.

Carter, Percy H. et al., "Advances in the Discovery of CC Chemokine Receptor 2 Antagonists," *Annual Reports in Medicinal Chemistry* (2007); 42:211-227 [ISSN 0065-7743; DOI 10.1016/S0065-7743(07)42014-0].

Cherney, Robert J. et al., "Discovery of Disubstituted Cyclohexanes as New Class of CC Chemokine Receptor 2 Antagonists," *J. Med. Chem.* (published on Web Jan. 31, 2008); 51(4):721-724.

De Zeeuw, D. et al., Abstract Only: "The effect of CCR2 inhibitor CCX140-B on residual albuminuria in patients with type 2 diabetes and nephropathy: a randomized trial," *Lancet Diabetes Endocrinol* (Sep. 2015; Epub Aug. 9, 2015); 3(9):687-696.

Gao, Zhongli et al., "Unraveling the Chemistry of Chemokine Receptor Ligands," *Chem. Rev.* (2003; rec'd Nov. 26, 2002); 103:3733-3752.

Gong, Jiang-Hong et al., "An Antagonist of Monocyte Chemoattractant Protein 1 (MCP-1) Inhibits Arthritis in the MRL-/pr Mouse Model," *J. Exp. Med.* (Jul. 7, 1997); 186(1):131-137.

Hackam, Daniel G. et al., "Translation of Research Evidence from Animals to Humans," *JAMA* (Oct. 11, 2006); 296(14):1731-1732.

Jordan, V.Craig, "Tamoxifen: A Most Unlikely Pioneering Medicine," *Nature Reviews: Drug Discovery* (Mar. 2003); 2:205-213.

Karihaloo, Anil et al., "Macrophages Promote Cyst Growth in Polycystic Kidney Disease," *J Am Soc Nephrol* (Oct. 2011; accepted May 12, 2011); 22(10):1809-1814.

Kitagawa, Kiyoki et al., "Blockade of CCR2 Ameliorates Progressive Fibrosis in Kidney," *American Journal of Pathology* (Jul. 2004; accepted Mar. 30, 2004); 165(1):237-245.

Kothandaraman, Shankaran et al., "Design, synthesis, and structure-activity relationship of novel CCR2 antagonists," *Bioorganic & Medicinal Chemistry Letters* (2009; accepted Dec. 10, 2008); 19:1830-1834.

Lim, Jee Woong et al., "Synthesis and biological evaluation of 3-aminopyrrolidine derivatives as CC chemokine receptor 2 antagonsits," *Bioorganic & Medicinal Chemistry Letters* (2010; accepted Feb. 17, 2010); 20:2099-2102.

Moree, Wilna J. et al., "Potent antagonists of the CCR2b receptor. Part 3: SAR of the (R)-3-aminopyrrolidine series," *Bioorganic & Medicinal Chemistry Letters* (2008; accepted Feb. 7, 2008); 18:1869-1873.

Pasternak, Alexander et al., "Discovery of a Potent and Orally Bioavailable CCR2 and CCR5 Dual Antagonist," *ACS Med. Chem. Lett.* (2010; accepted Dec. 14, 2009); 1:14-18.

Pasternak, Alexander et al., "Potent heteroarylpiperidine and carboxyphenylpiperidine 1-alkyl-cyclopentane carboxamide CCR2 antagonists," *Bioorganic & Medicinal Chemistry Letters* (2008; accepted Dec. 11, 2007); 18:994-998.

Pasternak, Alexander et al., "Conformational studies of 3-amino-1-alkyl-cyclopentane carboxamide CCR2 antagonists leading to new spirocyclic antagonists," *Bioorganic & Medicinal Chemistry Letters* (2009; accepted Jan. 3, 2008); 18:1374-1377.

Press Release: ChemoCentryx's CCR2 Inhibitor CCX872 Shown to Reduce Liver Fibrosis in NASH Models, (Oct. 18, 2016); 4 pages.

PUBCHEM—'124' Create Date: Aug. 9, 2005; Date accessed Jul. 13, 2016; p. 3; compound; 13 pages.

Sanford, Dominic et al., "Inflammatory Monocyte Mobilization Decreases Patient Survival in Pancreatic Cancer: A Role for Targeting the CCL2/CCR2 Anxis," *Clin Cancer Res* (Jul. 1, 2013); 19(13):3404-3414.

Trujillo, John I. et al., "Design and synthesis of novel CCR2 antagonists: Investigation of non-aryl/heteroaryl binding motifs," *Bioorganic & Medicinal Chemistry Letters* (2011; accepted Jan. 13, 2011); doi:10.1016/j.bmcl.2011.01.052.

Ueno, Takayuki et al., "Significance of Macrophage Chemoattractant Protein-1 in Macrophage Recruitment, Angiogenesis, and Survival in Human Breast Cancer," *Clinical Cancer Research* (Aug. 2000; accepted May 22, 2000); 6:3282-3289.

Vestergaard, Christian et al., "Expression of CCR2 on Monocytes and Macrophages in Chronically Inflamed Skin in Atopic Dermatitis and Psoriasis," *Acta derm Venereol* (2004; accepted Apr. 12, 2004); 84:353-358.

Vippagunta, Sudha R. et al., "Crystalline solids," *Advanced Drug Delivery Reviews* (2001; accepted Dec. 21, 2000); 48:3-26.

Xue, Chu-Biao et al., "Discovery of INCB8761/PF-4136309, a Potent, Selective, and Orally Bioavailable CCR2 Antagonist," *ACS Med. Chem. Lett.* (2011; published Oct. 5, 2011); 2:913-918.

Xue, Chu-Biao et al., "Discovery of INCB3284, a Potent, Selective, and Orally Bioavailable hCCR2 Antagonist," *ACS Med. Chem. Lett.* (2011; published Mar. 31, 2011); 2:450-454.

Kang, Young Sun et al., "CCR2 antagonism improves insulin resistance, lipid metabolism, and diabetic nepropathy in type 2 diabetic mice," *Kidney International* (published online Aug. 4, 2010); 78:883-894.

Miura, Kouichi et al., "Hepatic recruitment of macrophages promotes nonalcoholic steatohepatitis through CCR2," *Am J Physiol Gastrointest Liver Physiol* (Mar. 22, 2012); 302:G1310-G1321.

Extended European Search Report corresponding to EP 16797279.3 (PCT/US2016033210) dated Oct. 26, 2018; 8 pages.

FIG. 1A
| ID | Structure | Potency | ID | Structure | Potency |
|---|---|---|---|---|---|
| 1 | 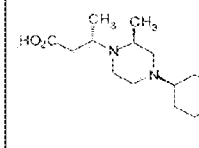 | +++ | 6 | 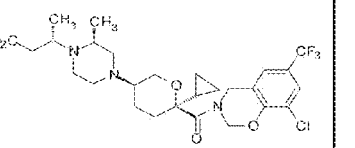 | +++ |
| 2 | 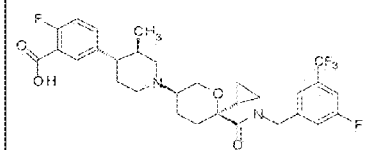 | +++ | 7 | 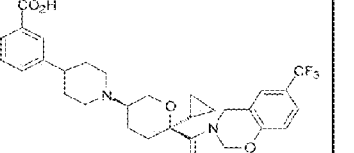 | +++ |
| 3 | 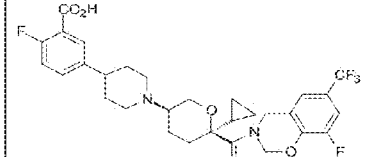 | +++ | 8 | 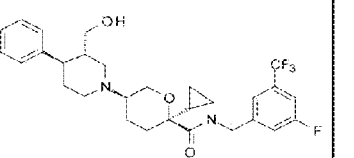 | +++ |
| 4 | 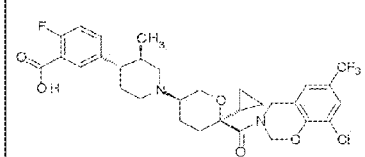 | +++ | 9 | 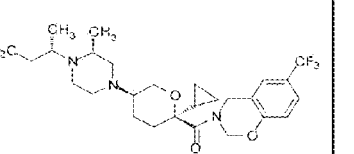 | +++ |
| 5 | 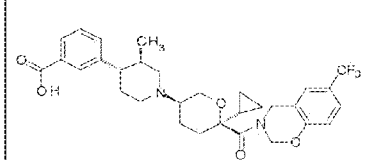 | +++ | 10 | 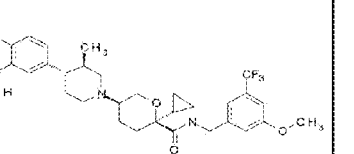 | +++ |

| | | |
|---|---|---|
| 11 | | +++ |
| 12 | | +++ |
| 13 | | +++ |
| 14 | | +++ |
| 15 | | +++ |
| 16 | | +++ |
| 17 | | +++ |
| 18 | | +++ |
| 19 | | +++ |
| 20 | | +++ |

FIG. 1D
| | | | | | |
|---|---|---|---|---|---|
| 31 | 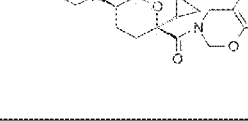 | +++ | 36 | 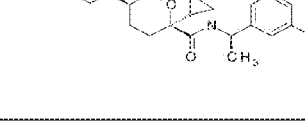 | +++ |
| 32 | 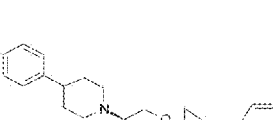 | +++ | 37 | 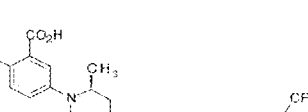 | +++ |
| 33 | 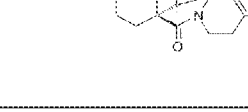 | +++ | 38 | 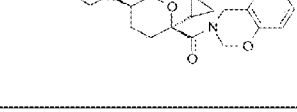 | +++ |
| 34 | 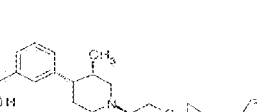 | +++ | 39 | 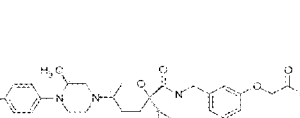 | +++ |
| 35 | 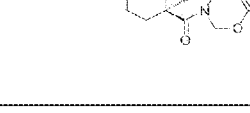 | +++ | 40 |  | +++ |

FIG. 1E

FIG. 1F
| | | | | | |
|---|---|---|---|---|---|
| 51 | 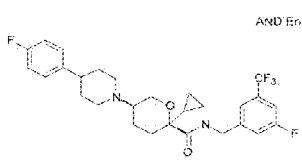 | +++ | 56 | 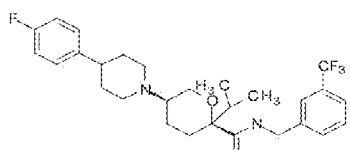 | +++ |
| 52 | 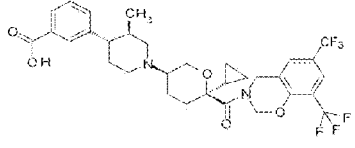 | +++ | 57 | 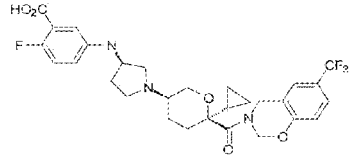 | +++ |
| 53 | 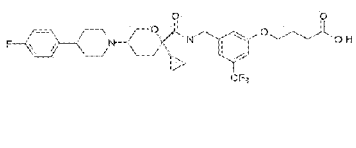 | +++ | 58 | 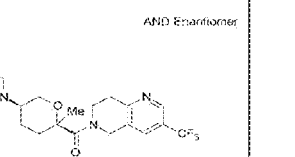 | +++ |
| 54 | 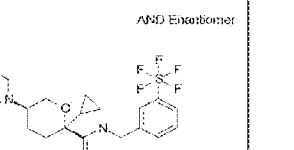 | +++ | 59 | 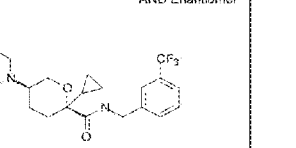 | +++ |
| 55 | 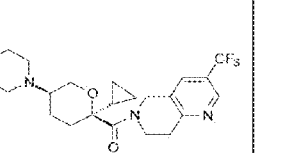 | +++ | 60 | 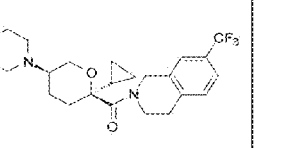 | +++ |

FIG. 1G

| | | | | |
|---|---|---|---|---|
| 61 | | +++ | 66 | +++ |
| 62 | | +++ | 67 | +++ |
| 63 | | +++ | 68 | +++ |
| 64 | | +++ | 69 | +++ |
| 65 | | +++ | 70 | +++ |

FIG. 1J

FIG. 1K
| | | | | | |
|---|---|---|---|---|---|
| 101 | 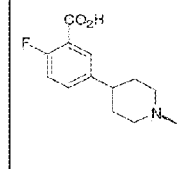 | +++ | 106 | 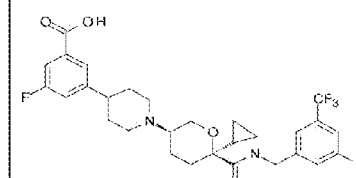 | +++ |
| 102 | 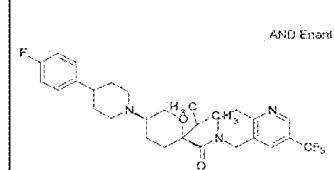 | +++ | 107 | 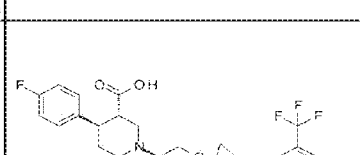 | +++ |
| 103 | 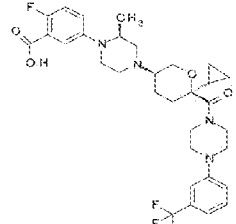 | +++ | 108 | 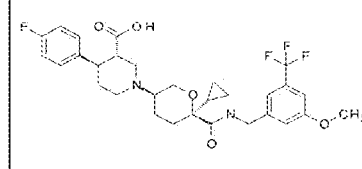 | +++ |
| 104 | 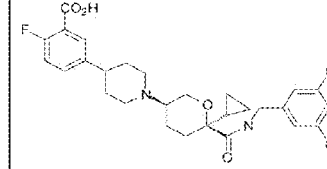 | +++ | 109 | 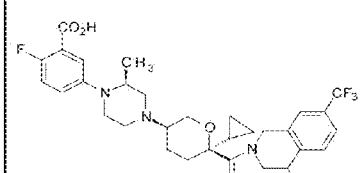 | +++ |
| 105 | 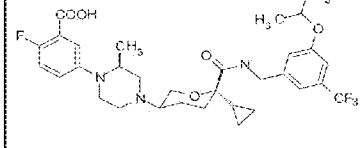 | +++ | 110 |  | +++ |

| | | | | | |
|---|---|---|---|---|---|
| 151 | | +++ | 156 | | +++ |
| 152 | | +++ | 157 | | +++ |
| 153 | | +++ | 158 | | +++ |
| 154 | | +++ | 159 | | +++ |
| 155 | | +++ | 160 | | +++ |

FIG. 1Q

FIG. 1R
| | | | | | |
|---|---|---|---|---|---|
| 171 | 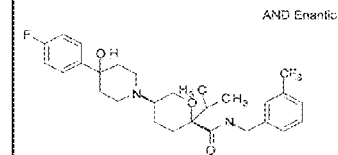 | +++ | 176 | 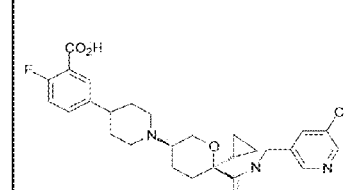 | +++ |
| 172 | 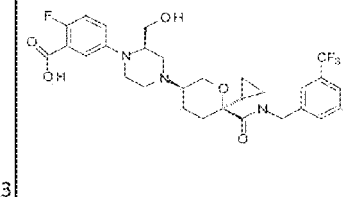 | +++ | 177 | 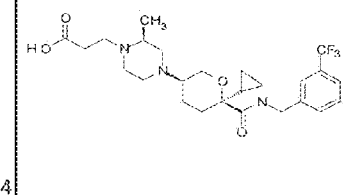 | +++ |
| 173 | 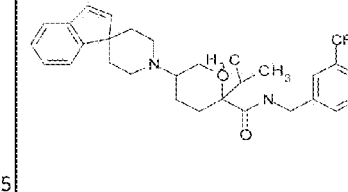 | +++ | 178 | 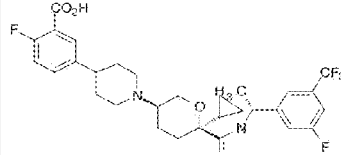 | ++ |
| 174 | 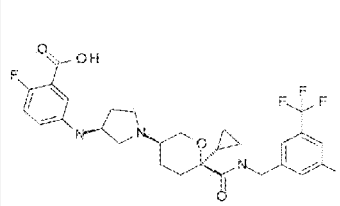 | +++ | 179 | 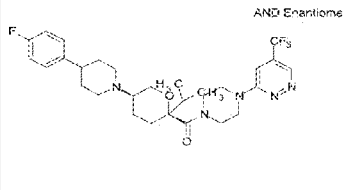 | ++ |
| 175 | 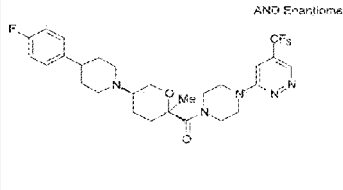 | +++ | 180 | 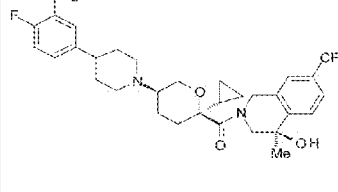 | ++ |

FIG. 1S
| | | | | | |
|---|---|---|---|---|---|
| | 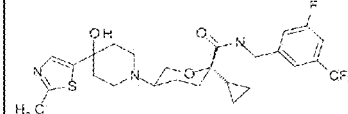 | | |  | |
| 181 | | ++ | 186 | | ++ |
| | 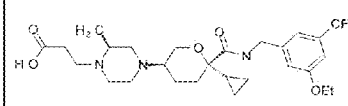 | | | 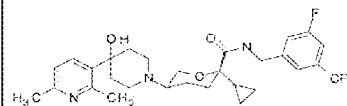 | |
| 182 | | ++ | 187 | | ++ |
| | 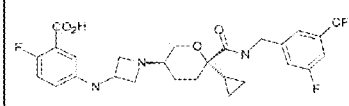 | | | 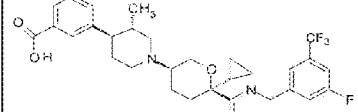 | |
| 183 | | ++ | 188 | | ++ |
| | 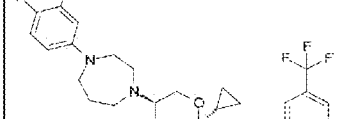 | | | 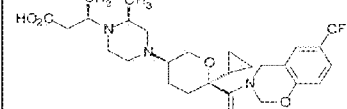 | |
| 184 | | ++ | 189 | | ++ |
| | 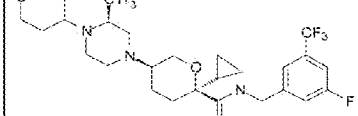 | | | 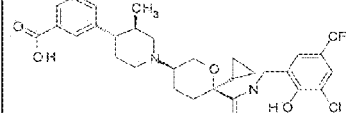 | |
| 185 | | ++ | 190 | | ++ |

FIG. 1T
| | | | | | |
|---|---|---|---|---|---|
| 191 | 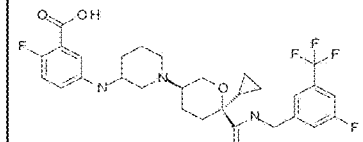 | ++ | 196 | 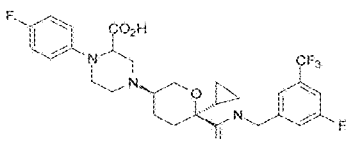 | ++ |
| 192 | 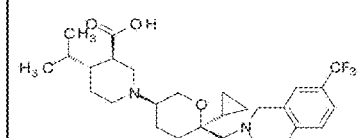 | ++ | 197 | 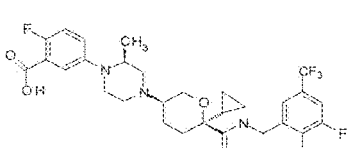 | ++ |
| 193 | 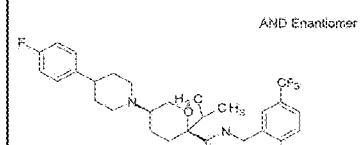 AND Enantiomer | ++ | 198 | 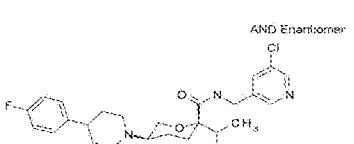 AND Enantiomer | ++ |
| 194 | 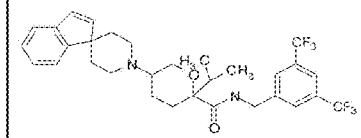 | ++ | 199 | 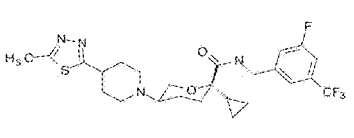 | ++ |
| 195 | 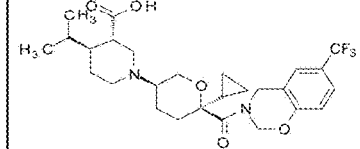 | ++ | 200 | 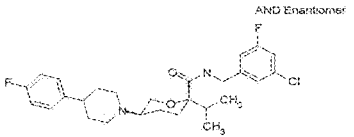 AND Enantiomer | ++ |

FIG. IV
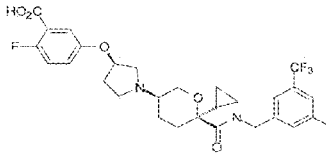

FIG. 2
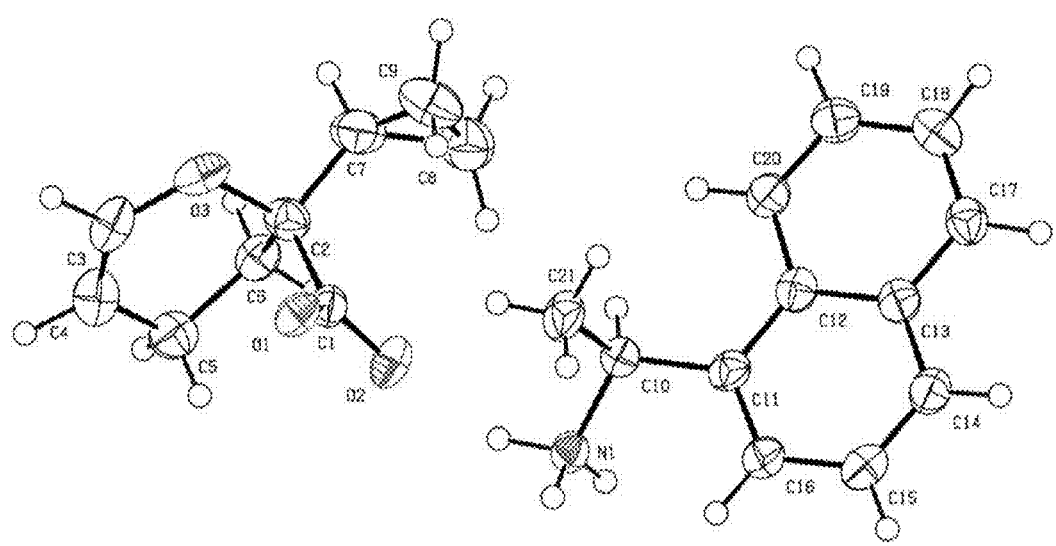
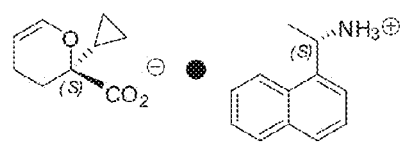

SUBSTITUTED TETRAHYDROPYRANS AS CCR2 MODULATORS

CROSS-REFERENCES TO RELATED APPLICATIONS

This application is a continuation of U.S. patent application Ser. No. 15/158,713 filed May 19, 2016, which application claims the benefit of priority under 35 U.S.C. § 119(e) to U.S. Provisional Application Ser. No. 62/164,957, filed May 21, 2015, each of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Chemokines, also known as chemotactic cytokines, are a group of small molecular-weight proteins that are released by a wide variety of cells and have a variety of biological activities. Chemokines attract various types of cells of the immune system, such as macrophages, T cells, eosinophils, basophils and neutrophils, and cause them to migrate from the blood to various lymphoid and none-lymphoid tissues. They mediate infiltration of inflammatory cells to sites of inflammation, and are responsible for the initiation and perpetuation of many inflammation diseases (reviewed in Schall, *Cytokine*, 3:165-183 (1991), Schall et al., *Curr. Opin. Immunol.*, 6:865-873 (1994)).

In addition to stimulating chemotaxis, chemokines can induce other changes in responsive cells, including changes in cell shape, granule exocytosis, integrin up-regulation, formation of bioactive lipids (e.g., leukotrienes), respiratory burst associated with leukocyte activation, cell proliferation, resistance to induction of apoptosis and angiogenesis. Thus, chemokines are early triggers of the inflammatory response, causing inflammatory mediator release, chemotaxis and extravasation to sites of infection or inflammation. They are also stimulators of a multitude of cellular processes that bear important physiological functions as well as pathological consequences.

Chemokines exert their effects by activating chemokine receptors expressed by responsive cells. Chemokine receptors are a class of G-protein coupled receptors, also known as seven-transmembrane receptors, found on the surface of a wide variety of cell types such as leukocytes, endothelial cells, smooth muscle cells and tumor cells.

Chemokines and chemokine receptors are expressed by intrinsic renal cells and infiltrating cells during renal inflammation (Segerer et al., *J. Am. Soc. Nephrol.*, 11:152-76 (2000); Morii et al., *J. Diabetes Complications*, 17:11-5 (2003); Lloyd et al. *J. Exp. Med.*, 185:1371-80 (1997); Gonzalez-Cuadrado et al. *Clin. Exp. Immuno.* 106:518-22 (1996); Eddy & Giachelli, *Kidney Int.*, 47:1546-57 (1995); Diamond et al., *Am. J. Physiol.*, 266:F926-33 (1994)). In humans, CCR2 and ligand MCP-1 are among the proteins expressed in renal fibrosis, and are correlated with the extent of macrophage infiltration into the interstitium (Yang et al., Zhonghua Yi Xue Za Zhi, 81:73-7 (2001); Stephan et al., *J. Urol.*, 167:1497-502 (2002); Amann et al., *Diabetes Care*, 26:2421-5 (2003); Dai et al., *Chin. Med. J.* (Engl), 114: 864-8 (2001)). In animal models of renal fibrosis, blockade of CCR2 or MCP-1 leads to a marked reduction in severity of renal inflammation (Kitagawa et al., *Am. J. Pathol.*, 165:237-46 (2004); Wada et al., *Am. J. Pathol.*, 165:237-46 (2004); Shimizu et al., *J. Am. Soc. Nephrol.*, 14:1496-505 (2003)).

Additionally CCR2 plays a role in the development of polycystic kidney disease (PKD). The pathology of ADPKD is characterized by renal cysts that arise from tubular epithelial cells and enlarge continuously over the patient's lifetime. The expanding cysts are accompanied by the presence of a large number of infiltrating macrophages which are recruited to the kidney in response to injury. Thus, inhibition of immune recruitment to the kidney constitutes a therapeutic strategy for PKD (*J Am Soc Nephrol.* 2011 October; 22(10): 1809-14.)

Rheumatoid arthritis is a chronic disease of the joints characterized by synovial inflammation that leads to the destruction of cartilage and bone. Although the underlying causes of the disease are unknown, it is believed that macrophages and Th-1 type T cells play a key role in the initiation and perpetuation of the chronic inflammatory process (Vervoordeldonk et al., *Curr. Rheumatol. Rep.*, 4:208-17 (2002)).

MCP-1 is among the several chemokines, including MIP-1α and IL-8, identified in rheumatoid synovium (Villiger et al., *J. Immunol.*, 149:722-7 (1992); Scaife et al., Rheumatology (Oxford), 43:1346-52 (2004); Shadidi et al., *Scand. J. Immunol.*, 57:192-8 (2003); Taylor et al., *Arthritis Rheum.*, 43:38-47 (2000); Tucci et al., *Biomed Sci. Instrum.*, 34:169-74 (1997)). Chemokine receptors CCR1, CCR2. CCR3 and CCR5 are up-regulated in the joints from arthritic mice (Plater-Zyberk et al., *Immunol. Lett.*, 57:117-20 (1997). Blockade of MCP-1 activity using a CCR2 antagonist or an antibody against MCP-1 have been shown efficacious in reducing joint inflammation in experimental models of rheumatoid arthritis (Gong et al., *J. Exp. Med.*, 186:131-7 (1997); Ogata et al., *J. Pathol.*, 182:106-14 (1997)).

Chemokine receptor-mediated infiltration of macrophages in the fat tissues may also contribute to the complications arising from obesity, a condition resulting from excessive storage of fat in the body. Obesity predisposes the affected individuals to many disorders, such as non-insulin-dependent diabetes, hypertension, stroke, and coronary artery disease. In obesity, adipose tissues have altered metabolic and endocrine functions that lead to an increased release of fatty acids, hormones, and pro-inflammatory molecules. Adipose tissue macrophages are believed to be a key source of pro-inflammatory cytokines including TNF-alpha, iNOS and IL-6 (Weisberg et al., *J. Clin. Invest.*, 112:1796-808 (2003)). Recruitment of macrophages to the adipose tissue is likely mediated by MCP-1 produced by adipocytes (Christiansen T, et al., *Int J Obes* (Lond). 2005 January; 29(1): 146-50; Sartipy et al., *Proc. Natl. Acad Sci. U.S.A.*, 100: 7265-70 (2003)).

Elevated MCP-1 may induce adipocyte differentiation and insulin resistance, and contribute to pathologies associated with hyper-insulinemia and obesity. MCP-1 is over-expressed in plasma in obese mice compared to lean controls and white adipose is a major source. MCP-1 has also been shown to accelerate wound healing, and has a direct angiogenic effect on epithelial cells, and may play a direct role in the remodeling of adipose tissue in obesity. (Sartipy P, Loskutoff D J., *Proc. Natl. Acad. Sci. U.S.A.*, 100:7265 (2003)).

MCP-1 plasma levels are substantially increased in Diet Induce Obesity (DIO) mice, and a strong correlation between plasma MCP-1 levels and body weight has been identified. Furthermore, elevation of MCP-1 induced by high fat diet causes changes in the CD11b positive monocyte population in DIO mice. (Takahashi K, et al., *J. Biol. Chem.*, 46654 (2003)).

Furthermore, chronic inflammation in fat is thought to play a crucial role in the development of obesity-related insulin resistance (Xu H. et al., *J Clin Invest.* 2003 December; 112(12):1821-30). It has been proposed that obesity related insulin resistance is, at least in part, a chronic inflammatory disease initiated in adipose tissue. Many inflammation and macrophage specific genes are dramatically upregulated in white adipose tissue in mouse models of genetic and high fat diet-induced obesity (DIO), and this upregulation precedes a dramatic increase in circulating insulin.

Increased expression levels of monocyte CCR2 and monocyte chemoattractant protein-1 in patients with diabetes mellitus (*Biochemical and Biophysical Research Communications*, 344(3):780-5 (2006)) were found in a study involving diabetic patients. Serum MCP-1 concentrations and surface expression of CCR2 on monocytes in diabetic patients were significantly higher than in non-diabetics, and the serum MCP-1 levels correlated with HbA1c, triglycerides, BMI, hs-CRP. Surface expression levels of CD36 and CD68 on monocytes were significantly increased in diabetic patients and more unregulated by MCP-1 in diabetics, augmenting uptake of ox-LDL, and hence potentially foam cell transformation. Elevated serum MCP-1 and increased monocyte CCR2. CD36. CD68 expression correlated with poor blood glucose control and potentially correlate with increased vessel wall monocyte recruitment.

MCP-1 is a potential player in negative cross talk between adipose tissue and skeletal muscle (Bianco J J, et al., *Endocrinology*, 2458 (2006)). MCP-1 can significantly reduce insulin-stimulated glucose uptake, and is a prominent inducer of insulin resistance in human skeletal muscle cell. Adipose tissue is a major secretory and endocrine active organ producing bioactive proteins regulating energy metabolism and insulin sensitivity.

CCR2 modulates inflammatory and metabolic effects of high-fat feeding (Weisberg S P, et al., *J. Clin. Invest.*, 115 (2006)). Genetic deficiency in CCR2 reduced food intake and attenuated the development of obesity in mice fed a high fat diet. In obese mice matched for adiposity, CCR2 deficiency reduced macrophage content and inflammatory profile of adipose tissue, increased adiponectin expression, and improved glucose homeostatis and insulin sensitivity. In lean animals, no effect of CCR2 genotype on metabolic trait was found. In high-fat diet mice, CCR2 genotype modulated feeding, the development of obesity and adipose tissue inflammation. Once established, short term antagonism was shown to attenuate macrophage accumulation in adipose tissue and insulin resistance.

Chemokine and chemokine receptors are the key regulators of immune cell trafficking. MCP-1 is a potent chemoattractant of monocytes and T cells; its expression is induced under inflammatory conditions including proinflammatory cytokine stimulations and hypoxia. The interaction between MCP-1 and CCR2 mediates migration of monocytes, macrophage as well as activated T cells and play a key role in the pathogenesis of many inflammatory diseases. Inhibition of CCR2 functions using small molecule antagonists described in this invention represents a new approach for the treatments of inflammatory disorders.

Psoriasis is a chronic inflammatory disease characterized by hyperproliferation of keratinocytes and pronounced leukocyte infiltration. It is known that keratinocytes from psoriasis lesion express abundant CCR2 ligand MCP-1, particularly when stimulated by proinflammatory cytokines such as TNF-α (Vestergaard et al., *Acta. Derm. Venereol.*, 84(5):353-8 (2004); Gillitzer et al., *J. Invest. Dermatol.*, 101(2):127-31 (1993); Deleuran et al., *J. Dermatol. Sci.*, 13(3):228-36 (1996)). Since MCP-1 can attract migration of both macrophages and dendritic cells expressing CCR2 to the skin, this receptor and ligand pair is believed to be important in regulating the interaction between proliferating keratinocytes and dermal macrophage during the development of psoriasis. A small molecule antagonist may thus be useful in the treatment of psoriasis.

In addition to inflammatory diseases, chemokines and chemokine receptors have also been implicated in cancers (Broek et al., *Br. J. Cancer.* 88(6):855-62 (2003)). Tumor cells stimulate the formation of stroma that secretes various mediators pivotal for tumor growth, including growth factors, cytokines, and proteases. It is known that the level of MCP-1 is associated significantly with tumor-associated macrophage accumulation, and prognostic analysis reveals that high expression of MCP-1 is a significant indicator of early relapse in breast cancer (Ueno et al., *Clin. Cancer Res.*, 6(8):3282-9 (2001)). A small molecule antagonist of a chemokine may thus be able to reduce the release of growth-stimulating cytokines by blocking accumulation of macrophages at sites of tumor formation.

CCR2 and its ligand CCL2 also play a major role in conditioning the tumor microenvironment, and regulating the influx of both beneficial and deleterious immune cell populations to the tumor. As such recent clinical and preclinical literature has demonstrated a role for CCR2 in a variety of solid tumors either through up-regulation of its expression in transformed cells or in enhanced chemotaxis of inflammatory monocytes into the tumour that terminally differentiates into myeloid-derived suppressor cells (MDSCs) or tumour associated macrophages (TAMs). MDSCs/TAMs are thought to promote tumorgenesis through the following mechanisms: (1) contribute to the general immunosuppressive microenvironment, thereby promoting tumour growth, that abolish the cytotoxic functionality of infiltrating cytotoxic T cells (Mitchem et al, *Cancer Res* 73(3): 1128-1141), (2) enhance angiogenesis through secretion of vascular endothelial growth factor (VEGF) and other growth factors (Murdoch et al, *Nat Rev Cancer* 8: 618-631), (3) prevent tumour senescence (Di Mitri et al. *AOP. Nature*, 2014), and (4) promote tumour metastases into distal organs (Qian et al. *Nature* 475: 222-227). Thus, a small molecule antagonist can be useful in limiting tumorgenesis, enhancing tumour specific immune activity, and tumour metastases.

Provided herein are compounds that are CCR2 modulators and address some of the shortcomings identified with earlier CCR2 modulators.

BRIEF SUMMARY OF THE INVENTION

In one aspect, the present invention provides compounds having the formula:

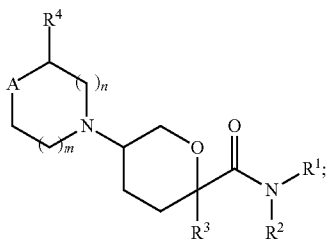

(I)

or a pharmaceutically acceptable salt, hydrate, stereoisomer or rotamers thereof; wherein the symbols $R^1$, $R^2$, $R^3$, $R^4$, A and the subscripts m and n have the meanings provided in the Detail Description of the Invention.

In addition to the compounds provided herein, the present invention further provides pharmaceutical compositions containing one or more of these compounds, as well as methods for the use of these compounds in therapeutic methods, primarily to treat diseases associated CCR2 signalling activity.

In yet another aspect, the present invention provides methods of diagnosing disease in an individual. In these methods, the compounds provided herein are administered in labeled form to a subject, followed by diagnostic imaging to determine the presence or absence of CCR2. In a related aspect, a method of diagnosing disease is carried out by contacting a tissue or blood sample with a labeled compound as provided herein and determining the presence, absence, or amount of CCR2 in the sample.

In still another aspect, the present invention provides a method for modulating chemokine function, comprising contacting a chemokine receptor with a therapeutically effective amount of a compound or composition according to the invention.

In still another aspect, the present invention provides a method for treating a chemokine-mediated condition or disease, comprising administering to a subject a safe and effective amount of a compound or composition according to the invention.

In one particular aspect, the present invention relates to a method of treating a CCR2-mediated condition or disease comprising administering to a subject a therapeutically effective amount of a compound or pharmaceutically acceptable salt of a compound of formula I. In certain embodiments, a CCR2-mediated condition or disease is atherosclerosis. In certain embodiments, a CCR2-mediated condition or disease is restenosis. In certain embodiments, a CCR2-mediated condition or disease is multiple sclerosis. In certain embodiments, a CCR2-mediated condition or disease is selected from the group consisting of inflammatory bowel disease, renal fibrosis, rheumatoid arthritis, obesity and noninsulin-dependent diabetes. In certain embodiments, a CCR2-mediated condition or disease is type 2 diabetes. In certain embodiments, a CCR2-mediated condition or disease is selected from the group consisting of chronic obstructive pulmonary disease, idiopathic pulmonary fibrosis and idiopathic pneumonia syndrome.

In addition to the compounds provided herein, the present invention further provides pharmaceutical compositions containing one or more of these compounds, as well as methods for the use of these compounds in therapeutic methods, primarily to treat diseases associated with chemokine signaling activity.

BRIEF DESCRIPTION OF THE DRAWINGS

FIG. 2 provide an ORTEP structure of a component portion of the compounds described herein and shows the stereochemistry of a quaternary center (shown as bearing a cyclopropyl group and identified as having 'S' chirality).

DETAILED DESCRIPTION OF THE INVENTION

I. Abbreviation and Definitions

Figure 1B:
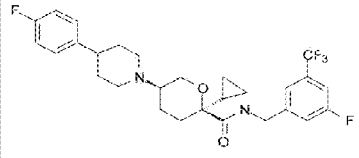
FIGS. 1A-1Y provide structures and activity for representative compounds of the present invention. The compounds were prepared as described generally below, as well as by methods provided in the Examples. Activity is provided as follows for the binding assay as described herein: +, 501 nM≤IC50<5000 nM; ++, 101 nM≤IC50<500 nM; and +++, 1 nM≤IC50≤100 nM.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom. For terms such as cycloalkylalkyl and heterocycloalkylalkyl, it is meant that a cycloalkyl or a heterocycloalkyl group is attached through an alkyl or alkylene linker to the remainder of the molecule. For example, cyclobutylmethyl—is a cyclobutyl ring that is attached to a methylene linker to the remainder of the molecule.

The term "alkylene" by itself or as part of another substituent means a divalent radical derived from an alkane, as exemplified by —$CH_2CH_2H_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl." by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen." by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group that is attached to the remainder of the molecule (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —$NO_2$ in a number ranging from zero to (2 m'+1), where m' is the total number of carbon atoms in such radical. R', R" and R''' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substitutent=O (e.g., —C(O)$CH_3$, —C(O)$CH_2CH_2$OR' and the like).

Similarly, substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR'C(O)$_2$R', —NR'—C(O)NR"R''', —NH—C(NH$_2$)=NH, —NR'C(NH$_2$)=NH, —NH—C(NH$_2$)—NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{3-6}$ cycloalkyl, $C_{2-4}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR"— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

For the compounds provided herein, a bond that is drawn from a substituent (typically an R group) to the center of an aromatic ring (e.g., benzene, pyridine, and the like) will be understood to refer to a bond providing a connection at any of the available vertices of the aromatic ring. In some embodiments, the depiction will also include connection at a ring which is fused to the aromatic ring. For example, a bond drawn to the center of the benzene portion of an indole, will indicate a bond to any available vertex of the six- or five-membered ring portions of the indole.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When compounds are provided herein with an identified stereochemistry (indicated as R or S, or with dashed or wedge bond designations), those compounds will be understood by one of skill in the art to be substantially free of other isomers (e.g., at least 80%, 90%, 95%, 98%, 99%, and up to 100% free of the other isomer).

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

II. General

The present invention is directed to compounds and salts thereof, compositions and methods useful in the modulation of chemokine receptor function, particularly CCR2 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR2 receptor. Accordingly, the compounds of the present invention are compounds which modulate at least one function or characteristic of mammalian CCR2, for example, a human CCR2 protein. The ability of a compound to modulate the function of CCR2, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

III. Compounds

In one aspect, the present invention provides compounds having the formula I:

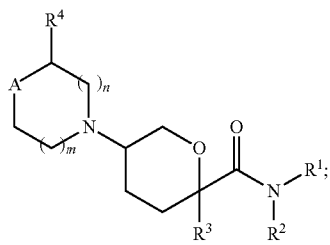

(I)

or a pharmaceutically acceptable salt, hydrate, stereoisomer or rotamer thereof; wherein A is $C(R^5)(R^6)$ or $N(R^5)$
the subscripts m and n are each independently integers of from 0 to 2, and m+n is ≤3;

$R^1$ is selected from the group consisting of aryl, aryl-$C_{1-4}$ alkyl, heteroaryl and heteroaryl-$C_{1-4}$ alkyl, wherein the heteroaryl portion has from 1-3 heteroatoms as ring members selected from N, O and S; and wherein said aryl and heteroaryl groups or portions are optionally substituted with from 1 to 5 $R^x$ substituents;

$R^2$ is selected from the group consisting of H, $C_{1-4}$ alkyl, $C_{3-8}$ cycloalkyl, $C_{3-8}$ cycloalkyl-$C_{1-4}$ alkyl, aryl, aryl-$C_{1-4}$ alkyl, heteroaryl and heteroaryl-$C_{1-4}$ alkyl, wherein the heteroaryl portion has from 1-3 heteroatoms as ring members selected from N, O and S; and wherein said aryl and heteroaryl groups or portions are optionally substituted with from 1 to 4 $R^x$ substituents;

or optionally, $R^1$ and $R^2$ are combined with the nitrogen atom to which each is attached to form a 6- to 11-membered monocyclic or fused bicyclic-heterocyclic or heteroaryl ring, wherein the —$NR^1R^2$ is optionally further substituted with from 1 to 4 $R^x$ substituents;

$R^3$ is selected from the group consisting of H, $C_{1-4}$ alkyl, $C_{3-8}$ cycloalkyl and $C_{3-8}$ cycloalkyl-$C_{1-4}$ alkyl, each of which is optionally substituted with from 1-3 $R^y$ substituents;

$R^4$ is selected from the group consisting of H, $C_{1-8}$ alkyl optionally substituted with 1 to 2 $R^y$, and —$CO_2H$;

$R^5$ is selected from the group consisting of $C_{1-8}$ alkyl, $C_{1-8}$ alkoxy, $C_{3-8}$ cycloalkyl, $C_{3-8}$ cycloalkyloxy, $C_{3-8}$ cycloalkyl-$C_{1-4}$ alkyl, $C_{1-8}$ alkylamino, di-$C_{1-8}$ alkylamino, aryl, aryloxy, arylamino, aryl-$C_{1-4}$ alkyl, heteroaryl, heteroaryloxy, heteroarylamino and heteroaryl-$C_{1-4}$ alkyl, each of which is optionally substituted with from 1 to 5 $R^z$ substituents;

$R^6$ is selected from the group consisting of H, F, OH, $C_{1-8}$ alkyl and $C_{1-8}$ alkoxy, wherein the $C_{1-8}$ alkyl and $C_{1-8}$ alkoxy groups are optionally substituted with from 1 to 3 $R^z$ substituents;

or optionally, $R^5$ and $R^6$ are joined to form a spirocyclic 5- or 6-membered cycloalkyl ring which is optionally unsaturated, and has a fused aryl group which is optionally substituted with from 1 to 4 $R^z$ substituents;

each $R^x$ is independently selected from the group consisting of
halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aC(O)NR^aR^b$, —$NR^aR^b$, —$OR^a$, —O—$X^1$—$OR^a$, —O—$X^1$—$NR^aR^b$, —O—$X^1$—$CO_2R^a$, —O—$X^1$—$CONR^aR^b$, —$X^1$—$OR^a$, —$X^1$—$NR^aR^b$, —$X^1$—$CO_2R^a$, —$X^1$—$CONR^aR^b$, —$SF_5$, —$S(O)_2NR^aR^b$, and 5- or 6-membered aryl or heteroaryl, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^c$ is independently selected from the group consisting of $C_{1-8}$ alkyl, $C_{1-8}$ haloalkyl and $C_{3-6}$ cycloalkyl; and optionally when two $R^x$ substituents are on adjacent atoms, are combined to form a fused five or six-membered carbocyclic ring, and wherein the aryl or heteroaryl groups are optionally substituted with 1-3 members selected from halogen, hydroxyl, $C_{1-4}$ alkyl, $C_{1-4}$ alkoxy, $C_{1-4}$ haloalkyl, and $C_{1-4}$ haloalkoxy;

each $R^y$ is independently selected from the group consisting of
halogen, —CN, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl and $C_{3-6}$ cycloalkyl;

each $R^z$ is independently selected from the group consisting of halogen, —CN, —R$^i$, —CO$_2$R$^g$, —CONR$^g$R$^h$, —C(O)R$^g$, —OC(O)NR$^g$R$^h$, —NR$^h$C(O)R$^g$, —NR$^h$C(O)$_2$R$^i$, —NR$^g$C(O)NR$^g$R$^h$, —NR$^g$R$^h$, —OR$^g$, —S(O)$_2$NR$^g$R$^h$, —X$^1$—R$^j$, —X$^1$—NR$^g$R$^h$, —X$^1$—CONR$^g$R$^h$, —X$^1$—NR$^h$C(O)R$^g$, —NHR$^j$, —NHCH$_2$R$^j$, and tetrazole; wherein each R$^g$ and R$^h$ is independently selected from hydrogen, C$_{1-8}$ alkyl, C$_{3-6}$ cycloalkyl and C$_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each R$^i$ is independently selected from the group consisting of C$_{1-8}$ alkyl, C$_{1-8}$ haloalkyl and C$_{3-6}$ cycloalkyl; and each R$^j$ is selected from the group consisting of C$_{3-6}$ cycloalkyl, pyrrolinyl, piperidinyl, morpholinyl, tetrahydrofuranyl, and tetrahydropyranyl.

It shall be understood that when R$^1$ and R$^2$ are combined with the nitrogen atom to which each is attached to form a 6- to 11-membered monocyclic or fused bicyclic-heterocyclic ring, the 6- to 11-membered monocyclic or fused bicyclic-heterocyclic ring encompasses monocyclic heterocyclic rings fused with an aryl or a heteroaryl ring.

In formula I, the substituent R$^3$ is, in one embodiment, selected from the group consisting of H, methyl, ethyl, propyl, isopropyl, buty, isobutyl, sec-butyl, cyclopropyl, cyclopropylmethyl, cyclobutyl and cyclobutylmethyl.

In the descriptions herein, one of skill in the art will understand that the wavy line intersecting a bond is meant to identify the point of attachment of a given substituent or group to the remainder of the molecule.

As noted above, the subscripts m and n are each integers selected from 0, 1 and 2, and m+n is ≤3. When the subscript is 0, one of skill in the are will understand that a cyclic structure with ring vertex A is intended, but that adjacent ring vertices on either side of the parentheses are joined by a bond. Accordingly, the present invention includes the structures wherein the ring having A as a vertex is meant to include:

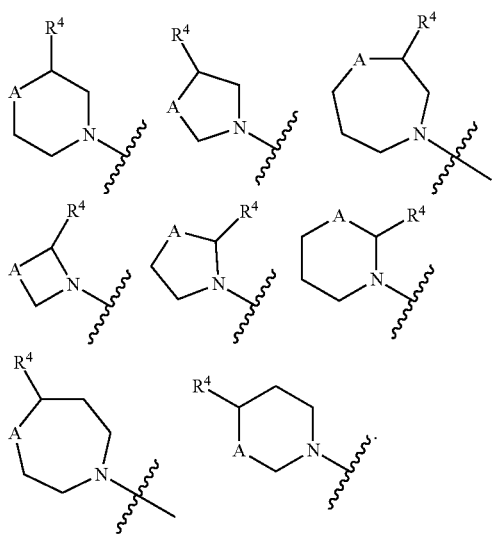

In one selected group of embodiments, m and n are both 0. In another selected group of embodiments, m and n are both 1. In yet another group of selected embodiments, m is 1 and n is 0. In still another group of embodiments, m is 1 and n is 2.

In still other selected embodiments, the ring having vertex A is represented by a formula selected from:

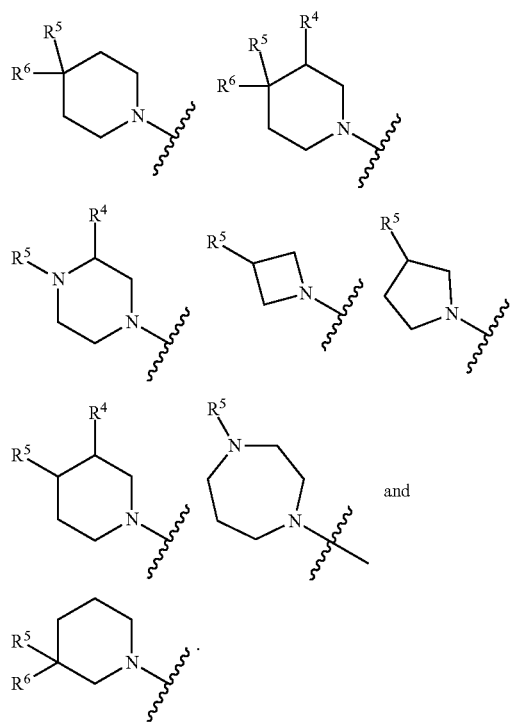

In one subgroup of embodiments, the compounds of formula (I) are represented by:

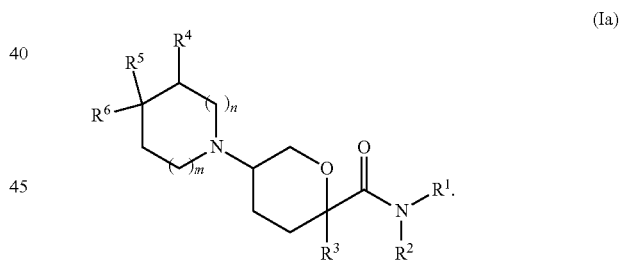

(Ia)

Within formula (Ia), a number of selected embodiments are provided as formulae Ia1, Ia2, Ia3, Ia4 and Ia5.

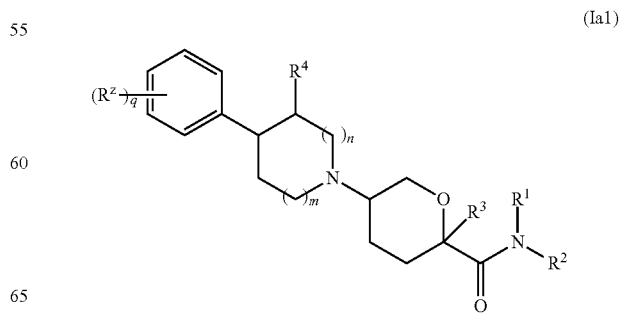

(Ia1)

-continued

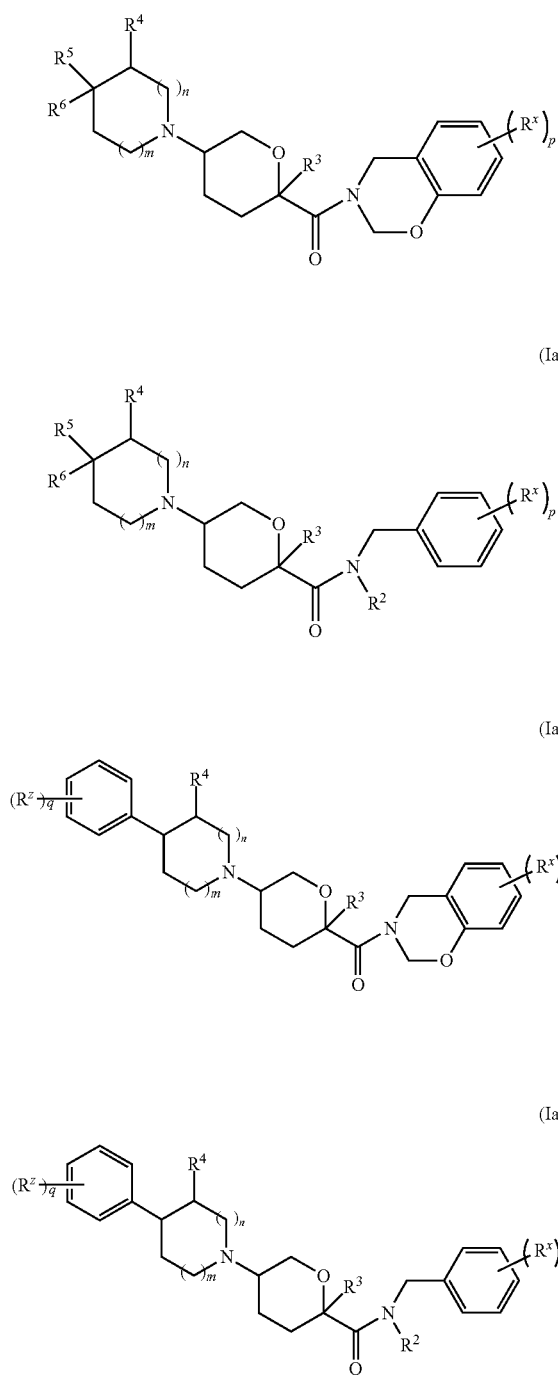

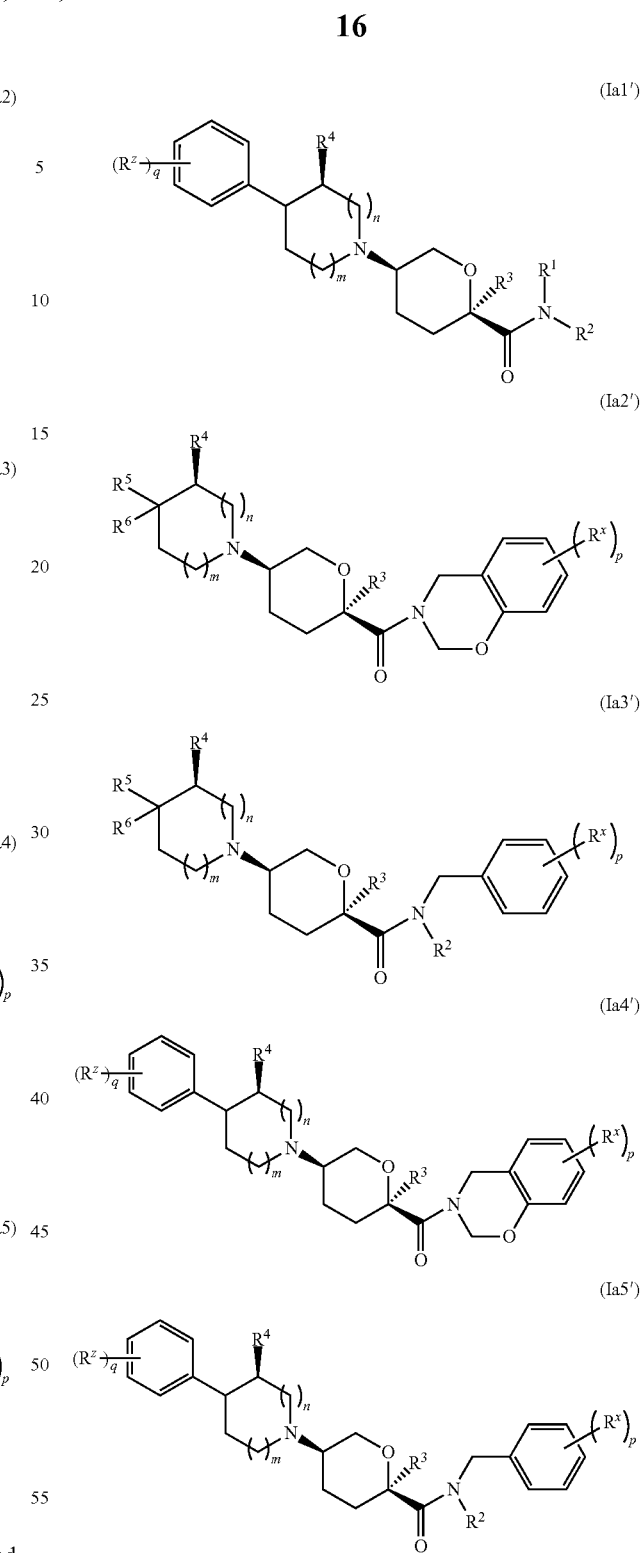

In each of formulae Ia, Ia1, Ia2, Ia3, Ia4 and Ia5, the noted substituents ($R^1$ through $R^6$, $R^x$ and $R^z$) and subscripts m and n have the meanings provided above with respect to formula I. The subscripts, p and q, have the following meanings: for Ia1, Ia4 and Ia5, the subscript q is an integer of from 0 to 5; for Ia2 and Ia4, the subscript p is an integer of from 0 to 4; and for Ia3 and Ia5, the subscript p is an integer of from 0 to 5.

In still other selected embodiments, the compounds provided herein are represented by formulae selected from:

wherein each compound is substantially free of other stereoisomers, and wherein the noted substituents ($R^1$ through $R^6$, $R^x$ and $R^z$) and subscripts m and n have the meanings provided above with respect to formula I. The subscripts, p and q, have the following meanings: for Ia1', Ia4' and Ia5', the subscript q is an integer of from 0 to 5; for Ia2' and Ia4', the subscript p is an integer of from 0 to 4; and for Ia3' and Ia5', the subscript p is an integer of from 0 to 5.

In another group of embodiments of formula I, A is C(R$^5$)(R$^6$), wherein R$^5$ and R$^6$ are combined to form a ring. Selected embodiments are provided as follows:

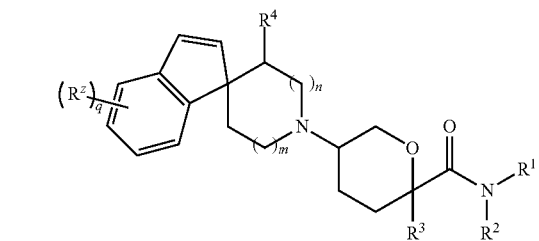

(Ib)

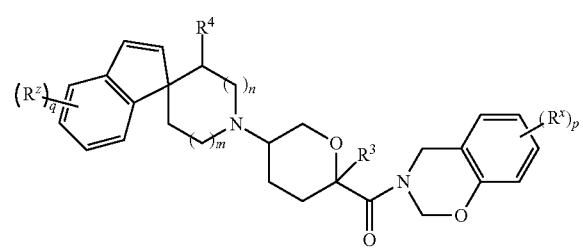

(Ib1)

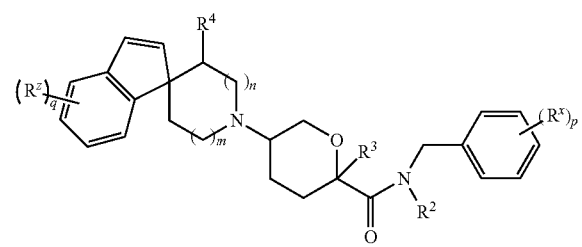

(Ib2)

In each of formulae Ib, Ib1 and Ib2, the noted substituents (R$^1$ through R$^6$, R$^x$ and R$^z$) and subscripts m and n have the meanings provided above with respect to formula I. The subscripts, p and q, have the following meanings: for Ib, Ib1 and Ib2, the subscript q is an integer of from 0 to 5; for Ib1, the subscript p is an integer of from 0 to 4; and for Ib2, the subscript p is an integer of from 0 to 5.

In another group of embodiments of formula I, A is NR$^5$ (see formula Ic). Selected embodiments are provided as follows:

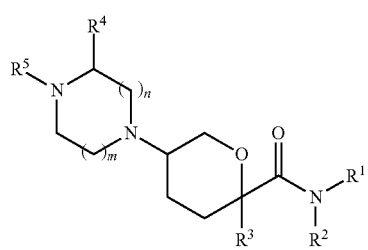

(Ic)

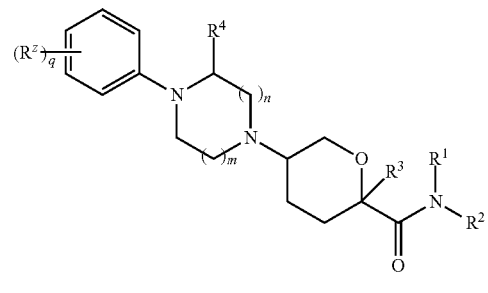

(Ic1)

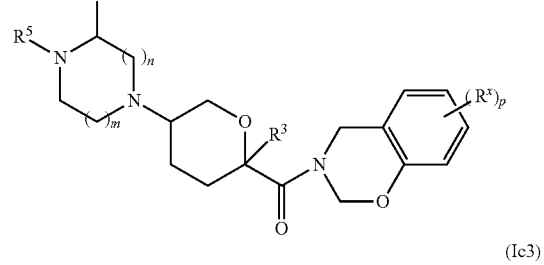

(Ic2)

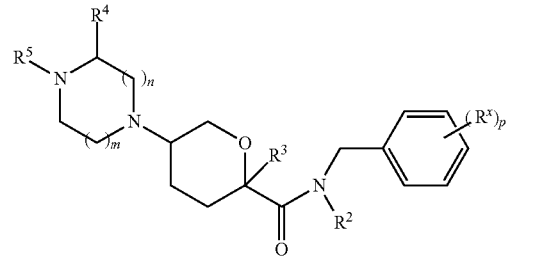

(Ic3)

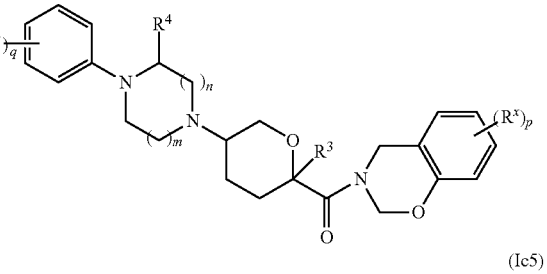

(Ic4)

(Ic5)

In each of formulae Ic, Ic1, Ic2, Ic3, Ic4 and Ic5, the noted substituents (R$^1$ through R$^6$, R$^x$ and R$^z$) and subscripts m and n have the meanings provided above with respect to formula I. The subscripts, p and q, have the following meanings: for Ic1, Ic4 and Ic5, the subscript q is an integer of from 0 to 5; for Ic2 and Ic4, the subscript p is an integer of from 0 to 4; and for Ic3 and Ic5, the subscript p is an integer of from 0 to 5.

In still other selected embodiments, the compounds provided herein are represented by formulae selected from:

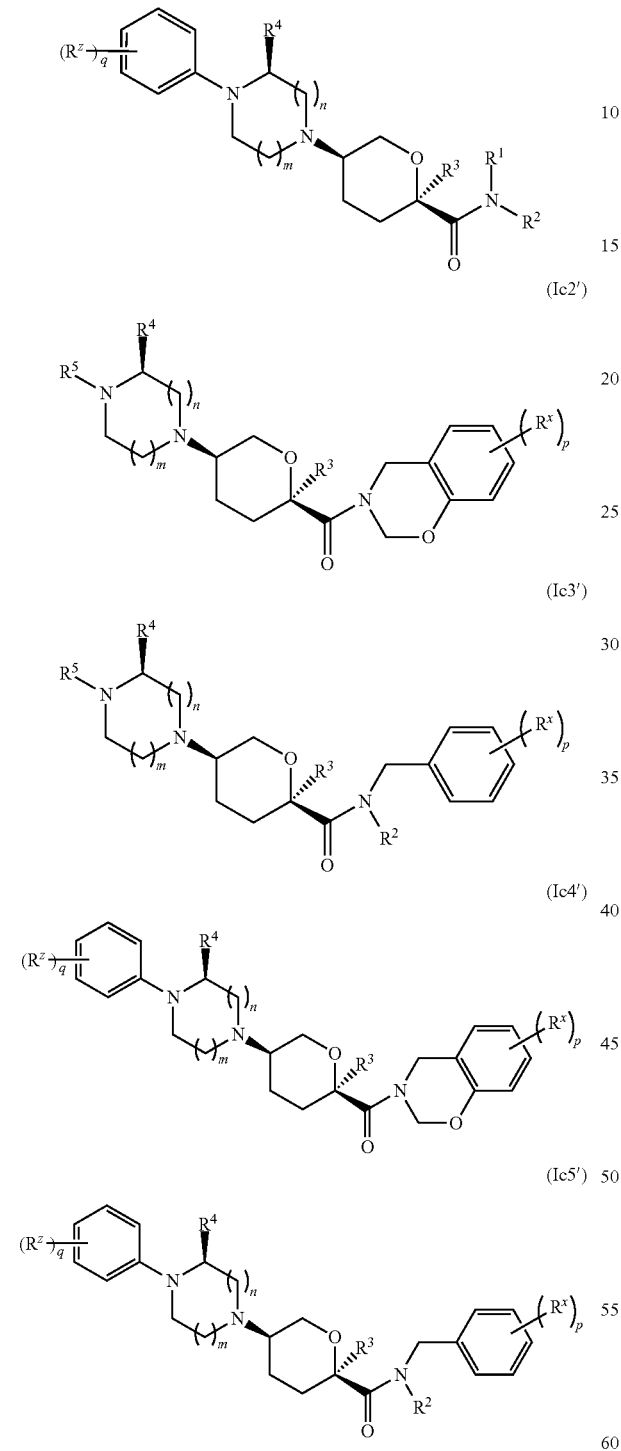

wherein each compound is substantially free of other stereoisomers, and wherein the noted substituents ($R^1$ through $R^6$, $R^x$ and $R^z$) and subscripts m and n have the meanings provided above with respect to formula I. The subscripts, p and q, have the following meanings: for Ic1', Ic4' and Ic5', the subscript q is an integer of from 0 to 5; for Ic2' and Ic4', the subscript p is an integer of from 0 to 4; and for Ic3' and Ic5', the subscript p is an integer of from 0 to 5.

Other selected embodiments, compounds are provided in each of I, Ia, Ia1, Ia1', Ib, Ic, Ic1 and Ic1', described above, wherein —$N(R^1)(R^2)$ is selected from:

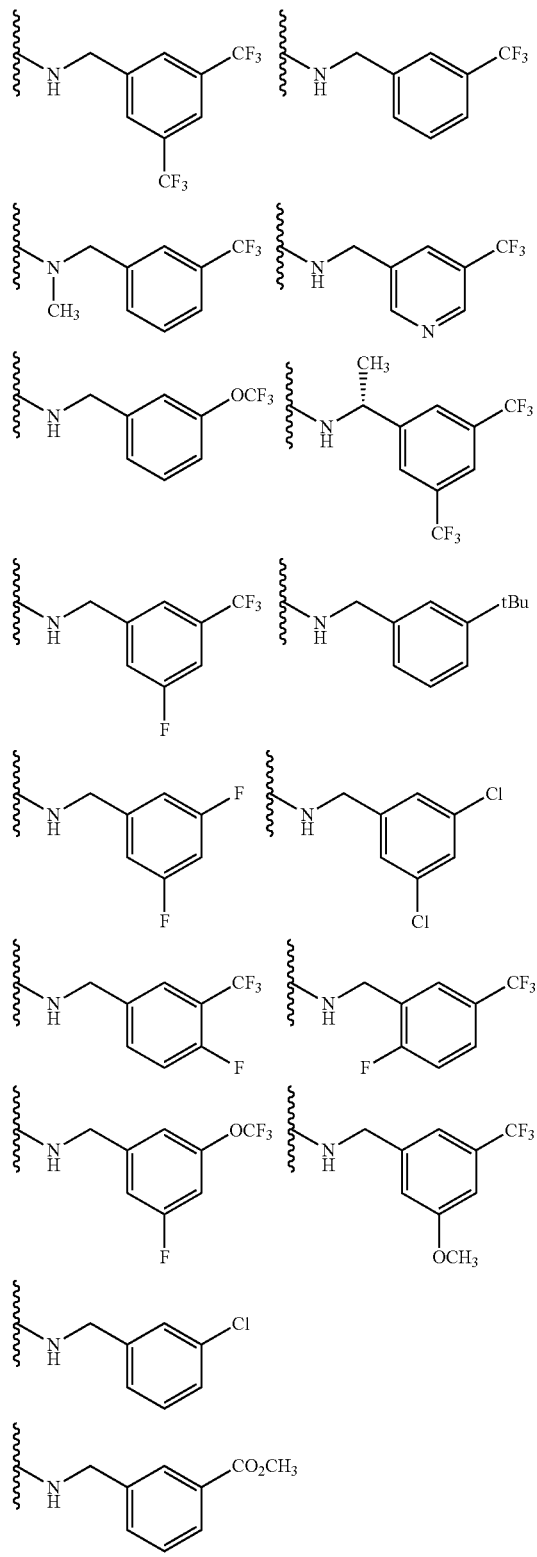

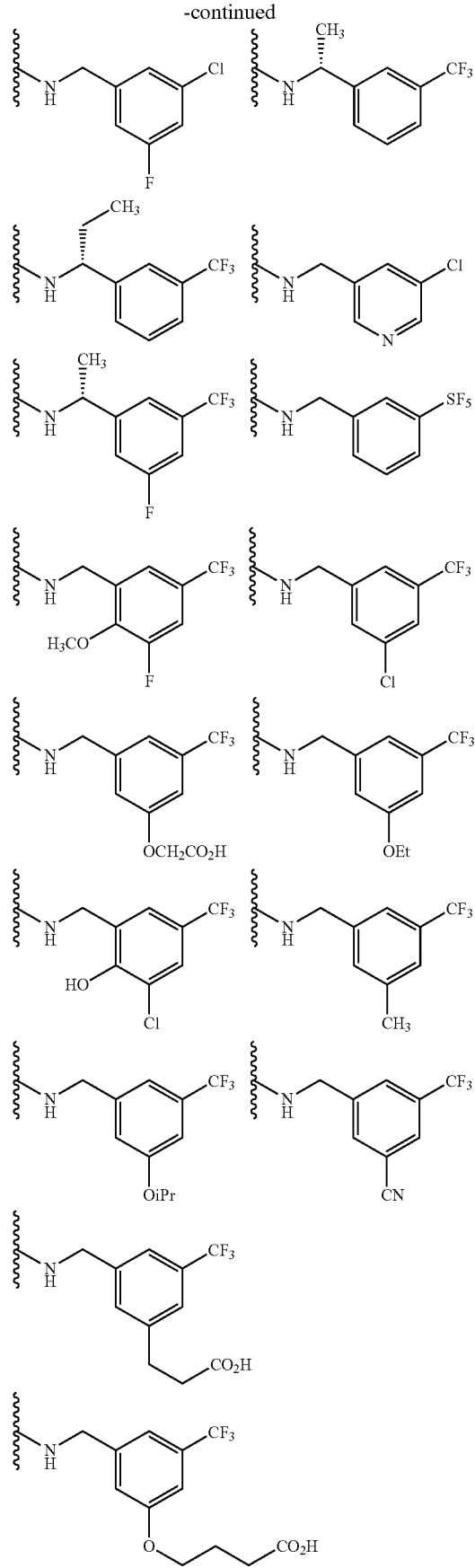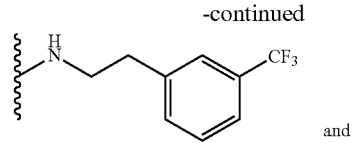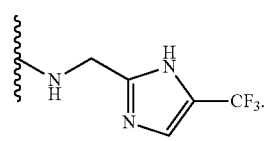
Still other selected embodiments, are provided in each of I, Ia, Ia1', Ib, Ic, Ic1 and Ic1', described above, wherein —N(R$^1$)(R$^2$) is selected from:
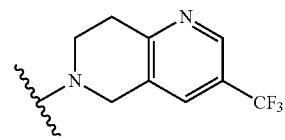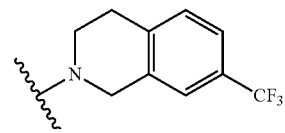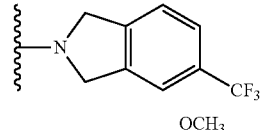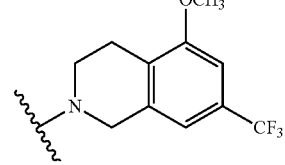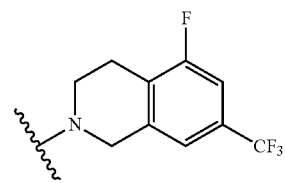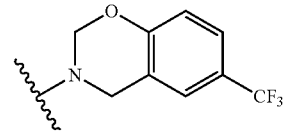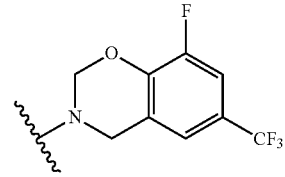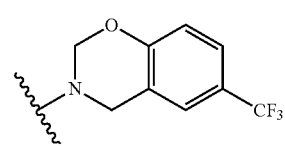

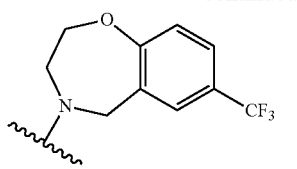
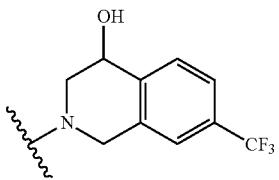
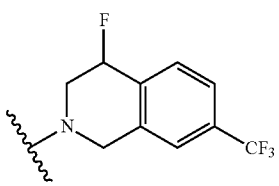
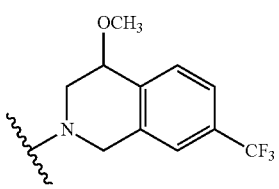
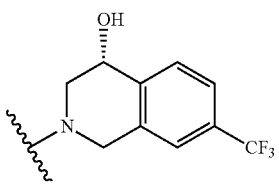
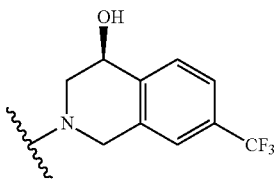
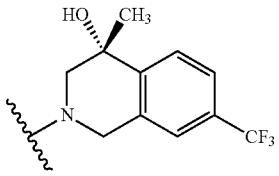
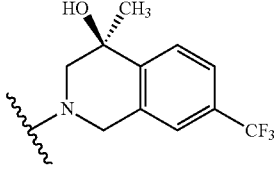
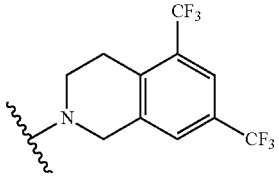
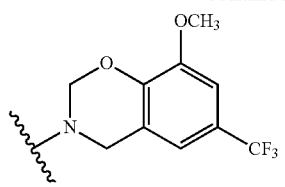
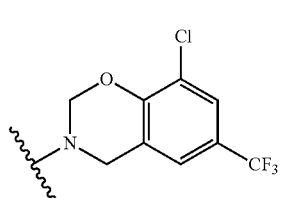
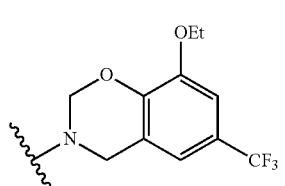
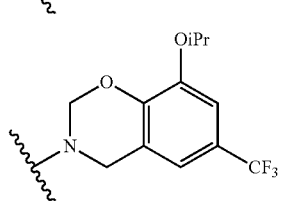
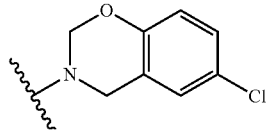
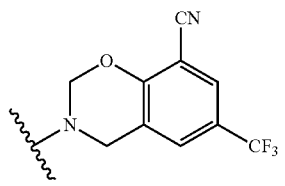
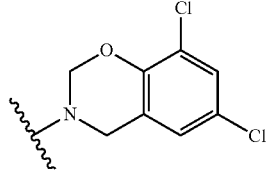
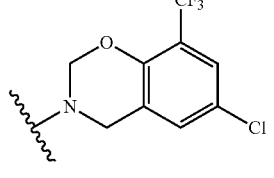
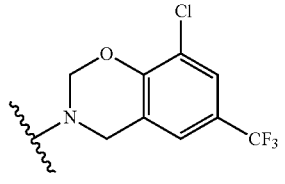
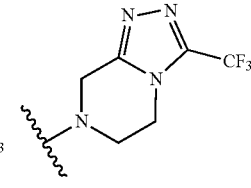

-continued

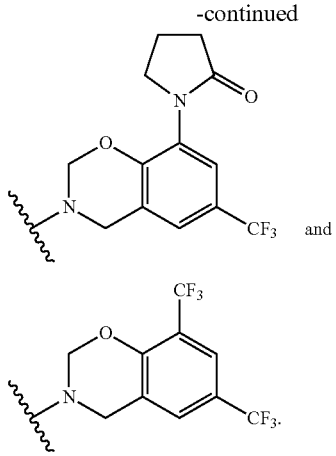

Yet other selected embodiments, are provided in each of I, Ia, Ia1, Ia1', Ib, Ic, Ic1 and Ic1', described above, wherein —N(R¹)(R²) is selected from:

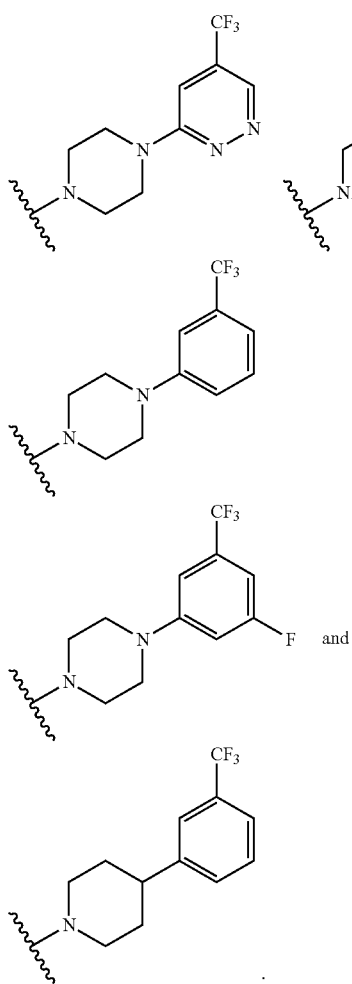

In some embodiments, compounds of formulae I, Ia, Ia2, Ia3, Ia2' and Ia3', are provided wherein A is C(R⁵)(R⁶), or is shown in the formula as C(R⁵)(R⁶), wherein R⁵ is selected from aryl, aryloxy, arylamino, aryl-C$_{1-4}$ alkyl, heteroaryl, heteroaryloxy, heteroarylamino and heteroaryl-C$_{1-4}$ alkyl, wherein the aryl or heteroaryl groups or portions are selected from:

Group 1

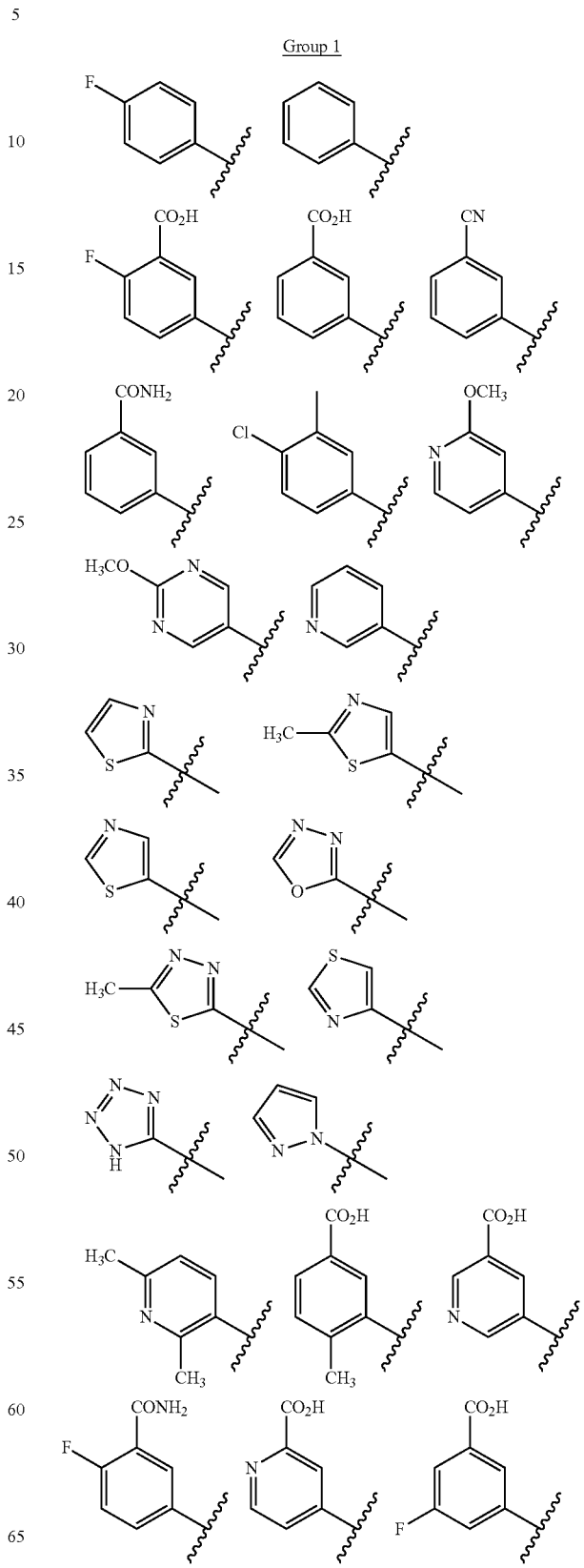

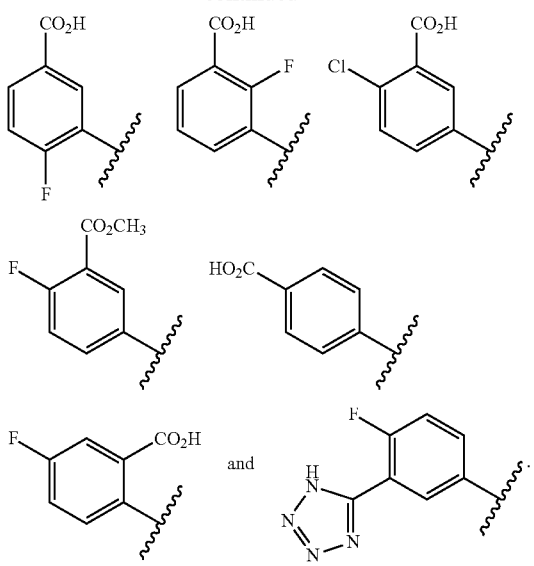

In certain selected embodiments, compounds of formulae I, Ia, Ia2, Ia3, Ia2' and Ia3', are provided wherein A is $C(R^5)(R^6)$, or is shown in the formula as $C(R^5)(R^6)$, wherein $R^5$ is selected from aryl, aryloxy, arylamino and aryl-$C_{1-4}$ alkyl, wherein the aryl group or portion is selected from:

Subgroup 1a

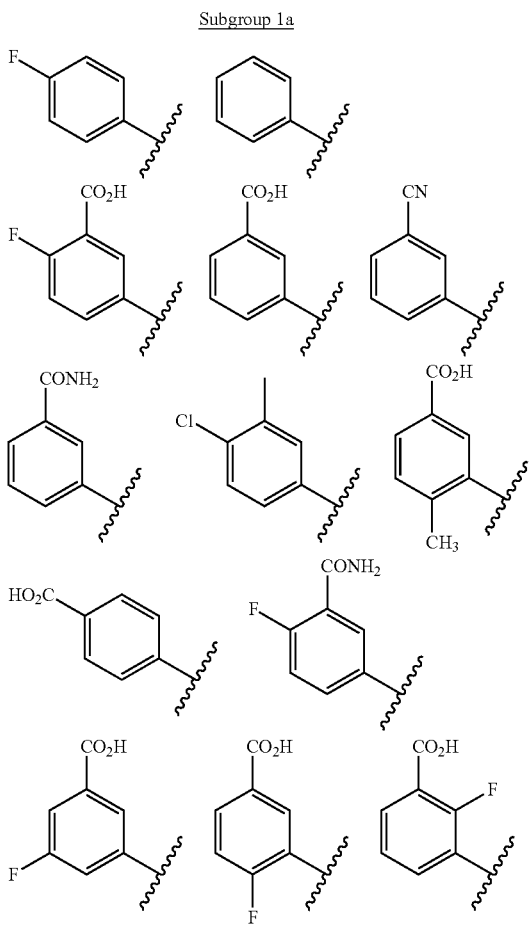

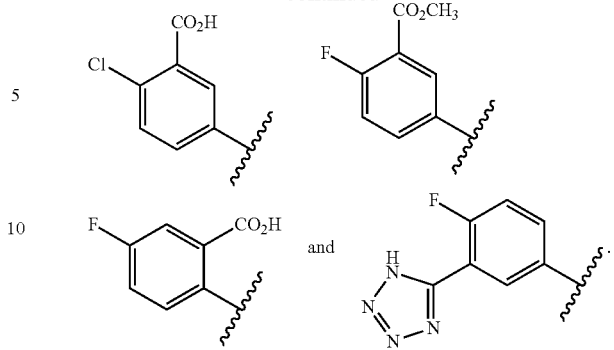

In still other selected embodiments, compounds of formulae I, Ia, Ia2, Ia3, Ia2' and Ia3', are provided wherein A is $C(R^5)(R^6)$, or is shown in the formula as $C(R^5)(R^6)$, wherein $R^5$ is selected from heteroaryl, heteroaryloxy, heteroarylamino and heteroaryl-$C_{1-4}$ alkyl, wherein the heteroaryl group or portion is selected from:

Subgroup 1b

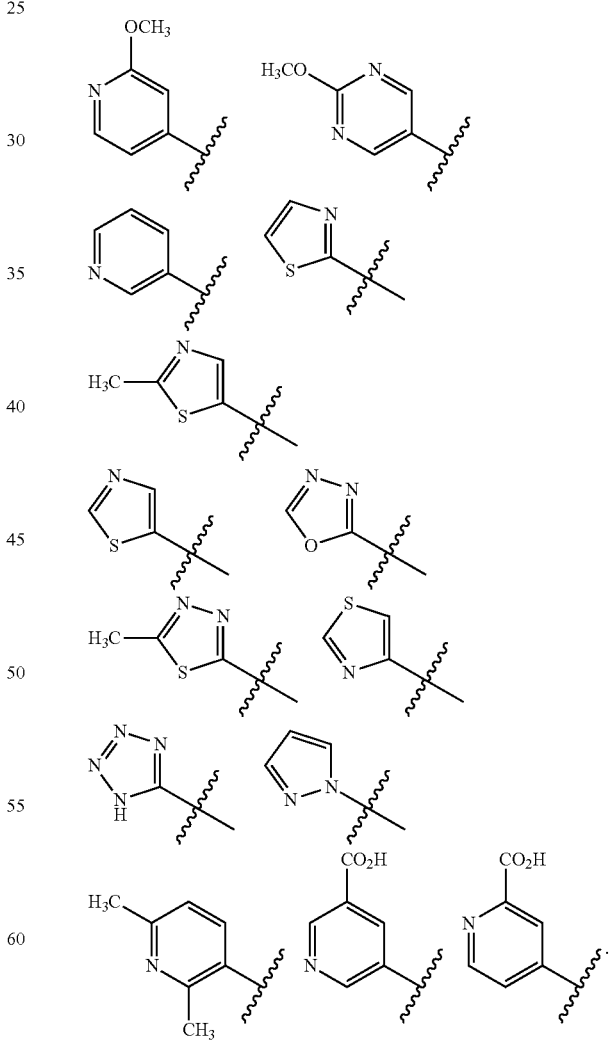

In some embodiments, compounds of formulae I, Ic, Ic2, Ic3, Ic2' and Ic3', are provided wherein A is $N(R^5)$, or is shown in the formula as N(R⁵), wherein R⁵ is selected from aryl, aryl-$C_{1-4}$ alkyl, heteroaryl and heteroaryl-$C_{1-4}$ alkyl, wherein the aryl or heteroaryl groups or portions are selected from Group 1 above. In certain selected embodiments, compounds of formulae I, Ic, Ic2, Ic3, Ic2' and Ic3', are provided wherein A is N(R⁵), or is shown in the formula as N(R⁵), wherein R⁵ is selected from aryl and aryl-$C_{1-4}$ alkyl, wherein the aryl group or portion is selected from Subgroup 1a, above. In still other selected embodiments, compounds of formulae I, Ic, Ic2, Ic3, Ic2' and Ic3', are provided wherein A is N(R⁵), or is shown in the formula as N(R⁵), wherein R⁵ is selected from heteroaryl and heteroaryl-$C_{1-4}$ alkyl, wherein the heteroaryl group or portion is selected from Subgroup 1b, above.

Preparation of Compounds

Those skilled in the art will recognize that there are a variety of methods available to synthesize molecules represented in the claims. In general, useful methods for synthesizing compounds represented in the claims are shown in Scheme 1:

Variations on the methods shown above have been used to prepare compounds of the invention, some of which are described in the examples.

Figure 1C:
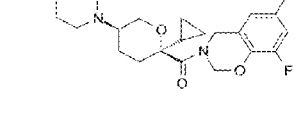
Figure 1E:
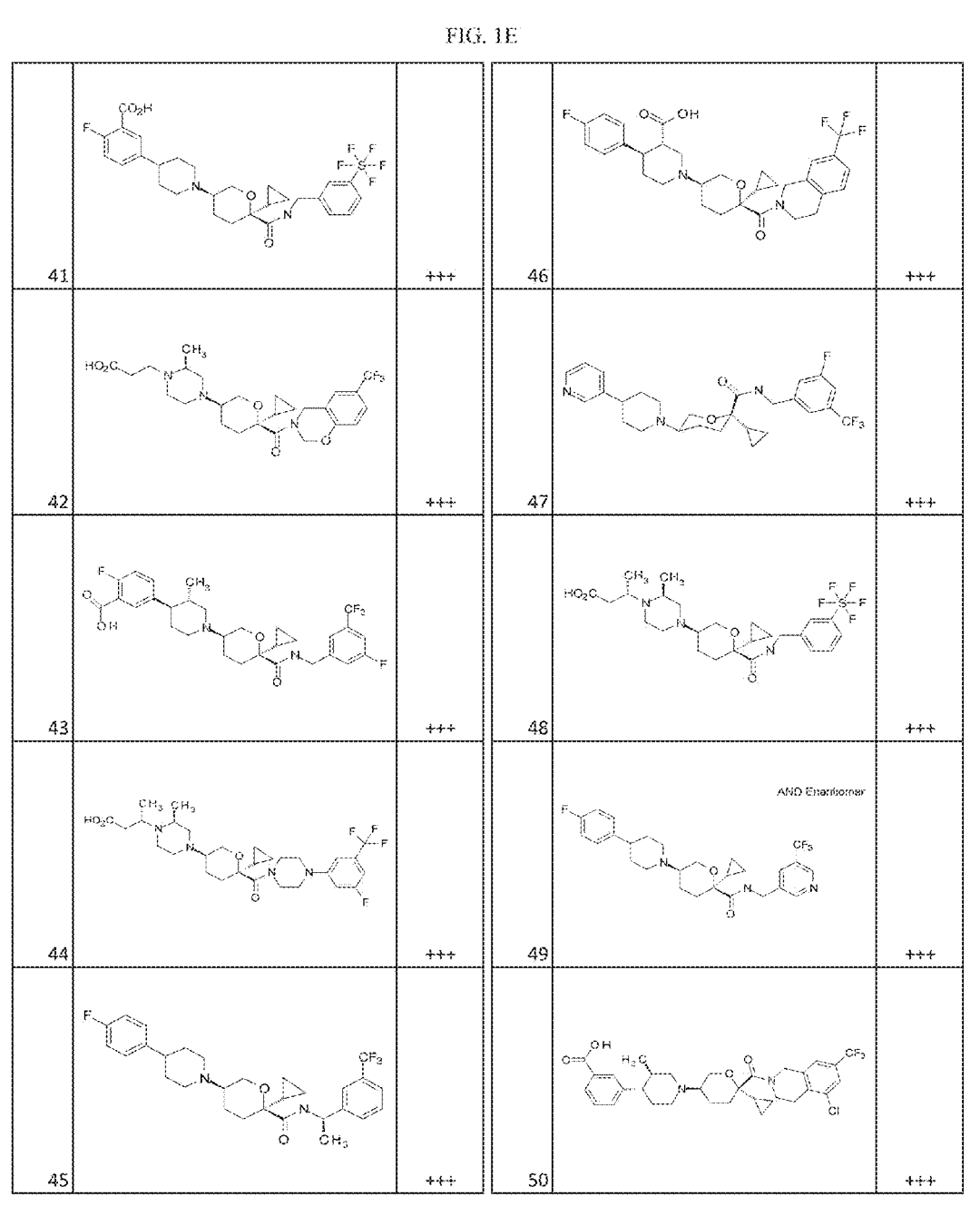
Figure 1G:
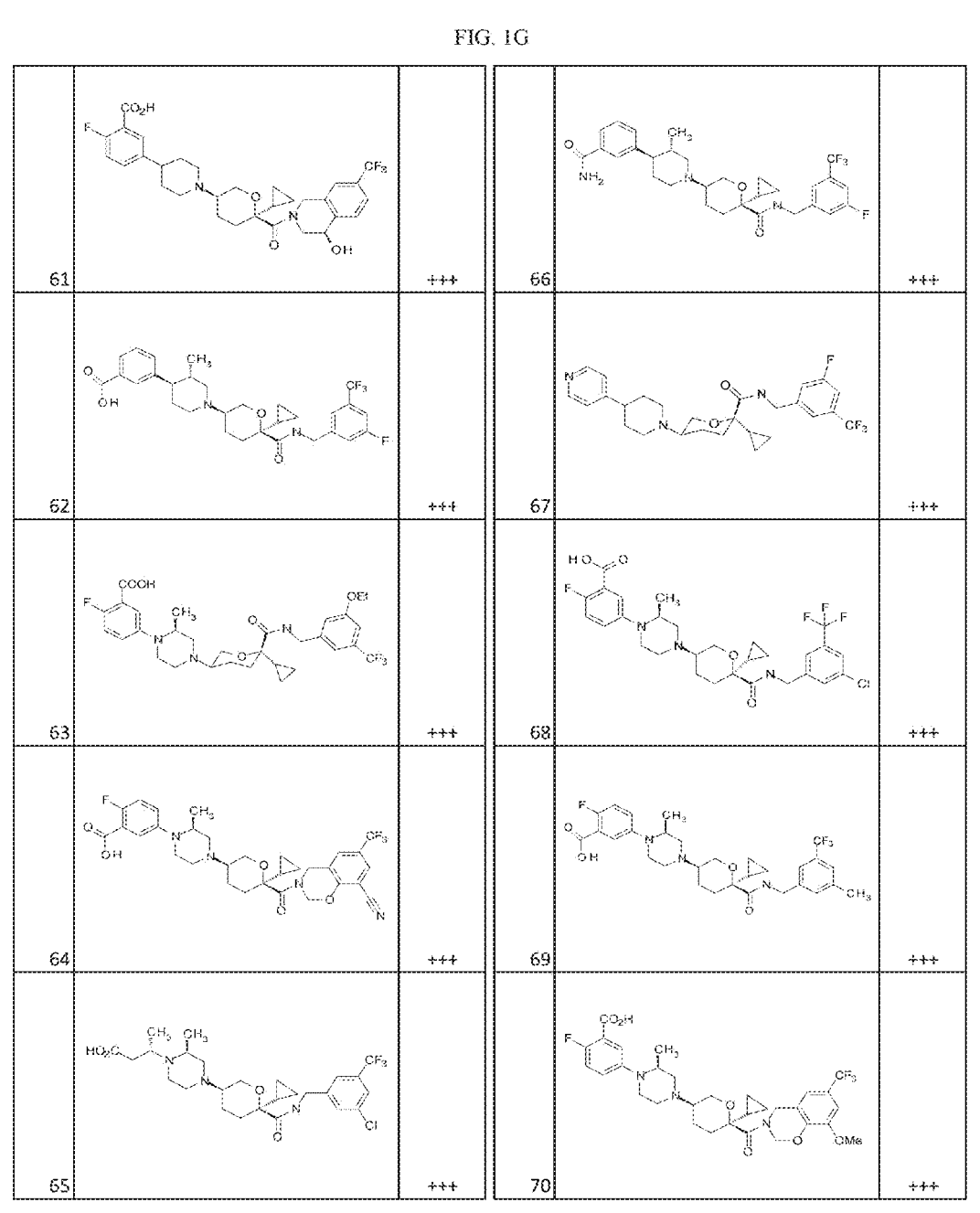
Figure 1H:
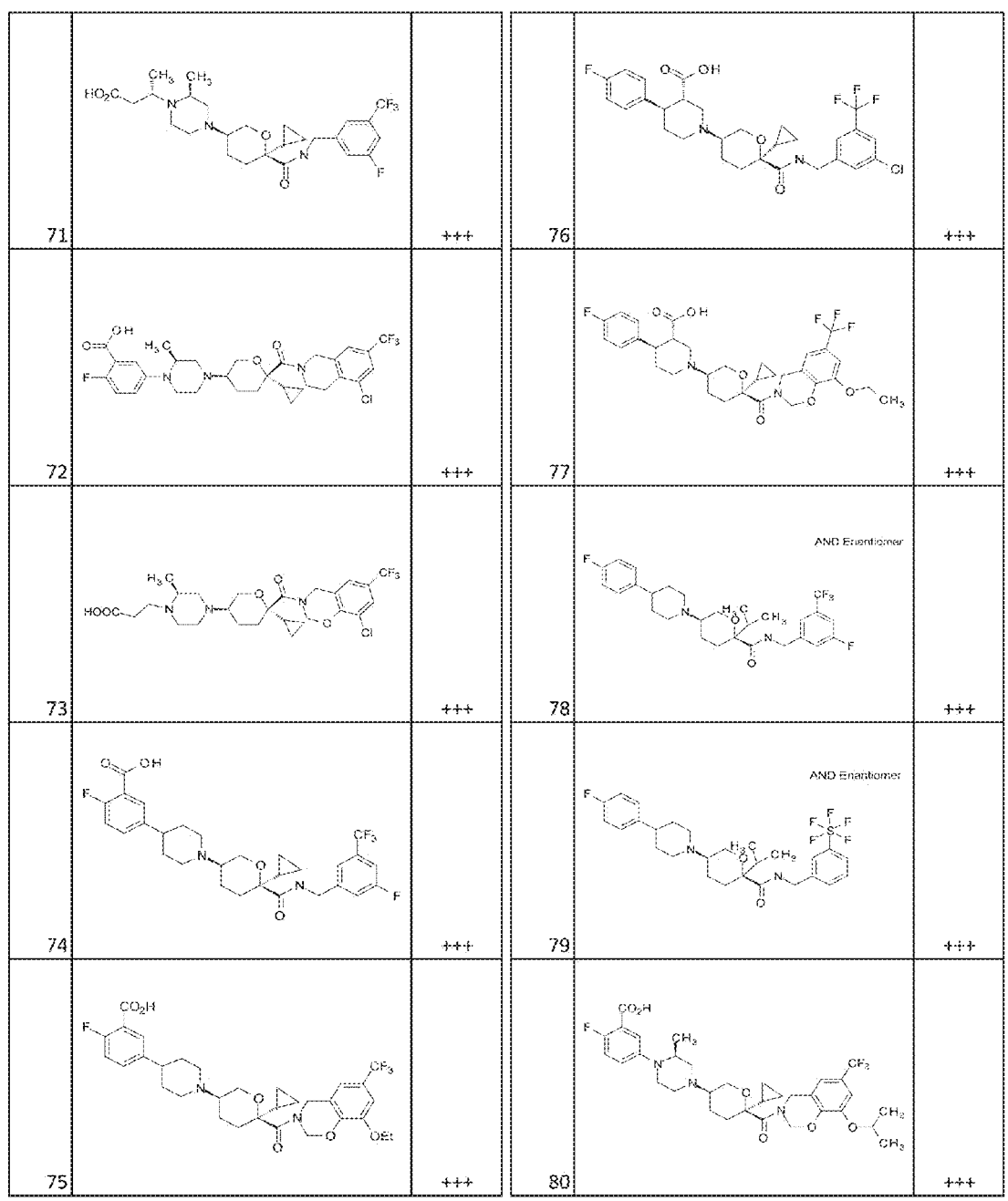
Figure 11:
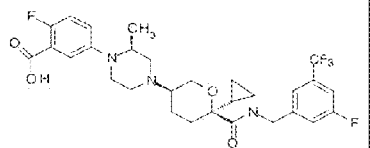
Figure 1J:
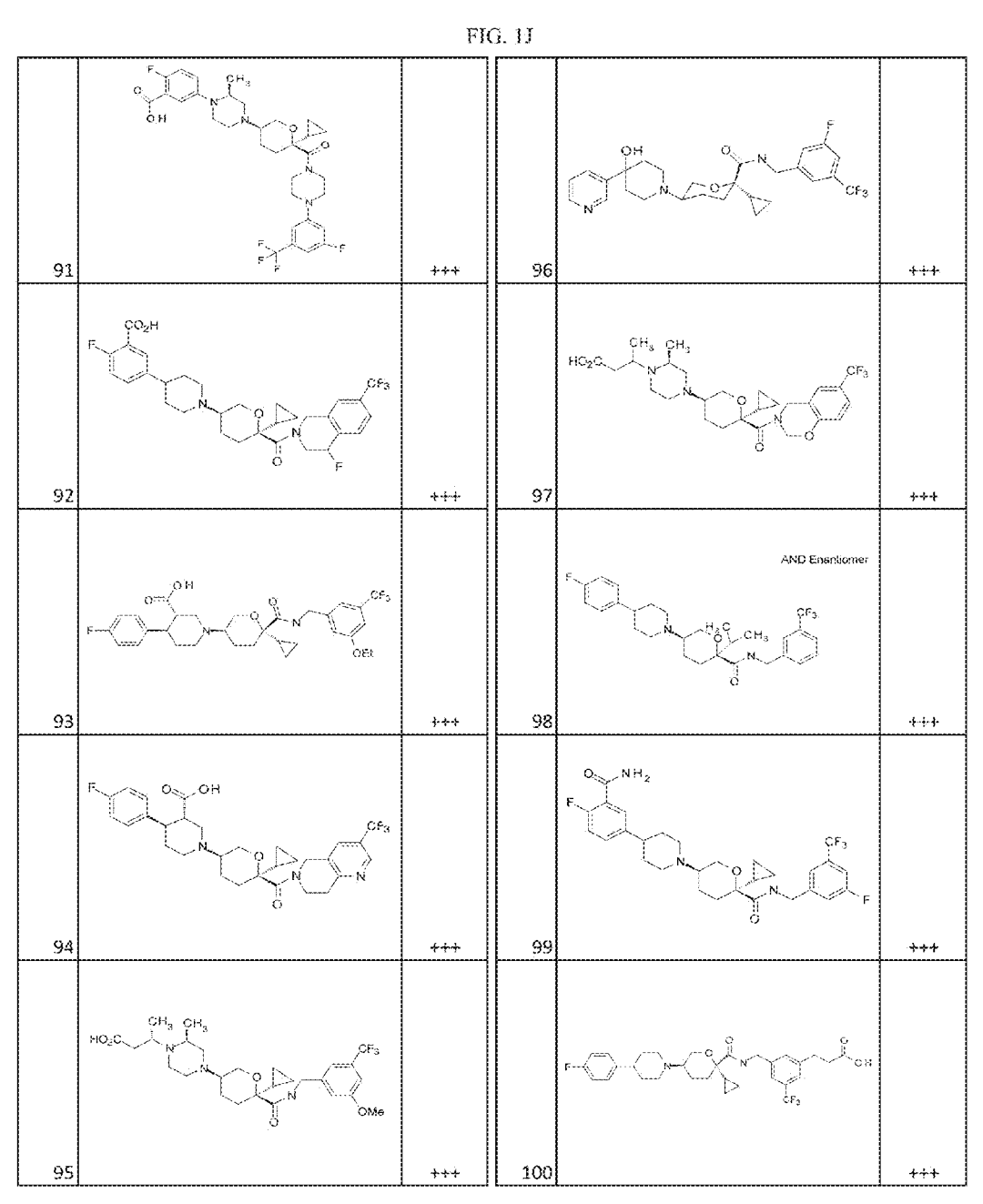
Figure 1L:
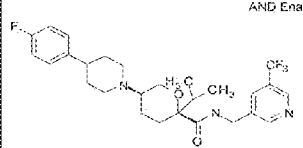
Figure 1M:
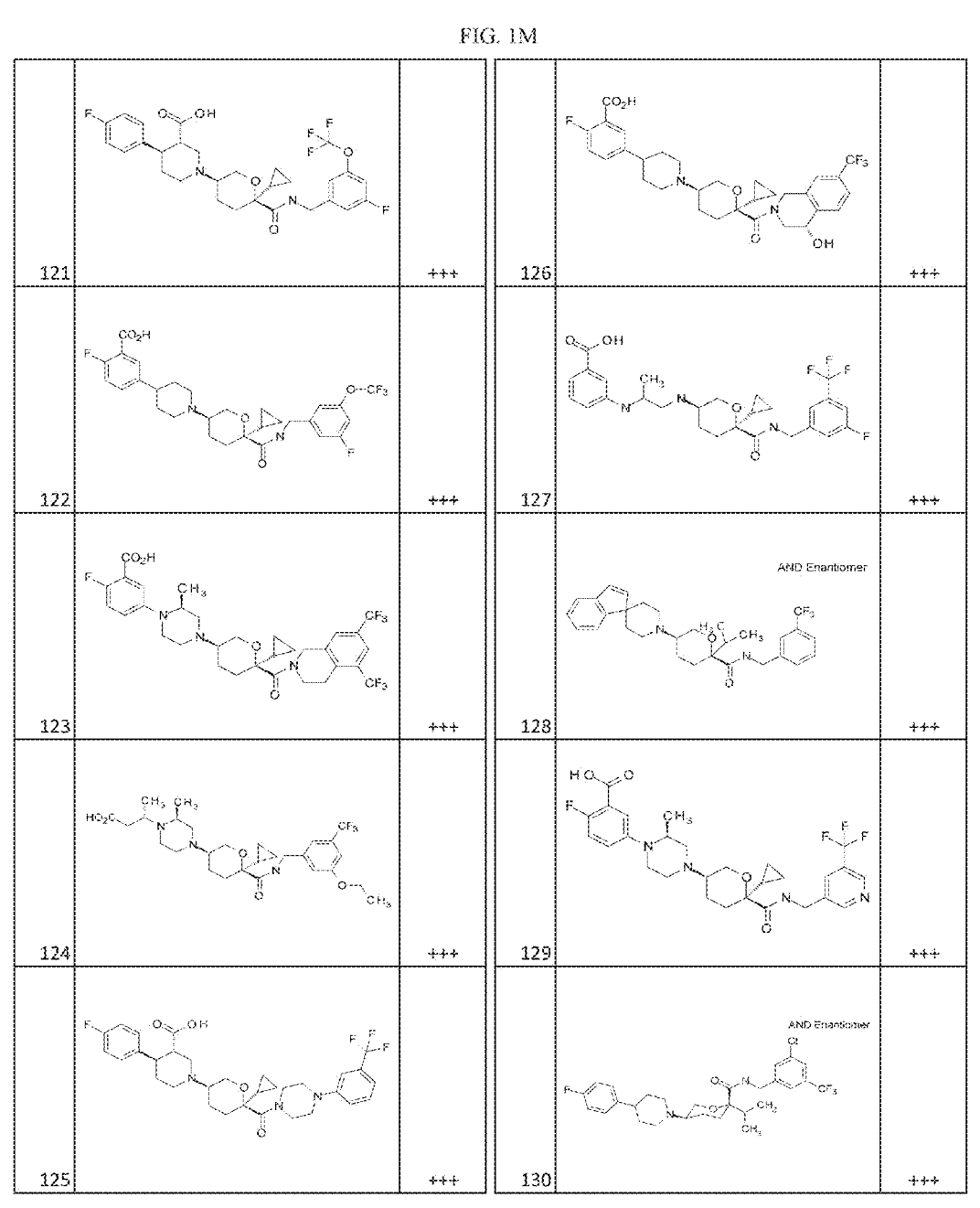
Figure 1N:
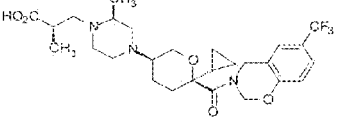
Figure 10:
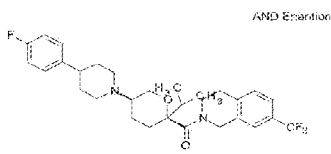
Figure 1P:
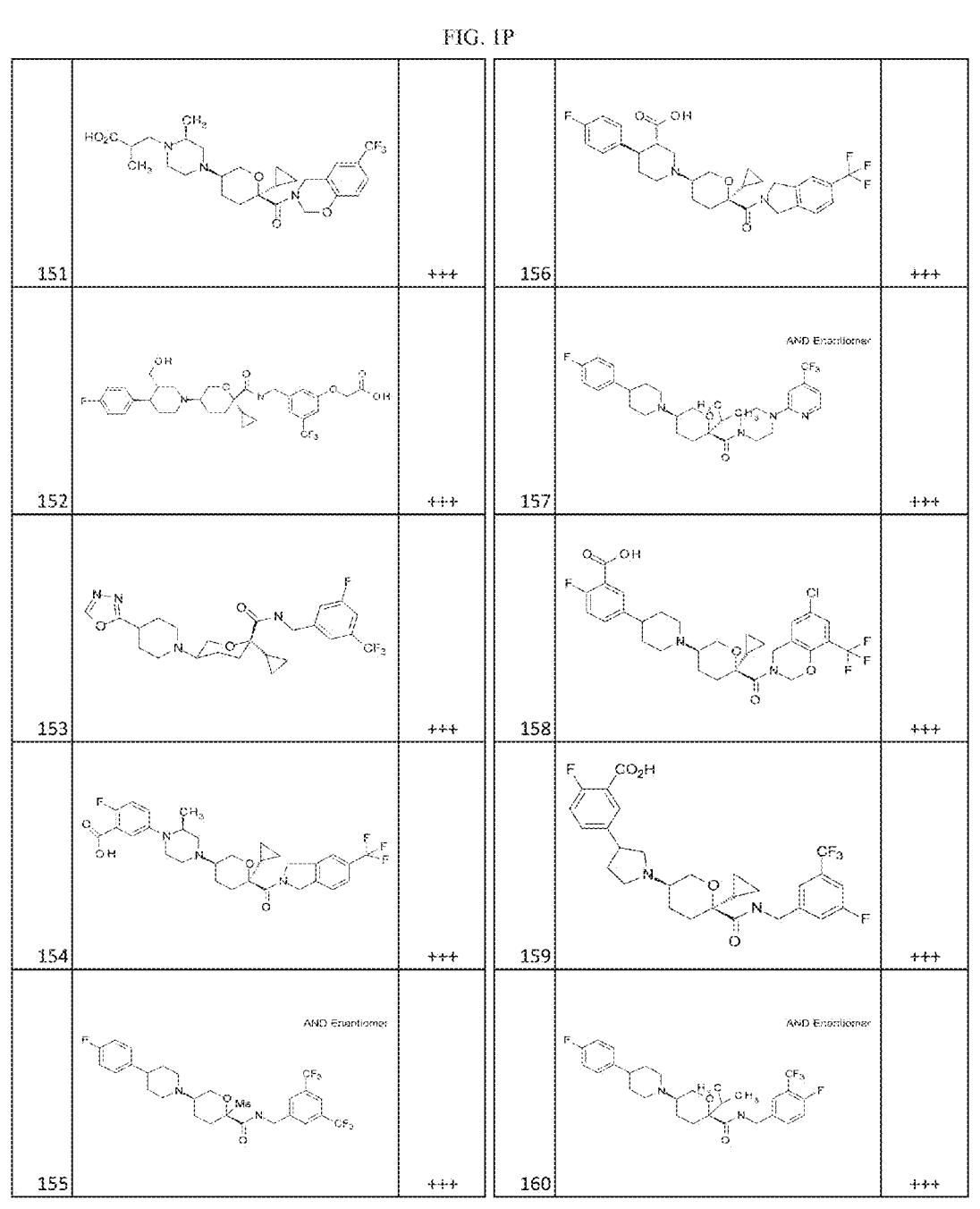
Figure 1Q:
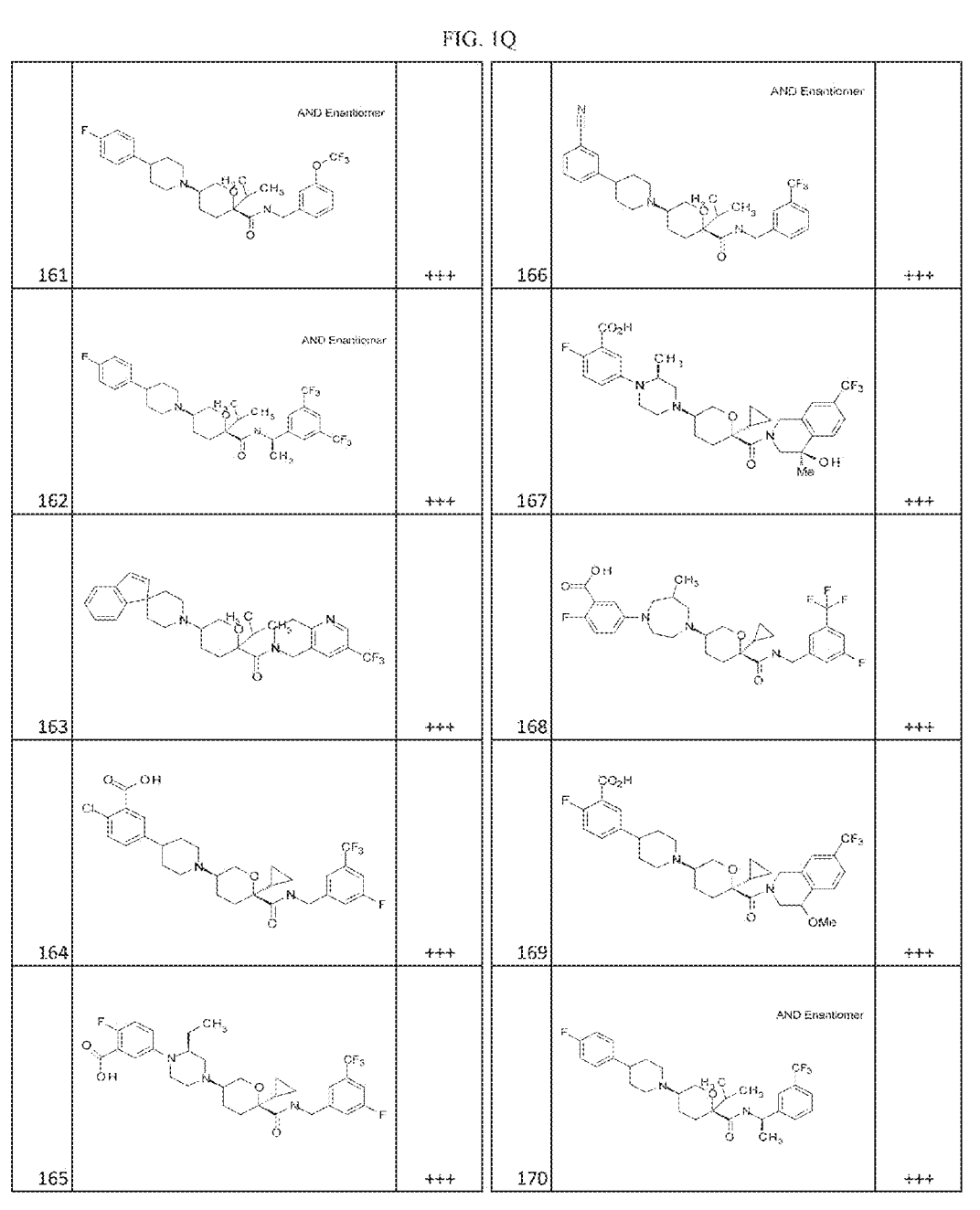
Figure 1U:
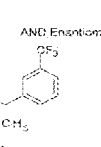
Figure 1W:
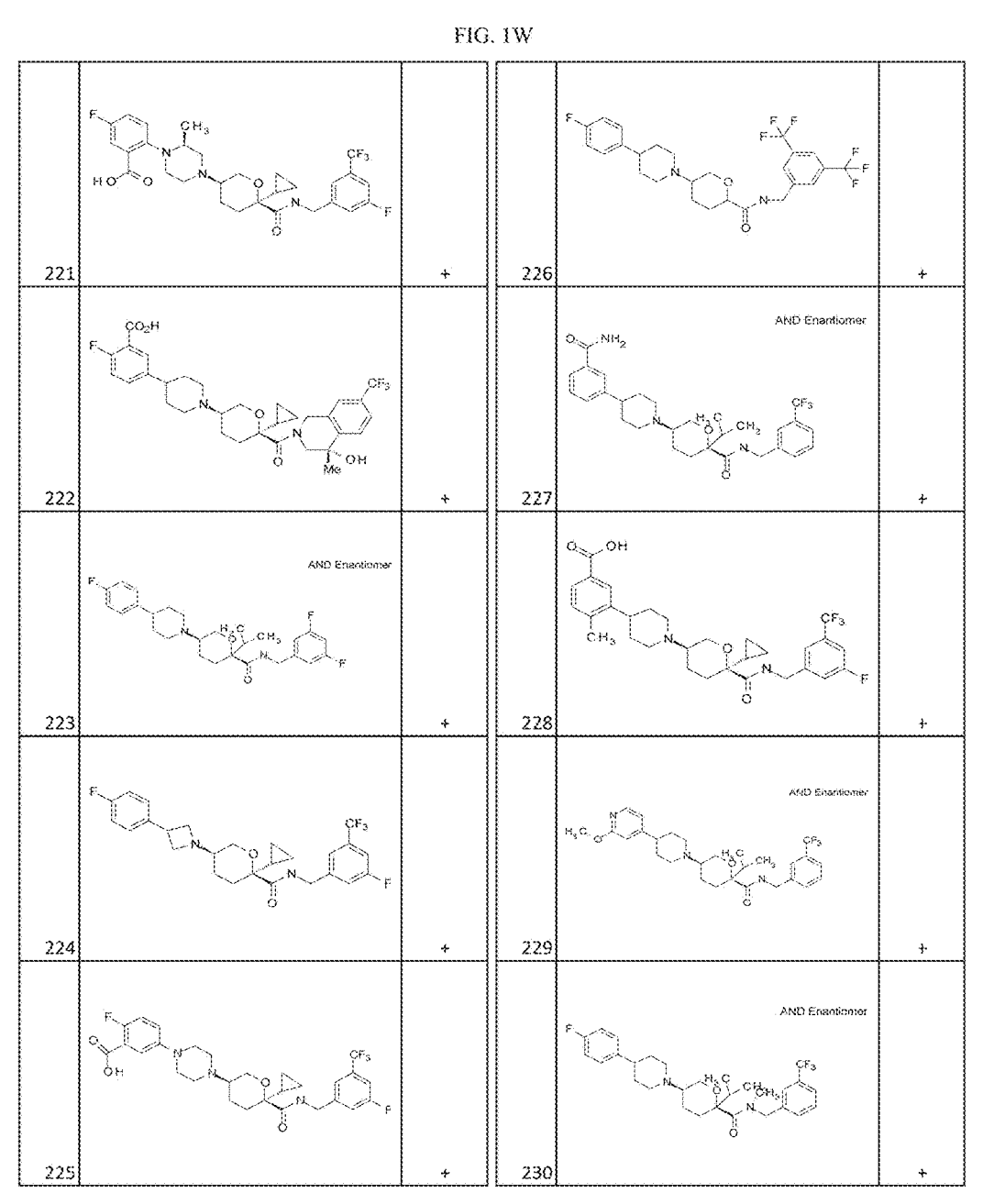
Figure 1X:
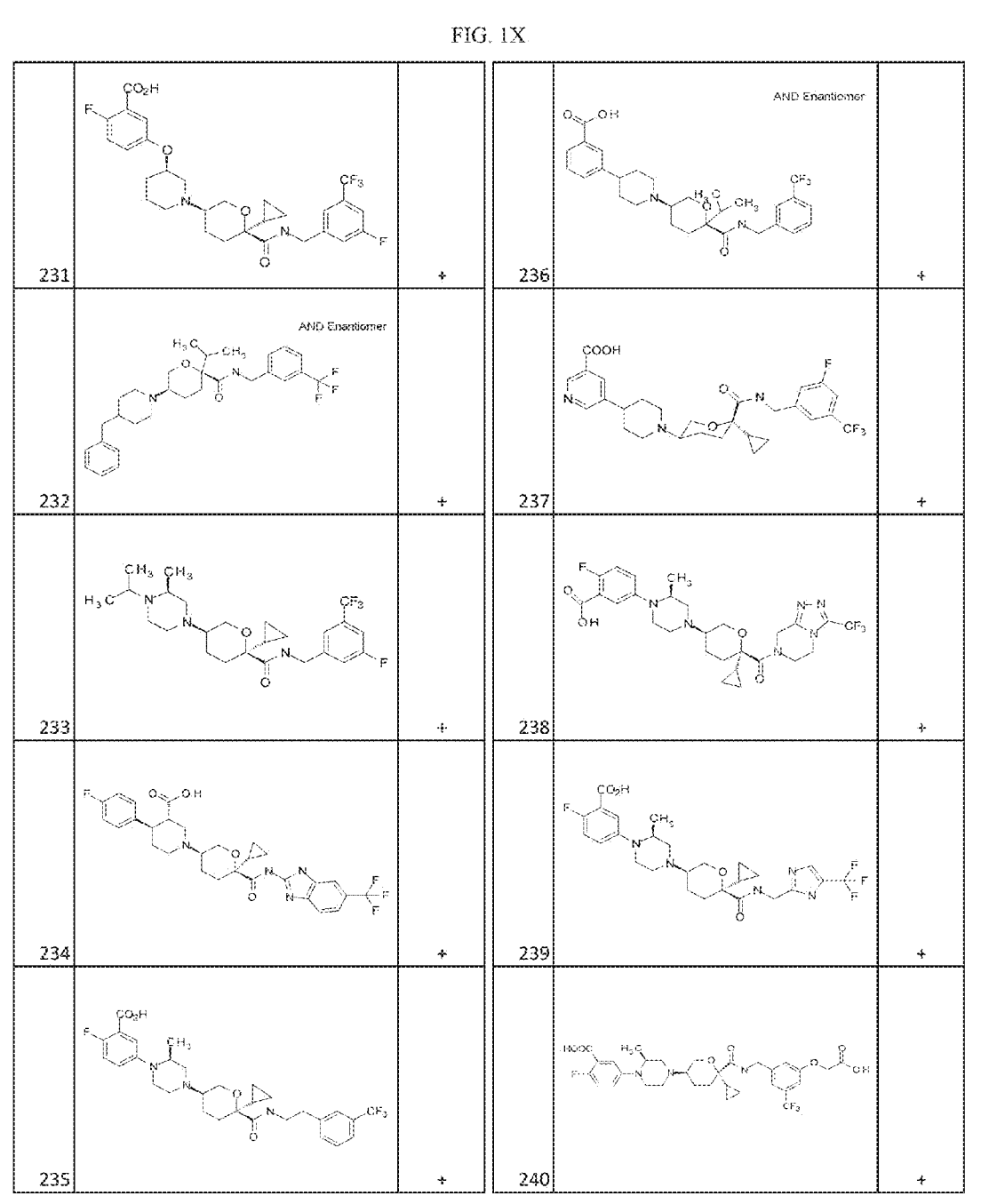
Figure 1Y:
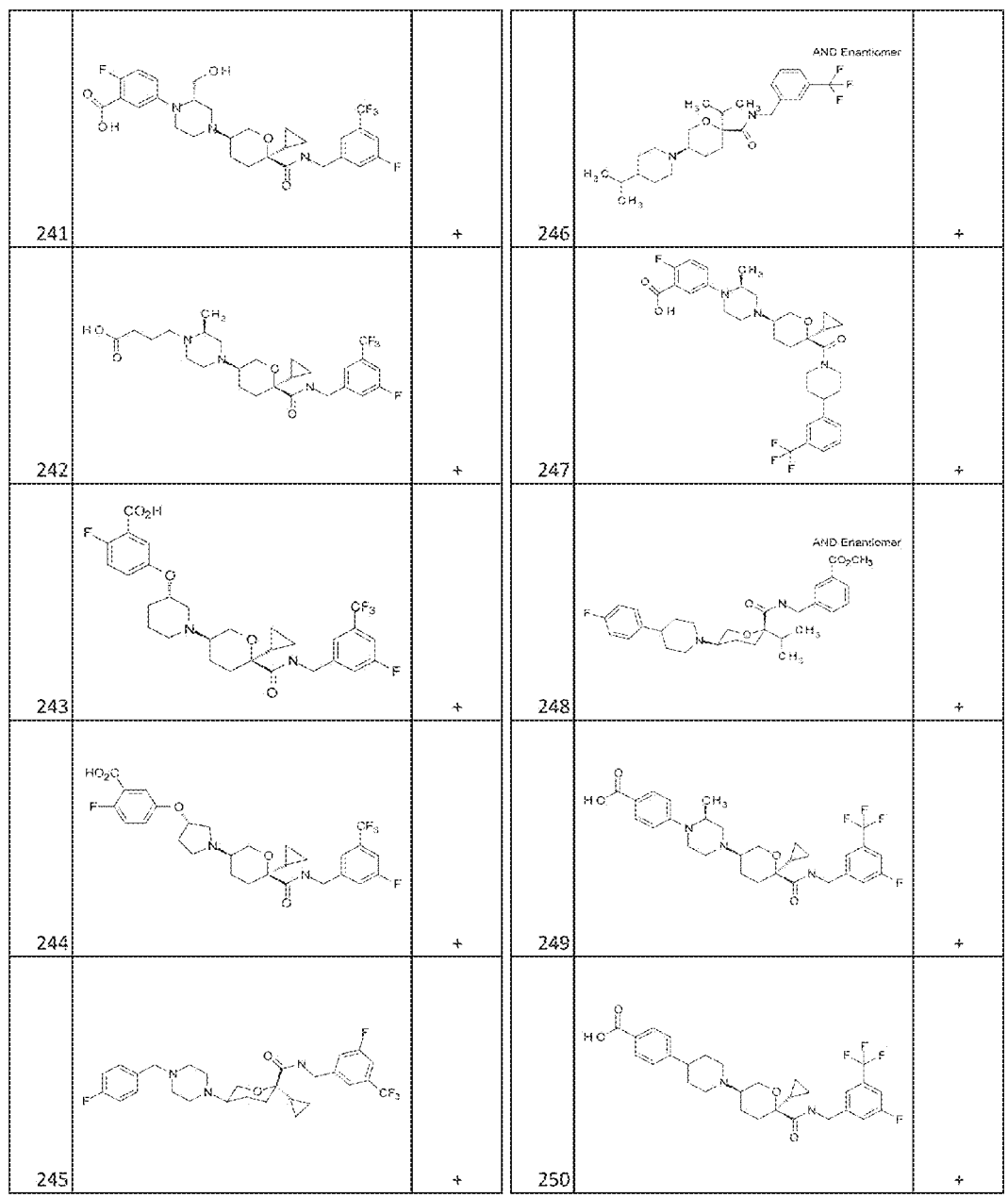

A family of specific compounds of particular interest having formula I consists of compounds, pharmaceutically acceptable salts, hydrates, stereoisomers and rotamers thereof, as set forth in FIG. 1.

IV. Pharmaceutical Compositions

In addition to the compounds provided above, compositions for modulating CCR2 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

Scheme 1

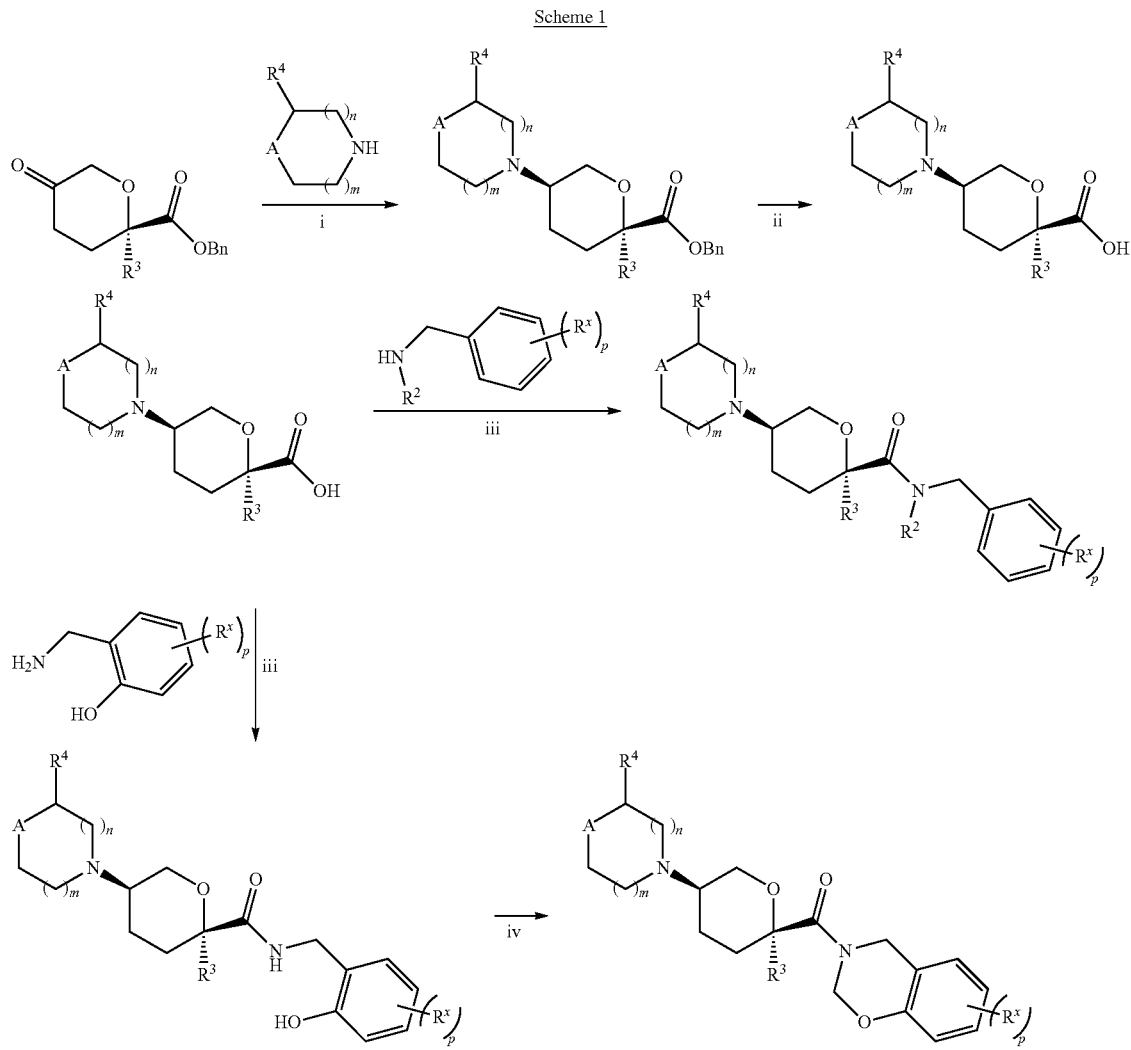

i: DIEA, NaBH(OAc)₃, DCE
ii: Pd/C, H₂, MeOH
iii: HATU, DIEA, DMF
iv: paraformaldehyde, TsOH, toluene, reflux The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, flavoring and/or coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled to a carrier that can be a suitable polymeric carrier as, for example, a targetable drug carrier. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

In some embodiments, a pharmaceutical composition comprising the compounds of the invention and further comprising one or more additional therapeutic compound is provided. In some embodiments, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a Thymidylate synthase inhibitor, an EGFR tyrosine kinase receptor inhibitor, an Epidermal growth factor antagonist, a Fyn tyrosine kinase inhibitor, a Kit tyrosine kinase inhibitor, a Lyn tyrosine kinase inhibitor, a NK cell receptor modulator, a PDGF receptor antagonist, a PARP inhibitor, a Poly ADP ribose polymerase inhibitor, a Poly ADP ribose polymerase 1 inhibitor, a Poly ADP ribose polymerase 2 inhibitor, a Poly ADP ribose polymerase 3 inhibitor, a Galactosyltransferase modulator, a Dihydropyrimidine dehydrogenase inhibitor, an Orotate phosphoribosyltransferase inhibitor, a Telomerase modulator, a Mucin 1 inhibitor, a Mucin inhibitor, a Secretin agonist, a TNF related apoptosis inducing ligand modulator, an IL17 gene stimulator, an Interleukin 17E ligand, a Neurokinin receptor agonist, a Cyclin G1 inhibitor, a checkpoint inhibitor, a PD-1 inhibitor, a PD-L1 inhibitor, a CTLA4 inhibitor, a Topoisomerase I inhibitor, an Alk-5 protein kinase inhibitor, a Connective tissue growth factor ligand inhibitor, a Notch-2 receptor antagonist, a Notch-3 receptor antagonist, a Hyaluronidase stimulator, a MEK-1 protein kinase inhibitor; MEK-2 protein kinase inhibitor, a GM-CSF receptor modulator; TNF alpha ligand modulator, a Mesothelin modulator, an Asparaginase stimulator, a Caspase-3 stimulator; Caspase-9 stimulator, a PKN3 gene inhibitor, a Hedgehog protein inhibitor; Smoothened receptor antagonist, an AKT1 gene inhibitor, a DHFR inhibitor, a Thymidine kinase stimulator, a CD29 modulator, a Fibronectin modulator, an Interleukin-2 ligand, a Serine protease inhibitor, a D40LG gene stimulator; TNFSF9 gene stimulator, a 2 oxoglutarate dehydrogenase inhibitor, a TGF-beta type II receptor antagonist, an Erbb3 tyrosine kinase receptor inhibitor, a Cholecystokinin CCK2 receptor antagonist, a Wilms tumor protein modulator, a Ras GTPase modulator, an Histone deacetylase inhibitor, a Cyclin-dependent kinase 4 inhibitor A modulator, an Estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, aTIM3 inhibitor, a GAL9 inhibitor, a LAG3 inhibitor, a VISTA inhibitor, a KIR inhibitor, a 2B4 inhibitor, a CD160 inhibitor, a CD66e modulator, an Angiotensin II receptor antagonist, a Connective tissue growth factor ligand inhibitor, a Jak1 tyrosine kinase inhibitor, a Jak2 tyrosine kinase inhibitor, a dual Jak1/Jak2 tyrosine kinase inhibitor, an Angiotensin converting enzyme 2 stimulator, a Growth hormone receptor antagonist, a Galectin-3 inhibitor, a Sodium glucose transporter-2 inhibitor, a Endothelin ET-A antagonist, a Mineralocorticoid receptor antagonist, an Endothelin ET-B antagonist, an Advanced glycosylation product receptor antagonist, an Adrenocorticotrophic hormone ligand, a Famesoid X receptor agonist, a G-protein coupled bile acid receptor 1 agonist, an Aldose reductase inhibitor, a Xanthine oxidase inhibitor, a PPAR gamma agonist, a Prostanoid receptor antagonist, a FGF receptor antagonist, a PDGF receptor antagonist, a TGF beta antagonist, a p38 MAP kinase inhibitor, a VEGF-1 receptor antagonist, a Protein tyrosine phosphatase beta inhibitor, a Tek tyrosine kinase receptor stimulator, a PDE 5 inhibitor, a Mineralocorticoid receptor antagonist, an ACE inhibitor, a I-kappa B kinase inhibitor, a NFE2L2 gene stimulator, a Nuclear factor kappa B inhibitor, a STAT3 gene inhibitor, a NADPH oxidase 1 inhibitor, a NADPH oxidase 4 inhibitor, a PDE 4 inhibitor, a Renin inhibitor, a MEKK-5 protein kinase inhibitor, a Membrane copper amine oxidase inhibitor, an Integrin alpha-V/beta-3 antagonist, an Insulin sensitizer, a Kallikrein 1 modulator, a Cyclooxygenase 1 inhibitor and a Phenylalanine hydroxylase stimulator.

In some embodiments, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, nab-paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX, KY-1003, olmesartan medoxomil, candesartan, PBI-4050, baricitinib, GSK-2586881, losartan, dapagliflozin propanediol, pegvisomant, GR-MD-02, canagliflozin, irbesartan, FG-3019, atrasentan, finerenone, sparsentan, bosentan, defibrotide, fimasartan, azeliragon, pyridoxamine, corticotropin, INT-767, epalrestat, topiroxostat. SER-150-DN, pirfenidone. VEGFR-1 mAb, AKB-9778, PF-489791, SHP-627, CS-3150, imidapril, perindopril, captopril, enalapril, lisinopril, Zofenopril, Lisinopril, Quinapril, Benazepril, Trandolapril, Cilazapril, Fosinopril, Ramipril, bardoxolone methyl, irbesartan+propagermanium, GKT-831, MT-3995, TAK-648, TAK-272, GS-4997, DW-1029M, ASP-8232, VPI-2690B, DM-199, rhein, PHN-033, GLY-230, and saproterin, sulodexide.

In some embodiments, the one or more additional therapeutic compound is an angiotensin converting enzyme (ACE) inhibitor or an angiotensin receptor II blocker (ARB). In some embodiments, the one or more additional therapeutic compound is an angiotensin converting enzyme (ACE) inhibitor. In some embodiments, the one or more additional therapeutic compound is an angiotensin receptor II blocker (ARB). In some embodiments, the one or more additional therapeutic compound is olmesartan medoxomil, candesartan, losartan, irbesartan, sparsentan, fimasartan, GSK-2586881, imidapril, perindopril, captopril, enalapril, lisinopril, Zofenopril, Lisinopril, Quinapril, Benazepril, Trandolapril, Cilazapril, Fosinopril or Ramipril.

In some embodiments, the one or more additional therapeutic compound is FOLFIRINOX. In some embodiments, the one or more additional therapeutic compound is gemcitabine and paclitaxel. In some embodiments, the one or more additional therapeutic compound is gemcitabine and nab-paclitaxel.

Compounds that Modulate CCR2 Activity

The present invention provides compounds that modulate at least one CCR2 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR2 and a CCR2 ligand, such as MCP-1. Compounds contemplated by the invention include, but are not limited to, the exemplary compounds provided herein and salts thereof.

For example, compounds of this invention act as potent CCR2 antagonists, and this antagonistic activity has been further confirmed in animal testing for inflammation, one of the hallmark disease states for CCR2. Accordingly, the compounds provided herein are useful in pharmaceutical compositions, methods for the treatment of CCR2-mediated diseases, and as controls in assays for the identification of competitive CCR2 antagonists.

Methods of Treatment

Modulation of CCR2 Receptor Function

The compounds of the invention may be used as agonists, (preferably) antagonists, partial agonists, inverse agonists, of CCR2 receptors in a variety of contexts, both in vitro and in vivo. In one embodiment, the compounds of the invention are CCR2 antagonists that can be used to inhibit the binding of CCR2 receptor ligand to the CCR2 receptor in vitro or in vivo. In general, such methods comprise the step of contacting a CCR2 receptor with a sufficient amount of one or more CCR2 receptor modulators as provided herein, in the presence of CCR2 receptor ligand in aqueous solution and under conditions otherwise suitable for binding of the ligand to CCR2 receptor. The CCR2 receptor may be present in suspension (e.g., in an isolated membrane or cell preparation), in a cultured or isolated cell, or in a tissue or organ.

Preferably, the amount of CCR2 receptor modulator contacted with the receptor should be sufficient to inhibit ligand binding to the CCR2 receptor in vitro as measured, for example, using a radioligand binding assay, calcium mobilization assay, or chemotaxis assay as described herein.

In one embodiment of the invention, the CCR2 modulators of the invention are used to modulate, preferably inhibit, the signal-transducing activity of a CCR2 receptor, for example, by contacting one or more compound(s) of the invention with a CCR2 receptor (either in vitro or in vivo) under conditions suitable for binding of the modulator(s) to the receptor. The receptor may be present in solution or suspension, in a cultured or isolated cell preparation or within a patient. Any modulation of the signal transducing activity may be assessed by detecting an effect on calcium ion calcium mobilization or by detecting an effect on CCR2 receptor-mediated cellular chemotaxis. In general, an effective amount of CCR2 modulator(s) is an amount sufficient to modulate CCR2 receptor signal transducing activity in vitro within a calcium mobilization assay or CCR2 receptor-mediated cellular chemotaxis within a migration assay.

When compounds of the invention are used to inhibit CCR2 receptor-mediated cellular chemotaxis, preferably leukocyte chemotaxis, in an in vitro chemotaxis assay, such methods comprise contacting white blood cells (particularly primate white blood cells, especially human white blood cells) with one or more compounds of the invention. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound of the invention has been added.

In another embodiment, the compounds of the present invention further can be used for treating patients suffering from conditions that are responsive to CCR2 receptor modulation. As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). As used herein, a condition is considered "responsive to CCR2 receptor modulation" if modulation of CCR2 receptor activity results in the reduction of inappropriate activity of a CCR2 receptor. As used herein, the term "patients" include primates (especially humans), domesticated companion animals (such as dogs, cats, horses, and the like) and livestock (such as cattle, pigs, sheep, and the like), with dosages as described herein.

In some embodiments, the compounds of the present invention further can be used for treating patients suffering from an inflammatory disease or disorder, a cardiovascular or cerebrovascular disorder, an autoimmune disorder, a cancer or a solid tumor. In some embodiments, the compounds of the present invention can be used for treating patients suffering from a disease or disorder selected from the group consisting of diabetic nephropathy, nephropathy, neutropenia, neutrophilia, Albuminuria, Diabetic retinopathy, Focal segmental glomerulosclerosis, glomerulosclerosis, Allergy, fibrosis, NASH (Nonalcoholic Steatohepatitis), Hemolytic uremic syndrome, atypical hemolytic uremic syndrome (aHUS), C3-glomerulopathy, C3-glomerulonephritis, dense deposit disease, membranoproliferative glomerulonephritis, sepsis, septic shock, Alzheimer's disease, multiple sclerosis, stroke, inflammatory bowel disease, chronic obstructive pulmonary disorder, inflammation associated with burns, lung injury, osteoarthritis, atopic dermatitis, chronic urticaria, ischemia-reperfusion injury, acute respiratory distress syndrome, systemic inflammatory response syndrome, multiple organ dysfunction syndrome, tissue graft rejection, Graft versus host disease, hyperacute rejection of transplanted organs, myocardial infarction, coronary thrombosis, vascular occlusion, post-surgical vascular reocclusion, artherosclerosis, traumatic central nervous system injury, ischemic heart disease, rheumatoid arthritis, systemic lupus erythematosus, Guillain-Barre syndrome, pancreatitis, lupus nephritis, lupus glomerulonephritis, psoriasis, Crohn's disease, vasculitis, Anca-vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome, immunovasculitis, tissue graft rejection, hyperacute rejection of transplanted organs, Melanoma, Small Cell Lung Carcinoma, Non Small Cell Lung Carcinoma, Pancreatic Cancer, Breast Cancer, Bladder Cancer, Renal Cell Carcinoma, Colorectal Cancer, Hepatocellular Carcinoma, Head and Neck Squamous Cell Carcinoma, Esophageal Cancer, Ovarian Cancer, Prostate Cancer, Gastric Cancer, Acute myelogenous leukemia, leukemia, a pathologic sequelae associated with the group consisting of insulin-dependent diabetes, mellitus, lupus nephropathy, Heyman nephritis, membranous nephritis, glomerulonephritis, contact sensitivity responses, and inflammation resulting from contact of blood with artificial surfaces.

In some embodiments, the compounds of the present invention can be used for treating patients suffering from a disease or disorder and are administered with one or more additional therapeutic compound. In some embodiments, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a Thymidylate synthase inhibitor, an EGFR tyrosine kinase receptor inhibitor, an Epidermal growth factor antagonist, a Fyn tyrosine kinase inhibitor, a Kit tyrosine kinase inhibitor, a Lyn tyrosine kinase inhibitor, a NK cell receptor modulator, a PDGF receptor antagonist, a PARP inhibitor, a Poly ADP ribose polymerase inhibitor, a Poly ADP ribose polymerase 1 inhibitor, a Poly ADP ribose polymerase 2 inhibitor, a Poly ADP ribose polymerase 3 inhibitor, a Galactosyltransferase modulator, a Dihydropyrimidine dehydrogenase inhibitor, an Orotate phosphoribosyltransferase inhibitor, a Telomerase modulator, a Mucin 1 inhibitor, a Mucin inhibitor, a Secretin agonist, a TNF related apoptosis inducing ligand modulator, an IL17 gene stimulator, an Interleukin 17E ligand, a Neurokinin receptor agonist, a Cyclin GI inhibitor, a checkpoint inhibitor, a PD-1 inhibitor, a PD-L1 inhibitor, a CTLA4 inhibitor, a Topoisomerase I inhibitor, an Alk-5 protein kinase inhibitor, a Connective tissue growth factor ligand inhibitor, a Notch-2 receptor antagonist, a Notch-3 receptor antagonist, a Hyaluronidase stimulator, a MEK-1 protein kinase inhibitor; MEK-2 protein kinase inhibitor, a GM-CSF receptor modulator; TNF alpha ligand modulator, a Mesothelin modulator, an Asparaginase stimulator, a Caspase-3 stimulator; Caspase-9 stimulator, a PKN3 gene inhibitor, a Hedgehog protein inhibitor; Smoothened receptor antagonist, an AKT1 gene inhibitor, a DHFR inhibitor, a Thymidine kinase stimulator, a CD29 modulator, a Fibronectin modulator, an Interleukin-2 ligand, a Serine protease inhibitor, a D40LG gene stimulator; TNFSF9 gene stimulator, a 2 oxoglutarate dehydrogenase inhibitor, a TGF-beta type II receptor antagonist, an Erbb3 tyrosine kinase receptor inhibitor, a Cholecystokinin CCK2 receptor antagonist, a Wilms tumor protein modulator, a Ras GTPase modulator, an Histone deacetylase inhibitor, a Cyclin-dependent kinase 4 inhibitor A modulator, an Estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, aTIM3 inhibitor, a GAL9 inhibitor, a LAG3 inhibitor, a VISTA inhibitor, a KIR inhibitor, a 2B4 inhibitor, a CD160 inhibitor, a CD66e modulator, an Angiotensin II receptor antagonist, a Connective tissue growth factor ligand inhibitor, a Jak1 tyrosine kinase inhibitor, a Jak2 tyrosine kinase inhibitor, a dual Jak1/Jak2 tyrosine kinase inhibitor, an Angiotensin converting enzyme 2 stimulator, a Growth hormone receptor antagonist, a Galectin-3 inhibitor, a Sodium glucose transporter-2 inhibitor, a Endothelin ET-A antagonist, a Mineralocorticoid receptor antagonist, an Endothelin ET-B antagonist, an Advanced glycosylation product receptor antagonist, an Adrenocorticotrophic hormone ligand, a Farnesoid X receptor agonist, a G-protein coupled bile acid receptor 1 agonist, an Aldose reductase inhibitor, a Xanthine oxidase inhibitor, a PPAR gamma agonist, a Prostanoid receptor antagonist, a FGF receptor antagonist, a PDGF receptor antagonist, a TGF beta antagonist, a p38 MAP kinase inhibitor, a VEGF-1 receptor antagonist, a Protein tyrosine phosphatase beta inhibitor, a Tek tyrosine kinase receptor stimulator, a PDE 5 inhibitor, a Mineralocorticoid receptor antagonist, an ACE inhibitor, a I-kappa B kinase inhibitor, a NFE2L2 gene stimulator, a Nuclear factor kappa B inhibitor, a STAT3 gene inhibitor, a NADPH oxidase 1 inhibitor, a NADPH oxidase 4 inhibitor, a PDE 4 inhibitor, a Renin inhibitor, a MEKK-5 protein kinase inhibitor, a Membrane copper amine oxidase inhibitor, an Integrin alpha-V/beta-3 antagonist, an Insulin sensitizer, a Kallikrein 1 modulator, a Cyclooxygenase 1 inhibitor and a Phenylalanine hydroxylase stimulator. In some embodiments, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, camptothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, nab-paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX, KY-1003, olmesartan medoxomil, candesartan, PBI-4050, baricitinib, GSK-2586881, losartan, dapagliflozin propanediol, pegvisomant, GR-MD-02, canagliflozin, irbesartan, FG-3019, atrasentan, finerenone, sparsentan, bosentan, defibrotide, fimasartan, azeliragon, pyridoxamine, corticotropin, INT-767, epalrestat, topiroxostat, SER-150-DN, pirfenidone, VEGFR-1 mAb, AKB-9778, PF-489791, SHP-627, CS-3150, imidapril, perindopril, captopril, enalapril, lisinopril, Zofenopril, Lisinopril, Quinapril, Benazepril, Trandolapril, Cilazapril, Fosinopril, Ramipril, bardoxolone methyl, irbesartan+propagermanium, GKT-831. MT-3995, TAK-648, TAK-272, GS-4997, DW-1029M, ASP-8232, VPI-2690B. DM-199, rhein, PHN-033, GLY-230, and saproperin, sulodexide.

In some embodiments, the one or more additional therapeutic compound is an angiotensin converting enzyme (ACE) inhibitor or an angiotensin receptor II blocker (ARB). In some embodiments, the one or more additional therapeutic compound is an angiotensin converting enzyme (ACE) inhibitor. In some embodiments, the one or more additional therapeutic compound is an angiotensin receptor II blocker (ARB). In some embodiments, the one or more additional therapeutic compound is olmesartan medoxomil, candesartan, losartan, irbesartan, sparsentan, fimasartan, GSK-2586881, imidapril, perindopril, captopril, enalapril, lisinopril, Zofenopril, Lisinopril, Quinapril, Benazepril, Trandolapril, Cilazapril. Fosinopril or Ramipril.

In some embodiments, the one or more additional therapeutic compound is FOLFIRINOX. In some embodiments, the one or more additional therapeutic compound is gemcitabine and paclitaxel. In some embodiments, the one or more additional therapeutic compound is gemcitabine and nab-paclitaxel. Conditions that can be treated by CCR2 modulation:

Autoimmune disorders—e.g., Rheumatoid arthritis, systemic lupus erythematosus, Guillain-Barre syndrome, pancreatitis, lupus nephritis, lupus glomerulonephritis, psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, hyperacute rejection of transplanted organs; and the like.

Inflammatory disorders and related conditions—e.g., Neutropenia, sepsis, septic shock, Alzheimer's disease, multiple sclerosis, stroke, inflammatory bowel disease (IBD), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. Compounds of the instant invention may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a compound of the invention may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Diseases of Vasculitis—Vasculitic diseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The compounds provided in the present invention can be used to treat leukoclastic vasculitis, Wegener's granulomatosis, microscopic polyangiitis, Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

Cancer—CCR2 and its ligand CCL2 also play a major role in conditioning the tumor microenvironment, and regulating the influx of both beneficial and deleterious immune cell populations to the tumor. As such recent clinical and pre-clinical literature has demonstrated a role for CCR2 in a variety of solid tumors including Melanoma, Small Cell Lung Carcinoma, Non Small Cell Lung Carcinoma, Pancreatic Cancer, Breast Cancer, Bladder Cancer, Renal Cell Carcinoma, Colorectal Cancer, Hepatocellular Carcinoma, Head and Neck Squamous Cell Carcinoma, Esophageal Cancer, Ovarian Cancer, Prostate Cancer, and Gastric Cancer.

HIV infection, AIDS and Viral Infections—CCR2 receptor modulators provided herein may be used to inhibit HIV infection, delay AIDS progression or decrease the severity of symptoms or HIV infection and AIDS, as well as in the treatment of hepatitis C.

Neurodegenerative disorders and related diseases—Within further aspects, CCR2 antagonists provided herein may be used to treat Alzheimer's disease, multiple sclerosis, and cognitive function decline associated with cardiopulmonary bypass surgery and related procedures.

In one embodiment of the invention, the compounds of the invention can be used for the treatment of diseases selected from the group consisting of sepsis (and associated disorders), COPD, rheumatoid arthritis, lupus nephritis and multiple sclerosis.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the invention are preferably administered to a patient (e.g., a human) orally or topically. The effective amount may be an amount sufficient to modulate CCR2 receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present invention also contemplates administration of the compounds and compositions of the present invention in a depot formulation.

Dosage levels of the order of from about 0.1 mg to about 140 mg per kilogram of body weight per day are useful in the treatment or preventions of conditions involving pathogenic CCR2 activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravenously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In some embodiments, the treatment or prevention of conditions which require CCR2 receptor modulation, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

Combination Treatments—Pharmacologics to be Used in Conjunction with CCR2 Compounds Pharmacological agents that can be used in conjunction with the CCR2 antagonists of the current invention include those used for the treatments of atherosclerosis, restenosis, multiple sclerosis, pulmonary fibrosis, inflammatory bowel disease, rheumatoid arthritis, graft-versus-host disease, renal fibrosis, psoriasis, transplantation rejection, obesity, diabetes, hypercholesterolemia and cancer.

In the treatment of cancer, immune modulators such as those of the invention may be used in conjunction with other compounds and reagents which regulate the immune response or tumor immune environment. This is termed "immuno-oncology", and a wide variety of reagents can be utilized either alone or in combinations, including small molecules, protein and peptides, antibodies, speigelmers, viruses, oligoribonucleotides and other methods of genetic information delivery and other therapeutics known in the art. As such compositions of the invention can be utilized in the formulation of immunoimmune-oncologic medicaments.

In still other embodiments, the present methods are directed to the treatment of allergic diseases, wherein a compound or composition of the invention is administered either alone or in combination with a second therapeutic agent, wherein said second therapeutic agent is an antihistamine. When used in combination, the practitioner can administer a combination of the compound or composition of the present invention and a second therapeutic agent. Also, the compound or composition and the second therapeutic agent can be administered sequentially, in any order.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

In treating, preventing, ameliorating, controlling or reducing solid tumour growth and metastases, the compounds of the present invention may be used in conjunction with the following: (1) cancer vaccination strategies, (2) immune-checkpoint modulators such as antagonistic antibodies against immune-checkpoint inhibitors (anti-PD1, anti-PD-L1, anti-CTLA4, anti-Tim3, anti-VISTA, anti-KIR) or agonistic antibodies against immune-accelerators (anti-Lag3, anti-OX40, anti-ICOS, anti-4-1BB, (3) blocking or depleting antibodies against cell surface proteins commonly up-regulated in transformed cells (CEACAM1, Syndecan-2, GRP78), (4) anti-angiogenic therapies (anti-VEGF, anti-VEGFR, VEGFR small molecule inhibitors), (5) anti-lymphangiogenesis (blocking antibodies or inhibitors against VEGF, FDF2, PDGF as well as its respective receptors), (6) standard chemotherapeutic therapies (Gemcitabine, Paclitaxel, FOLFORINOX), (7) irradiation therapy, (8) other chemokine antagonists (CCR1, CCR4, CCR6, CXCR4, CXCR2, CXCR7 small molecule inhibitors, blocking antibodies, or depleting antibodies), (9) depleting antibodies against chemokines that activate the aforementioned chemokine receptors, (10) inhibitors targeting common somatic mutations in cancer such as those specifically targeting the following genes (BRAF, KRAS, NRAS, EGFR, CTNNB1, NOTCH1, PIK3CA, PTEN, APC, FLT3, IDH1, IDH2, KIT, TP53, JAK2).

In treating, preventing, ameliorating, controlling or reducing the risk of inflammation, the compounds of the present invention may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing anti-inflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like.

Similarly, the compounds of the present invention may be administered with a pain reliever; a potentiator such as caffeine, an H2-antagonist, simethicone, aluminum or magnesium hydroxide; a decongestant such as pseudophedrine; an antitussive such as codeine; a diuretic; a sedating or non-sedating antihistamine; a very late antigen (VLA-4) antagonist; an immunosuppressant such as cyclosporin, tacrolimus, rapamycin, EDG receptor agonists, or other FK-506 type immunosuppressants; a steroid; a non-steroidal anti-asthmatic agent such as a β2-agonist, leukotriene antagonist, or leukotriene biosynthesis inhibitor; an inhibitor of phosphodiesterase type IV (PDE-IV); a cholesterol lowering agent such as a HMG-CoA reductase inhibitor, sequestrant, or cholesterol absorption inhibitor; and an anti-diabetic agent such as insulin, α-glucosidase inhibitors or glitazones.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In view of the above, a number of selected embodiments are provided herein.

In one embodiment, the present invention provides a method of treating a CCR2-mediated condition or disease involving administering to a subject a safe and effective amount of the compound or composition of the invention, where the CCR2-mediated condition or disease is atherosclerosis.

In one embodiment, the present invention provides a method of treating a CCR2-mediated condition or disease involving administering to a subject a safe and effective amount of the compound or composition of the invention, where the CCR2-mediated condition or disease is restenosis.

In one embodiment, the present invention provides a method of treating a CCR2-mediated condition or disease involving administering to a subject a safe and effective amount of the compound or composition of the invention, where the CCR2-mediated condition or disease is multiple sclerosis.

In one embodiment, the present invention provides a method of treating a CCR2-mediated condition or disease involving administering to a subject a safe and effective amount of the compound or composition of the invention, where the CCR2-mediated condition or disease is selected from the group consisting of inflammatory bowel disease, renal fibrosis, rheumatoid arthritis, obesity and noninsulin-dependent diabetes.

In one embodiment, the present invention provides a method of treating a CCR2-mediated condition or disease involving administering to a subject a safe and effective amount of the compound or composition of the invention, where the CCR2-mediated condition or disease is type 2 diabetes.

In one embodiment, the present invention provides a method of treating a CCR2-mediated condition or disease involving administering to a subject a safe and effective amount of the compound or composition of the invention, where the CCR2-mediated condition or disease is diabetic nephropathy.

In one embodiment, the present invention provides a method of treating a CCR2-mediated condition or disease involving administering to a subject a safe and effective amount of the compound or composition of the invention, where the CCR2-mediated condition or disease is pancreatic cancer In one embodiment, the present invention provides a method of treating a CCR2-mediated condition or disease involving administering to a subject a safe and effective amount of the compound or composition of the invention, where the CCR2-mediated condition or disease is a cancer or immunoimmune-oncology related indication.

In one embodiment, the present invention provides a method of treating a CCR2-mediated condition or disease involving administering to a subject a safe and effective amount of the compound or composition of the invention, where the CCR2-mediated condition or disease is selected from the group consisting of chronic obstructive pulmonary disease, idiopathic pulmonary fibrosis and idiopathic pneumonia syndrome.

In one embodiment, the present invention provides a method of treating a CCR2-mediated condition or disease involving administering to a subject a safe and effective amount of the compound or composition of the invention, where the administering is oral, parenteral, rectal, transdermal, sublingual, nasal or topical.

In one embodiment, the present invention provides a method of treating a CCR2-mediated condition or disease involving administering to a subject a safe and effective amount of the compound or composition of the invention, where the compound is administered in combination with an anti-inflammatory or analgesic agent.

In one embodiment, the present invention provides a method of treating a CCR2-mediated condition or disease involving administering to a subject a safe and effective amount of the compound or composition of the invention, where an anti-inflammatory or analgesic agent is also administered.

In one embodiment, the present invention provides a method of modulating CCR2 function in a cell, where the CCR2 function in the cell is modulated by contacting the cell with a CCR2 modulating amount of the compound of the present invention.

In one embodiment, the present invention provides a method of treating a CCR2-mediated condition or disease involving administering to a subject a safe and effective amount of the compound or composition of the invention, where the disease is selected from the group consisting of pulmonary fibrosis, transplantation rejection, graft-versus-host disease and cancer.

In yet other embodiments, the present methods are directed to the treatment of psoriasis wherein a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

In yet another aspect of the invention, the compounds of the invention can be used in a variety of non-pharmaceutical in vitro and in vivo application. For example, the compounds of the invention may be labeled and used as probes for the detection and localization of CCR2 receptor (cell preparations or tissue sections samples). The compounds of the invention may also be used as positive controls in assays for CCR2 receptor activity, i.e., as standards for determining the ability of a candidate agent to bind to CCR2 receptor, or as radiotracers for positron emission tomography (PET) imaging or for single photon emission computerized tomography (SPECT). Such methods can be used to characterize CCR2 receptors in living subjects. For example, a CCR2 receptor modulator may be labeled using any of a variety of well known techniques (e.g., radiolabeled with a radionuclide such as tritium), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of CCR2 receptor in the sample. Detection assays, including receptor autoradiography (receptor mapping) of CCR2 receptor in cultured cells or tissue samples may be performed as described by Kuhar in sections 8.1.1 to 8.1.9 of Current Protocols in Pharmacology (1998) John Wiley & Sons, New York.

The compounds provided herein may also be used within a variety of well known cell separation methods. For example, modulators may be linked to the interior surface of a tissue culture plate or other support, for use as affinity ligands for immobilizing and thereby isolating, CCR2 receptors (e.g., isolating receptor-expressing cells) in vitro. In one preferred application, a modulator linked to a fluorescent marker, such as fluorescein, is contacted with the cells, which are then analyzed (or isolated) by fluorescence activated cell sorting (FACS).

In FIG. 1, structures and activity are provided for representative compounds described herein. Activity is provided as follows for the binding assay as described herein: +, 501 nM≤IC50<5000 nM; ++, 101 nM≤IC50<500 nM; and +++, 1 nM≤IC50≤100 nM.

V. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:

aq: aqueous; BBr$_3$: boron tribromide; CH$_2$Cl$_2$ or DCM: dichloromethane; CH$_3$CN: acetonitrile; CH$_3$OH or MeOH: methanol; DAST, (Diethylamino)sulfur trifluoride: DavePhos, 2-Dicyclohexylphosphino-2'-(N,N-dimethylamino) biphenyl; 1,2-DCE, 1,2-dichloroethane; DIEA: N,N-diisopropylethylamine; DMF: dimethyl formamide; DMP, Dess-Martin periodinane; DMSO: dimethyl sulfoxide; equiv. or eq.: equivalents; Et$_3$N: triethylamine; Et$_2$O: diethyl ether; EtOH: ethanol; EtONa, sodium ethoxide; h: hour(s); HATU, O-(7-Azabenzotriazol-1-yl)-N,N,N',N'-tetramethyluronium hexafluorophosphate; HCl: hydrogen chloride; H$_2$O: water; K$_2$CO$_3$: potassium carbonate; KHSO$_4$: potassium bisulfate; LAH, lithium aluminum hydride; LDA, lithium diisopropylamide; MgSO$_4$: magnesium sulfate; mL: milliliter; NaCl: sodium chloride; NaH: sodium hydride; NaHCO$_3$: sodium bicarbonate; NaOEt: sodium ethoxide; NaOH: sodium hydroxide; NaOMe: sodium methoxide; Na$_2$SO$_4$: sodium sulfate; NH$_4$Cl: ammonium chloride; NMP: N-methyl pyrrolidinone; pH: −log [H$^+$]; POCl$_3$, phosphoryl trichloride; PPTS, pyridinium p-toluenesulfonate; RP-HPLC, reversed phase high pressure liquid chromatography; RT, room temperature; TEA, triethylamine; TFA: trifluoroacetic acid; TFAA, trifluoroacetic anhydride; THF: tetrahydrofuran; TLC: thin layer chromatography Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

EXAMPLES

Example 1

Synthesis of [(2S,5S)-5-[4-(4-fluorophenyl)-1-piperidyl]-2-methyl-tetrahydropyran-2-yl]-[3-(trifluoromethyl)-7,8-dihydro-5H-1,6-naphthyridin-6-yl]methanone and [(2R,5R)-5-[4-(4-fluorophenyl)-1-piperidyl]-2-methyl-tetrahydropyran-2-yl]-[3-(trifluoromethyl)-7,8-dihydro-5H-1,6-naphthyridin-6-yl]methanone

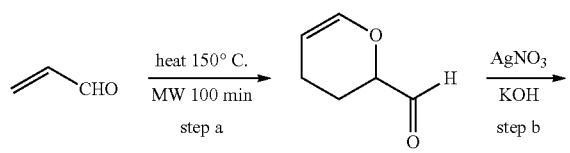

step a

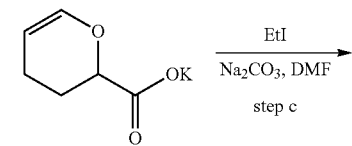

step c

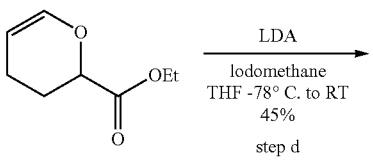

step d

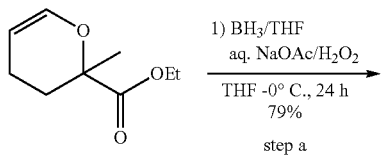

step a

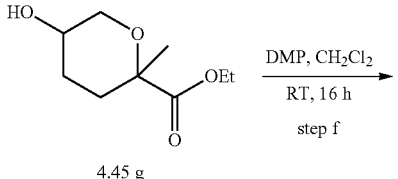

step f 4.45 g

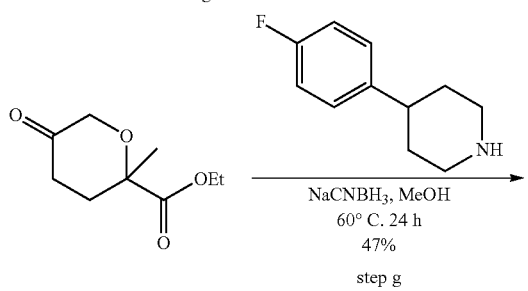

step g

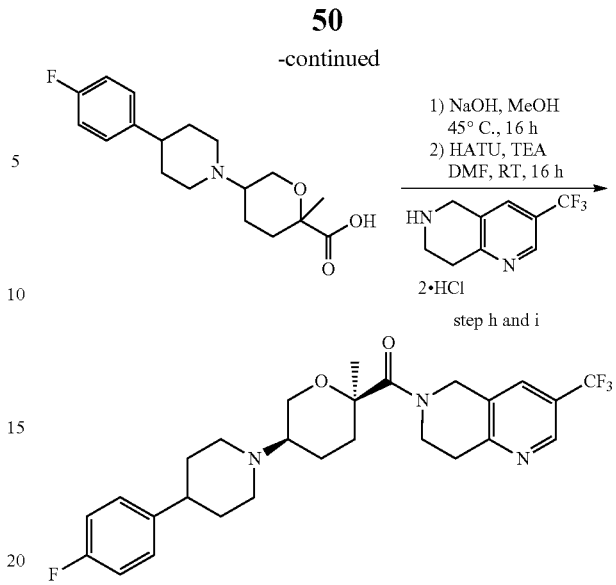

step h and i

Step a:

A microwave vial was charged with freshly distilled acrolein (40.0 g, 48.0 mL, 710 mmol) and hydroquinone (50 mg). The mixture was heated for 70 min at 140° C., then for 30 min at 150° C. Afterwards, the contents of the vial were filtered, washed with $CH_2Cl_2$ and concentrated under reduced pressure. The resulting 3,4-dihydro-2H-pyran-2-carboxaldehyde (20.0 g, 50%) was pure enough to be immediately used in the next step.

Step b:

A solution of $AgNO_3$ (65 g, 383 mmol) in water (400 mL) was added to a stirred solution of 3,4-dihydro-2H-pyran-2-carbaldehyde (13 g, 116 mmol) in ethanol (300 mL), followed by the slow addition of a solution of KOH (43 g, 766 mmol) in water (300 mL) over 1 hour. The mixture was filtered and evaporated. The residue was extracted with ether. The aqueous layer was adjusted to pH=3 with 6 N HCl and extracted with MTBE (2×200 mL). The organic layer was evaporated and the residue was treated with 1 N NaOH until the pH=12. The mixture was co-evaporated with methanol to dryness to give 3,4-dihydro-2H-pyran-2-carboxylicacid (8 g).

Step c:

To a stirred suspension of the carboxylic acid attained above, (8.0 g, 53.0 mmol) in DMF (70 mL) at rt was added $Na_2CO_3$ (5.0 g, 47.2 mmol) and ethyl iodide (9.9 g, 63.6 mmol). The reaction mixture was stirred for 6 h at 110° C. then allowed to cool to room temperature and diluted with $H_2O$ (100 mL). The crude product was extracted with $Et_2O$ (4×100 mL) and the combined organic layers were washed with brine, dried over $Na_2SO_4$, filtered and concentrated under reduced pressure to afford ethyl 3,4-dihydro-2H-pyran-2-carboxylate (5 g, 60%) as a yellow oil.

Step d:

To a cold (−78° C.) solution of ethyl 3,4-dihydro-2H-pyran-2-carboxylate (10.4 g, 66.6 mmol) in anhydrous THF (150 mL) was added a solution of LDA in THF (2.0 M, 40 mL, 80.0 mmol). The reaction mixture was stirred at −78° C. for 1 hour, treated with methyl iodide (16.6 mL, 266.4 mmol), stirred for 1 h at −78° C. and allowed to warm to room temperature. The reaction mixture was quenched with saturated aqueous ammonium chloride and extracted with ether (2×100 mL). The organic extract was washed with brine, dried over $Na_2SO_4$, filtered, and concentrated under vacuum to afford ethyl-3,4-dihydro-2-methyl-2H-pyran-2- carboxylate (5.1 g, 45%) as a colorless oil. ¹H-NMR (400 MHz, CDCl₃): δ 6.39 (dt, J=1.9 Hz, 1H), 4.73-4.69 (m, 1H), 4.21 (q, J=7.5 Hz, 2H), 2.23 (dt, J=1.9 Hz, 1H), 2.0-1.95 (m, 2H), 1.79-1.71 (m, 1H), 1.48 (s, 3H), 1.28 (t, J=7.1 Hz, 3H).

Step e:
To a stirred solution of ethyl-3,4-dihydro-2-methyl-2H-pyran-2-carboxylate (5.1 g, 30.0 mmol) in THF (50 mL) at 0° C. was added slowly BH₃ in THF (60 mL, 60.0 mmol, 1M solution). The reaction mixture was stirred at 0° C. for 4 h and the mixture was kept at 0° C. for 16 h. The mixture was then treated with NaOAc (7.98 g, 60.0 mmol) followed by H₂O₂ (14.0 mL, 70.0 mmol, 30% solution). The reaction mixture was stirred at 0° C. for 2 h, then allowed to warm to room temperature and quenched with saturated Na₂SO₃ solution. The mixture was extracted with EtOAc (2×100 mL) and the combined organic layers were washed with brine, dried over Na₂SO₄, filtered and concentrated under reduced pressure. The crude product was purified by column chromatography on silica gel, eluting with ethyl acetate-hexanes 10% to 60% ethyl acetate/hexane gradient to afford ethyl tetrahydro-5-hydroxy-2-methyl-2H-pyran-2-carboxylate (4.43 g, 79%) as a colorless viscous liquid.

Step f:
To a stirred solution of ethyl-tetrahydro-5-hydroxy-2-methyl-2H-pyran-2-carboxylate (4.4 g, 23.6 mmol) in CH₂Cl₂ (150 mL) at 0° C. was added Dess-Martin periodinane (15.0 g, 35.4 mmol). The reaction mixture was stirred at rt for 16 h. After completion of the reaction, the mixture was quenched with saturated Na₂S₂O₄ solution, then stirred for 30 min and the resulting mixture was extracted with CH₂Cl₂ (2×150 mL) and washed with aqueous NaHCO₃ solution and brine, dried over Na₂SO₄, filtered and concentrated under reduced pressure. The crude residue was triturated with hexanes and filtered to afford ethyl tetrahydro-2-methyl-5-oxo-2H-pyran-2-carboxylate (3.45 g).

Step g:
To a mixed solution of ethyl tetrahydro-2-methyl-5-oxo-2H-pyran-2-carboxylate (0.75 g, 4.07 mmol), 4-(4-fluorophenyl)piperidine (963 mg, 4.48 mmol), in CH₂Cl₂ (15 mL) was added Na(OAc)₃BH (27.8 g, 124.05 mmol) at rt. The reaction mixture was heated at 50° C. for 16 h. After completion of the reaction, the mixture was quenched with saturated NaHCO₃ solution. The resulting mixture was extracted with CH₂Cl₂ (2×150 mL) and washed with aqueous NaHCO₃ solution and brine, dried over Na₂SO₄, filtered and concentrated under reduced pressure. The crude product was purified by column chromatography on silica gel, eluting with ethyl acetate-hexanes 10% to 60% ethyl acetate/hexane gradient to afford ethyl-5-(4-(4-fluorophenyl) piperidin-1-yl)-tetrahydro-2-methyl-2H-pyran-2-carboxylate (1.2 g, 47%). MS: (ES) m/z calculated for C₂₀H₂₉FNO₃ [M+H]⁺ 350.2, found 350.2.

Step h:
To a stirred solution of ethyl-5-(4-(4-fluorophenyl) piperidin-1-yl)-tetrahydro-2-methyl-2H-pyran-2-carboxylate (1.2 g, 14.9 mmol) in MeOH (5 mL) at rt was added 4M NaOH (3.0 mL). The reaction mixture was heated at 80° C. for 16 h. After completion of the reaction, this was allowed to cool to rt and quenched with 2N HCl (3 mL), after which the pH=5. The aqueous solution was extracted with CHCl₃: iPrOH 3:1 (3×50 mL) and the combined organic layers were washed with brine, dried over Na₂SO₄, filtered and concentrated under reduced pressure. The crude compound (1.05 g) was recovered as a brown solid and carried to the next step without purification. MS: (ES) m/z calculated for C₁₁H₂₄FNO₃ [M+H]⁺ 321.2, found 321.2.

Step i:
5-(4-(4-Fluorophenyl)piperidin-1-yl)-tetrahydro-2-methyl-2H-pyran-2-carboxylic acid (150 mg, 0.467 mmol), 3-(trifluoromethyl)-5,6,7,8-tetrahydro-1,6-naphthyridine HCl (143 mg, 0.70 mmol), HATU (266 mg, 0.70 mmol) and diisopropylethylamine (300 mg, 2.33 mmol) were mixed in DMF (2.5 mL). The reaction mixture was stirred for 16 h. After completion of the reaction, the mixture was diluted with H₂O and the aqueous solution was extracted with EtOAc (2×25 mL). The combined organic layers were washed with brine, dried over Na₂SO₄, filtered and concentrated under reduced pressure. The crude product was purified by column chromatography on silica gel, eluting with ethyl acetate-hexanes (20-100%) to give a mixture of diastereomers, which was further purified on a preparative TLC plate (8:2 ethyl acetate:hexanes) to separate the diastereomers. The racemic cis isomer. [(2S,5S)-5-[4-(4-fluorophenyl)-1-piperidyl)]-2-methyl-tetrahydropyran-2-yl]-[3-(trifluoromethyl)-7,8-dihydro-5H-1,6-naphthyridin-6-yl]-methanone and [(2R,5R)-5-[4-(4-fluorophenyl)-1-piperidyl]-2-methyl-tetrahydropyran-2-yl]-[3-(trifluoromethyl)-7,8-dihydro-5H-1,6-naphthyridin-6-yl] methanone, (20 mg, 10%) was isolated as a white fluffy solid: ¹H NMR (400 MHz, MeOH-d₄) δ 8.71 (s, 1H), 8.04 (s, 1H), 7.23 (dd, J=7.4, 5.5 Hz, 2H), 7.04 (dd, J=8.6, 5.5 Hz, 2H), 5.35-5.25 (m, 1H), 5.05 (dd, J=18.4, Hz, 1H), 4.72-4.62 (m, 1H), 4.40-4.35 (m, 1H), 4.30-4.22 (m, 1H), 4.15-3.90 (m, 1H), 3.70-3.55 (m, 2H), 3.50-3.40 (m, 2H), 3.28-3.05 (m, 4H), 2.95-2.80 (m, 1H), 2.75-2.60 (m, 1H), 2.28-2.20 (m, 1H), 2.15-2.05 (m, 2H), 1.95-1.75 (m, 3H), 1.53 (s, 3H). MS: (ES) m/z calculated for C₂₇H₃₂F₄N₃O₂ [M+H]⁺ 506.2 found 506.2.

Synthesis of
(2S)-2-cyclopropyl-3,4-dihydropyran-2-carboxylic acid

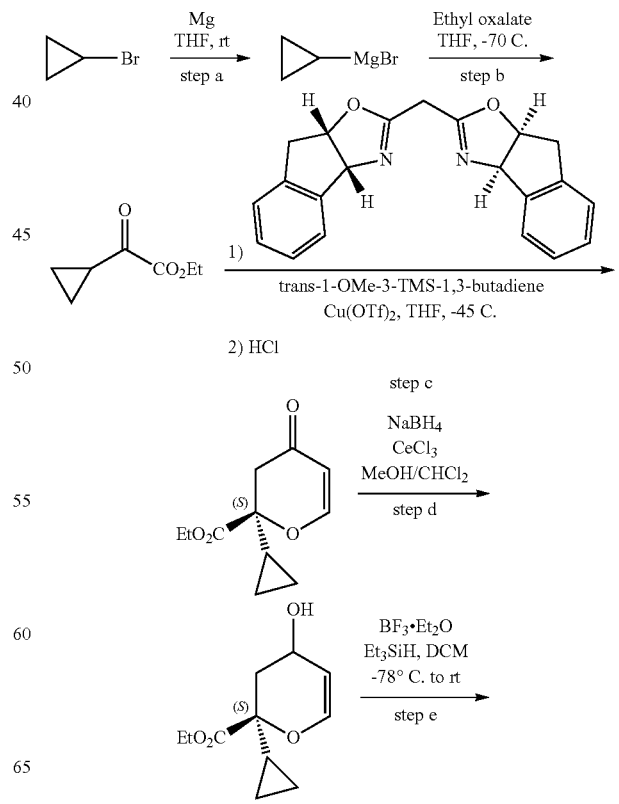

-continued

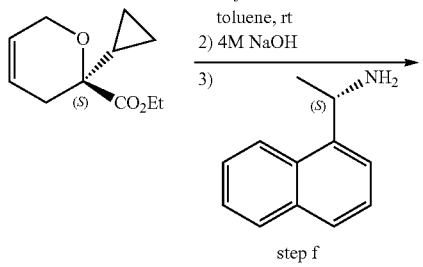

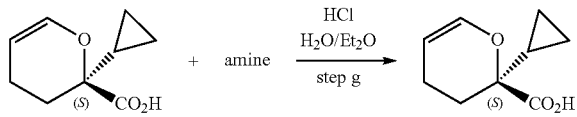

Step a:

A 5 L flask fitted with a magnetic stirrer was charged with Mg turnings (106 g, 4.34 mol, 1.58 equiv) and anhydrous THF (2.00 L) and purged with $N_2$. Mg was activated by addition of $Br_2$ (1 mL, 19.5 mmol) and stirring at rt for 15 min. A solution of cyclopropyl bromide (500 g, 4.13 mol, 1.5 equiv) in anhydrous THF (1.9 L) was added slowly over 2 h. The reaction was kept on ice during the addition and the rate controlled so the internal temperature was kept below 35° C. After addition the mixture was stirred at rt for 1.5 h then cooled on ice overnight. The next day the reaction was gently warmed to 22° C. to redissolve most of the precipitate and used in the following step.

Step b:

In a 12 L flask fitted with a mechanical stirrer (rinsed 1× with dry THF), diethyl oxalate (373 mL, 2.75 mol, 1 equiv) was dissolved in THF (1.00 L) and this solution was cooled in a reagent alcohol/dry ice bath. The Grignard solution from the first step was transferred via teflon cannula to the oxalate solution over the course of 3.5 h, keeping the internal temperature below −60° C. The Grignard flask was rinsed with THF (100 mL) and this was also transferred via Teflon cannula to the reaction mixture. After addition, the reaction was stirred for an additional 1.5 h, then quenched by adding an aqueous solution of $H_2SO_4$ (3M, 740 mL) until the pH ~2. The reaction was removed from the bath and allowed to warm to room temperature and stirred overnight. To the mixture was added brine (600 mL), $H_2O$ (500 mL), and hexanes (1.5 L). The mixture was stirred vigorously and the layers were separated. The aqueous layer was extracted with $Et_2O$ (2×400 mL), dried over $MgSO_4$, filtered and concentrated to give a brown oil. The oil was distilled under vacuum (~20 mmHg) to give a yellow oil (318 g, 88% pure by $^1H$ NMR) which was used in the next step.

Step c:

A 12 L, 3-neck flask equipped with a mechanical stirrer and internal thermometer was rinsed with anhydrous THF (3×) and charged with [3aR-[2(3'aR*,8'aS*), 3'aβ,8'aβ]]-(+)-2,2'-methylenebis[3a,8a-dihydro-8H-indeno[1,2-d]oxazole] (49.56 g, 0.15 mol, 0.055 equiv) and anhydrous THF (6 L) and 3A molecular sieves (500 g). The mixture was purged with $N_2$ for 5 min, then $Cu(OTf)_2$ was added. This mixture was stirred for 1 h then cooled in a reagent alcohol/dry ice bath. When the internal temperature reached −50° C. the ketone (467 g, 84% pure, 2.76 mol, 1 equiv) was added in THF (200 mL) over 15 min. After addition, the reaction mixture was stirred for 45 min, during which time the internal temperature reached −75° C. The diene (510 g, 2.96 mol, 1.07 equiv) in THF (200 mL) was added over 60 min, keeping the internal temperature below −67° C. The reaction was then stirred for 18 h in the −78° C. bath. The reaction was then removed from the bath and 1 M HCl in brine (3 L, 3.00 mol) was added and the reaction was allowed to stir for 2 h. Hexanes (1 L) was added and the layers were then separated. The aqueous layer was extracted with MTBE (750 mL) and the combined organic layers were washed with brine (750 mL), dried over $MgSO_4$ and filtered through celite. The filtrate was concentrated to give a dark brown oil (867 g). The oil was dissolved in acetone (1 L) and then MTBE (2 L) was added at which point a precipitate formed. This mixture was filtered through celite and concentrated. The product was then dissolved in MeCN (1 L) and washed with hexanes (3×400 mL). The combined hexanes were extracted with MeCN (200 mL) and the combined MeCN was then concentrated to give the product as a dark brown oil (715 g, 86% ee). The enantiopurity was established by HPCL using a Pirkle Covalent (R,R) Whelk-01 5/100 Kromasil chiral column (30:70 iPrOH:hexanes as eluent at 1 mL/min, $t_R$(major)=8.4 min and $t_R$ (minor)=10.6 min).

Step d:

A 12 L 3-neck flask equipped with a mechanical stirrer and internal thermometer was charged with $CeCl_3.7H_2O$ (514 g, 1.38 mol, 0.5 equiv) and MeOH (2.2 L). Once all solids dissolved, the mixture was cooled to 0° C. and crude intermediate 1 (714 g, 2.76 mol, 1 equiv)) in $CH_2Cl_2$ (2.2 L) was added. When the mixture reached an internal temperature of 5° C., solid $NaBH_4$ (124 g, 3.28 mol, 1.2 equiv) was added portionwise (10 g per portion) keeping the internal temperature below 16° C. After addition, the bath was removed. $H_2O$ (3 L) was added slowly, then 1 M citric acid (2.2 L). The layers were separated and the aqueous was extracted with $CH_2Cl_2$ (3×500 mL). The combined organic was washed with 1:1 $H_2O$:brine (600 mL), then dried over $MgSO_4$, filtered and concentrated. The product was recovered as a dark oil (598 g) containing 15 mol % $CH_2Cl_2$ and was kept in the freezer overnight. This was used in the next reaction the following day without further purification.

Step e:

In a 12 L, 3-necked flask equipped with mechanical stirrer and an addition funnel, the product of the previous step (598 g, 92% pure, 2.59 mol) was dissolved in $CH_2Cl_2$ (4 L) and cooled in a reagent alcohol/dry ice bath. When the internal temperature reached −75° C., $Et_3SiH$ (497 mL, 3.11 mol, 1.2 equiv.) was added and stirred for 5 min. Then $BF_3.Et_2O$ (384 mL, 3.11 mol, 1.2 equiv.) in $CH_2Cl_2$ (768 mL) was added dropwise over 1.25 hour, keeping the internal temperature below −68° C. Cooling bath was removed and the reaction was stirred for 1.5 h, after which time the internal temperature reached 2° C. The reaction was diluted with $H_2O$ (1 L) and carefully quenched with saturated $NaHCO_3$ (2.5 L). The reaction was stirred at rt for 20 min then the organic layer was separated, and the aqueous layer was extracted with $CH_2Cl_2$ (500 mL). The combined organics were dried over $MgSO_4$, filtered and concentrated to give crude product (558 g, >100%), which was used as is in the next step.

Step f:

In a 5 L, 1-necked flask equipped with magnetic stirrer, crude starting material (2.59 mol) was dissolved in toluene (2.59 L) and $N_2$ was bubbled through the solution for 20 min. $Et_3SiH$ (414 mL, 2.59 mol) was added followed by the Wilkinson's catalyst (43.1 g, 47 mmol, 0.018 equiv). $N_2$ was bubbled through the reaction for 5 more min, then the mixture was stirred at rt overnight. The reaction was evaporated. 4M NaOH (1.13 L, 4.53 mol, 1.75 equiv.) in MeOH:$H_2O$ (1:1) was added and the mixture was stirred at 70° C.

for 1 h. The reaction was concentrated in vacuo to ~50% of the initial volume and neutralized to pH=1-2 using 2M NaHSO$_4$. The dark brown mixture was extracted with EtOAc (3×1.0 L). The combined organics were dried over MgSO$_4$ and filtered. The solution was diluted with EtOAc to 9.0 L total volume. The solution was stirred vigorously while (S)-1-(1-naphthyl)ethyl amine (314 g, 1.83 mol, 0.7 equiv) in EtOH (150 mL) was added. Immediately a white solid precipitates and the mixture was stirred for 2 h then filtered, rinsing the solid with EtOAc (500 mL). This was dried under vacuum to give the product as a tan solid (456 g, 88% ee). To the solid was added 10 L MeCN, and this was refluxed for 1 h. The reaction was filtered to give the product as an off-white solid (428 g, 91% ee). To the solid was added MeCN (6.8 L) and H$_2$O (270 mL) and the mixture was refluxed for 9 h. This was allowed to cool to room temperature. Filtered the solid, rinsing with MeCN. This was dried in a vacuum oven to give the product as an off-white solid (352 g, >98%/0 ee).

Step g:

To the salt obtained above (46.0 g, 136 mmol, 1.0 equiv) was added Et$_2$O (500 mL) and 0.5 M aqueous HCl (326 mL, 163 mmol, 1.2 equiv). The mixture was stirred until the acid had completely dissolved and the layers were then separated. The aqueous was extracted with Et$_2$O (2×350 mL). The combined organic was then dried over MgSO$_4$, filtered, and concentrated to give the free acid which was used without purification.

Synthesis of benzyl (2S)-2-cyclopropyl-5-oxo-tetrahydropyran-2-carboxylate

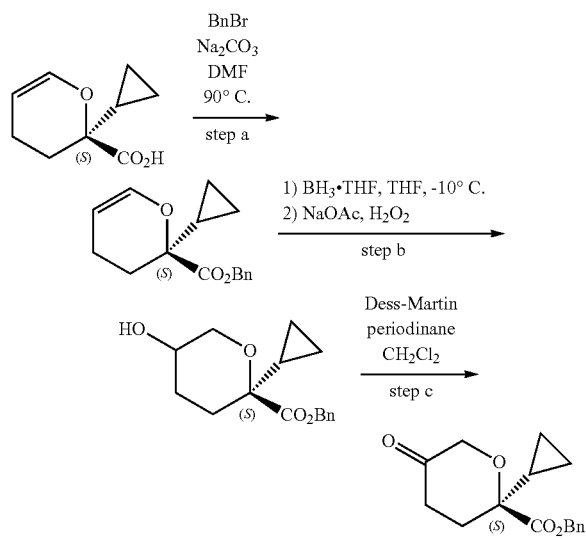

Step a:

To (2S)-2-cyclopropyl-3,4-dihydro-2H-pyran-2-carboxylic acid (5.4 g, 32.1 mmol, 1 equiv) dissolved in DMF (70 mL) was added Na$_2$CO$_3$ (5.1 g, 48.1 mmol, 1.5 equiv). This was stirred at 50° C. for 5 min, then benzyl bromide (4.6 mL, 38.5 mmol, 1.2 equiv) was added and the reaction was stirred at 90° C. for 3 h. The reaction was allowed to cool to room temperature, then diluted with H$_2$O (150 mL) and extracted with Et$_2$O (100 mL then 2×50 mL). The combined organic was dried over MgSO$_4$, filtered and concentrated to give the product as a yellow oil (8.3 g).

Step b:

(2S)-2-Cyclopropyl-3,4-dihydro-2H-pyran-2-carboxylic acid benzyl ester (8.3 g, 32 mmol, 1 equiv) was dissolved in THF (100 mL) and cooled in a brine/ice bath. BH$_3$.THF (1M in THF, 32 mL, 32 mmol, 1 equiv) was added dropwise over 5 min. The reaction was kept in an 8° C. refrigerator overnight, then returned to a brine/ice bath. A solution of NaOAc (5.3 g, 64 mmol, 2 equiv) in H$_2$O (20 mL) was then slowly added and the reaction was stirred for 10 min. H$_2$O$_2$ (9.7 mL, 96 mmol, 3 equiv) was then added in one portion, the cooling bath was removed, and the reaction was stirred for 3 h. The reaction was diluted with brine (50 mL) and the organic layer was separated. The aqueous layer was extracted with Et$_2$O (100 mL), and the combined organic was dried over MgSO$_4$, filtered, and concentrated. The residue was redissolved in Et$_2$O and a white precipitate was removed by filtration through celite. The filtrate was concentrated to give a yellow oil (8.8 g).

Step c:

The oil from the previous step (99 g, 359 mmol, 1 equiv) was dissolved in CH$_2$Cl$_2$ (100 mL) and Dess-Martin periodinane (82.5 g, 430 mmol, 1.5 equiv) was added in portions. After addition, the reaction was warmed to reflux and stirred for 5.5 h. Dess-Martin periodinane (15.2 g, 35.9 mmol, 0.1 equiv) was added and the mixture was stirred for 1.5 h at reflux. Reaction was allowed to cool to room temperature and stirred overnight. Saturated aqueous NaHCO$_3$ (3 L) was carefully added to the reaction, then saturated aqueous Na$_2$S$_2$O$_3$ (100 mL) was added and the mixture was stirred for 1.5 h. This was then filtered through celite, and the organic layer was separated. The aqueous layer was extracted with CH$_2$Cl$_2$ (2×300 mL) and the combined organic was dried over MgSO$_4$, filtered, and concentrated to one third of the total volume. Cyclohexane (500 mL) was added and evaporated to one third the volume. Cyclohexane (1 L) and celite (35 g) were added and the mixture was stirred at 40° C. for 5 min. This was then filtered through celite, washed with cyclohexane and evaporated to give a dark yellow oil (93.5 g). A portion of this material (31.5 g) was purified by silica gel chromatography using 8:2 hexanes:EtOAc as eluent to give the pure product (21 g, 67%).

Example 2

Synthesis of 5-[1-[(3R,6S)-6-cyclopropyl-6-[[3-fluoro-5-(trifluoromethyl)phenyl]methylcarbamoyl]tetrahydropyran-3-yl]-4-piperidyl]-2-fluorobenzoic acid

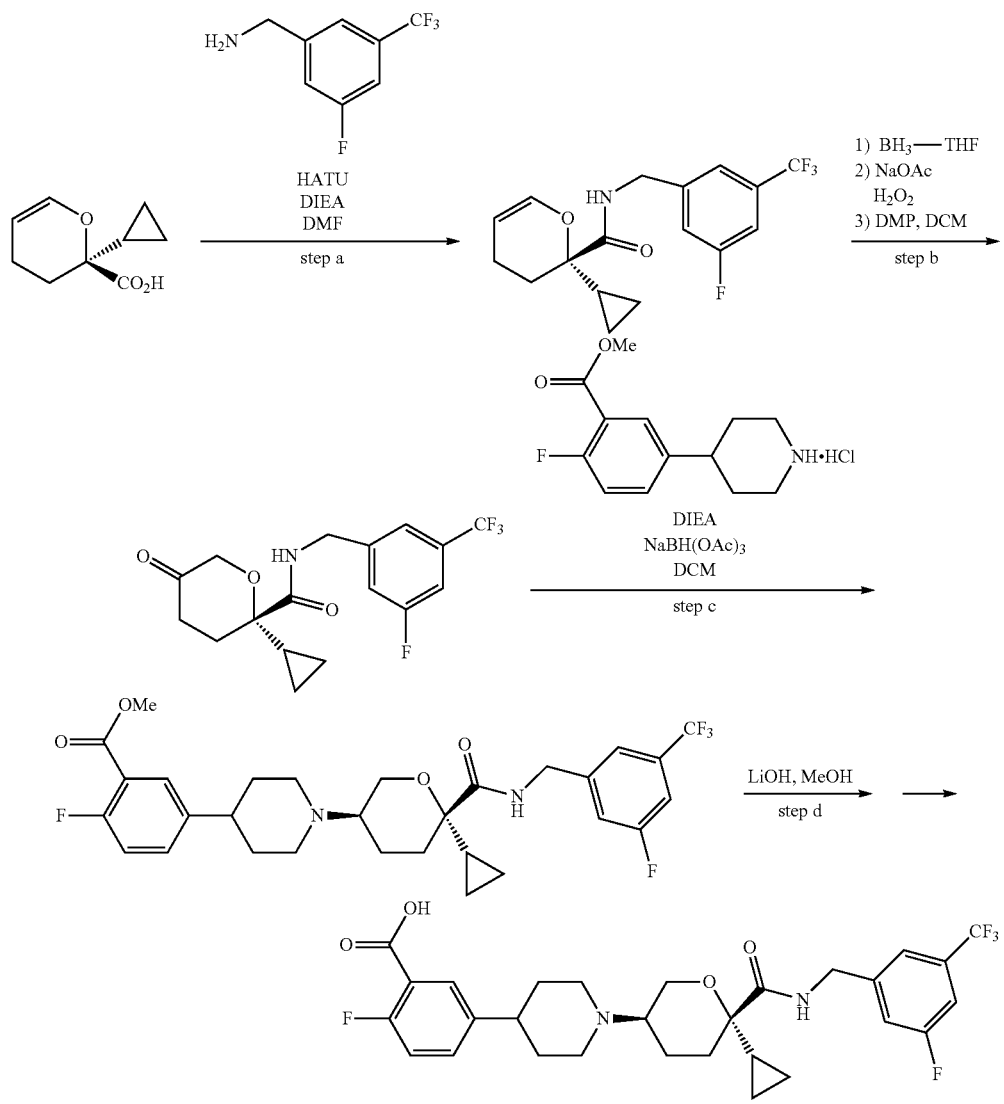

Step a:

To a mixture of the (2S)-2-cycloproyl-3,4-dihydro-2H-2-carboxylic acid (730 mg, 4.3 mol), 3-fluoro-5-trifluoromethyl-benzylamine (1.0 g, 5.2 mol), diethylisopropyl amine (650 mg, 5 mmol) in DMF (10 mL) was added HATU (2.2 g, 5.8 mmol). The resulting solution was stirred at room temperature for 3 h. The reaction mixture was quenched with water, extracted with ethyl acetate and washed with brine. The organic layer was concentrated in vacuo and the residue purified by flash chromatography (2 to 25% ethyl acetate in hexane as eluent) to give 1.2 g of (2S)-2-cyclopropyl-N-(3-fluoro-5-(trifluoromethyl)benzyl)-3,4-dihydro-2H-pyran-2-carboxamide (84% yield) as a light yellow syrup and was used directly in the next step. MS: (ES) m/z calculated for $C_{17}H_{18}F_4NO_2$ [M+H]$^+$ 344.1, found 344.1.

Step b:

The amide prepared above (1.2 g, 3.5 mmol) was dissolved in THF (10 mL), cooled in an ice-bath under $N_2$ and treated with borane in THF (1M, 10 mL, 10 mmol). The resulting mixture was stirred at 0° C. for 4 h (monitored by LC-MS) and quenched slowly with NaOAc trihydrate (2 g, 15 mmol) in water (6 mL), followed by 30% $H_2O_2$ (2.5 mL). The resulting mixture was allowed to warm up to room temperature and stirred for 1 h. The mixture was diluted with EtOAc, washed with $NaHCO_3$ and brine, and dried over $MgSO_4$, filtered and concentrated in vacuo. The residue was dissolved in $CH_2Cl_2$ (50 mL) and treated with Dess-Martin periodinane (3.2 g, 7.5 mmol). The mixture was stirred at room temperature overnight and quenched with sat $Na_2S_2O_3$ solution and concentrated under reduced pressure. The residue was diluted with EtOAc, washed with $NaHCO_3$, 1N HCl, brine, and dried over $MgSO_4$, filtered and concentrated under reduced pressure. The residue was purified by flash chromatography (20 to 45% EtOAc in hexane as eluent) to give 0.97 g of (2S)-2-cyclopropyl-N-(3-fluoro-5-(trifluoromethyl)benzyl)-5-oxotetrahydro-2H-pyran-2-carboxamide (60% yield) as a light yellow syrup and was used directly in the next step. MS: (ES) m/z calculated for $C_{17}H_{18}F_4NO_3$ [M+H]$^+$ 360.1, found 360.1.

Step c:

The ketone prepared above (140 mg, 0.39 mmol) was added to a mixture of methyl 2-fluoro-5-(piperidin-4-yl)benzoate hydrochloride (200 mg, 0.73 mmol) and N,N-diisopropylethylamine (650 mg, 5 mmol) in CH$_2$Cl$_2$ (10 mL), followed by addition of NaBH(OAc)$_3$ (160 mg, 0.76 mmol). The resulting mixture was stirred at room temperature for 1 h and then at 45° C. bath overnight. The reaction mixture was cooled to room temperature, quenched with sat NaHCO$_3$ solution, extracted with 10% MeOH in CH$_2$Cl$_2$ and dried over MgSO$_4$. After filtration and concentration in vacuo, the residue was purified by flash chromatography (2 to 5% MeOH in CH$_2$Cl$_2$ as eluent) and followed by preparative TLC (75% EtOAc in hexane as eluent) to give 30 mg of methyl 5-(1-((3R,6S)-6-cyclopropyl-6-(3-fluoro-5-(trifluoromethyl)benzylcarbamoyl)tetrahydro-2H-pyran-3-yl)piperidin-4-yl)-2-fluorobenzoate as a yellow foam and was used directly in the next step. MS: (ES) m/z calculated for $C_{30}H_{34}F_5N_2O_4$ [M+H]$^+$ 581.2, found 581.3.

Step d:

The ester prepared above (30 mg, 0.05 mmol) was dissolved in MeOH (3 mL) and water (1 mL) and treated with LiOH monohydrate (100 mg, 2.38 mmol). The resulting mixture was stirred at room temperature overnight, diluted with 2 N HCl and extracted with 10% MeOH in CH$_2$Cl$_2$ and dried over MgSO$_4$. After filtration and concentration in vacuo, the residue was purified by preparative TLC (75% EtOAc in hexane as eluent) and followed by reverse phase HPLC (C18 column, acetonitrile-H$_2$O with 0.1% TFA as eluent) to give 25 mg of title compound as a white solid. $^1$H NMR (400 MHz, CD$_3$OD) δ 8.84 (br, 1H), 7.83 (dd, J=2.5, 6.9 Hz, 1H), 7.49 (dt, J=2.1, 7.9 Hz, 2H), 7.36 (dd, J=7.9, 9.3 Hz, 2H), 7.19 (dd, J=8.5, 10.6 Hz, 1H), 4.68 (dd, J=7.1, 15.4 Hz, 1H), 4.36 (dd, J=5.4, 15.4 Hz, 1H), 4.22-4.18 (m, 1H), 3.66-3.62 (m, 3H), 3.40-3.18 (m, 4H), 2.98-2.93 (m, 1H), 2.69-2.63 (m, 1H), 2.27-2.10 (m, 3H), 1.97-1.93 (m, 2H), 1.75-1.57 (m, 2H), 1.17-1.06 (m, 1H), 0.70-0.65 (m, 1H), 0.60-0.36 (m, 3H). MS: (ES) m/z calculated for $C_{29}H_{32}F_5N_2O_4$ [M+H]$^+$ 567.2, found 567.3.

Example 3

Synthesis of 3-[(3S,4R)-1-[(3R,6S)-6-cyclopropyl-6-[[3-fluoro-5-(trifluoromethyl)phenyl]methylcarbamoyl]tetrahydropyran-3-yl]-3-methyl-4-piperidyl]benzoic acid and 3-[(3R,4S)-1-[(3R,6S)-6-cyclopropyl-6-[[3-fluoro-5-(trifluoromethyl)phenyl]methylcarbamoyl]tetrahydropyran-3-yl]-3-methyl-4-piperidyl]benzoic acid

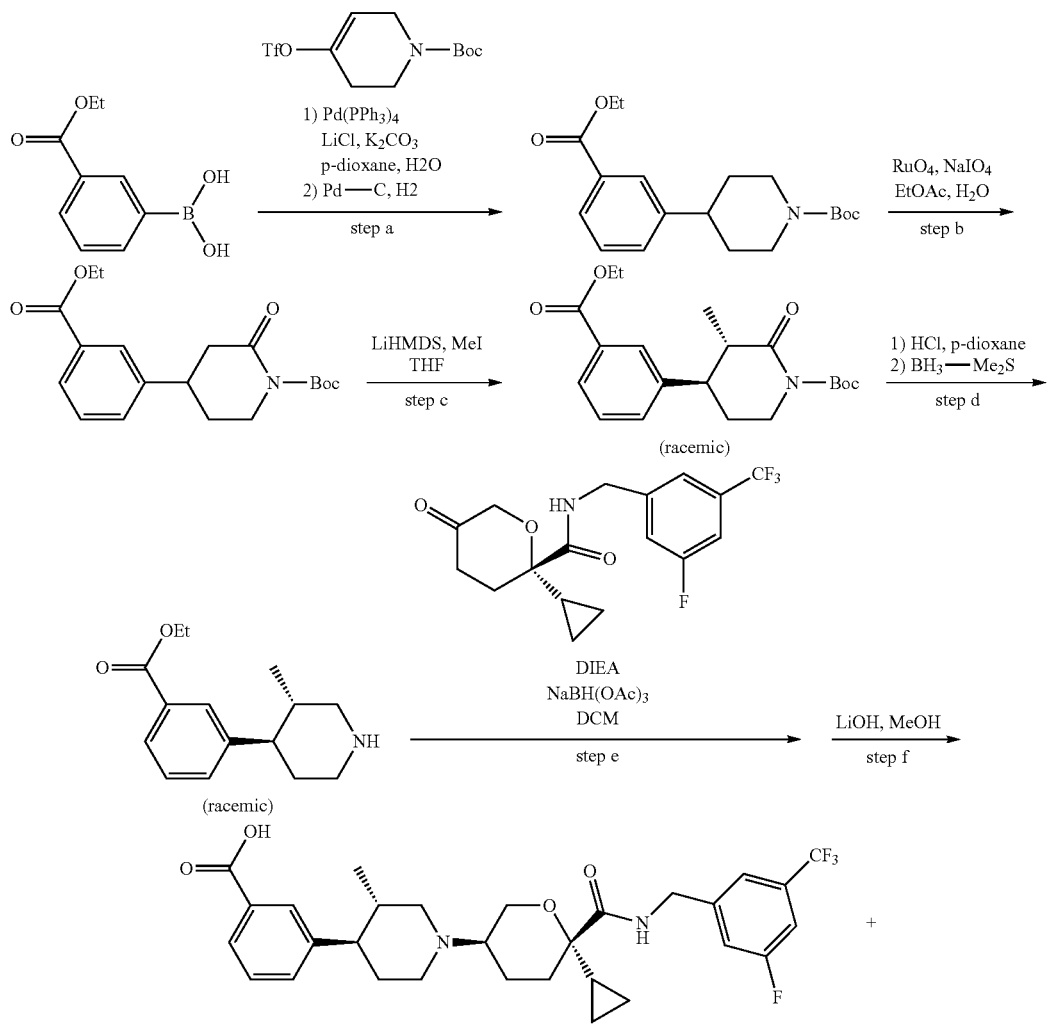

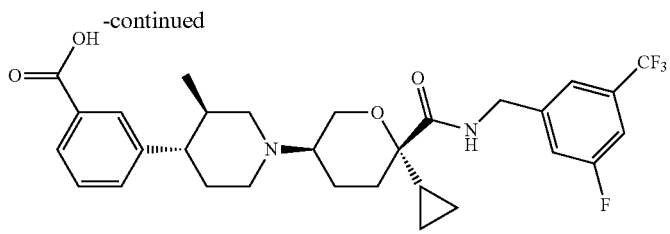

Step a:

To a mixture of 3-(ethoxycarbonyl)phenylboronic acid (4.0 g, 20.6 mmol), tert-butyl 4-(trifluoromethylsulfonyloxy)-5,6-dihydropyridine-1(2H)-carboxylate (4.0 g, 12 mmol), $K_2CO_3$ (4.2 g, 30 mmol), and LiCl (4.3 g, 100 mmol) in p-dioxane (75 mL) and water (15 mL) was added $Pd(PPh_3)_4$ (600 mg, 0.5 mmol). The resulting mixture was purged with $N_2$ and then heated to 100° C. under $N_2$ for 3 h. After cooling to room temperature, the mixture was diluted with EtOAc and washed with brine. The organic layer was concentrated in vacuo and the residue was purified by flash chromatography (2 to 25% ethyl acetate in hexane as eluent) to give 2.4 g of tert-butyl 4-(3-(ethoxycarbonyl)phenyl)-5,6-dihydropyridine-1(2H)-carboxylate (60% yield) as a light yellow syrup. This was dissolved in EtOH (40 mL), charged with 10% Pd/C (400 mg), and hydrogenated overnight under a $H_2$-balloon at room temperature. The mixture was filtered through celite and the filtrate was concentrated in vacuo to give 2.4 g of tert-butyl 4-(3-(ethoxycarbonyl)phenyl)piperidine-1-carboxylate as a light yellow syrup, which was used directly in the next step. MS: (ES) m/z calculated for $C_{19}H_{28}NO_4$ [M+H]$^+$ 334.2, found 334.2.

Step b:

The Boc-piperidine prepared above (1.4 g, 4.2 mmol) was dissolved in EtOAc (70 mL) and added slowly (over 30 min) to a solution of $RuO_4$ (200 mg, 1.21 mmol) and $NaIO_4$ (5 g, 23.4 mmol) in water (20 mL). The resulting dark mixture was stirred at room temperature for 3 h. After quenching the reaction with 10% $Na_2S_2O$ solution (100 mL), the mixture was extracted with EtOAc and washed with $NaHCO_3$, brine, and dried over $MgSO_4$. After filtration and concentration in vacuo, the residue was purified by flash chromatography (5 to 25% EtOAc in hexane as eluent) to give tert-butyl 4-(3-(ethoxycarbonyl)phenyl)-2-oxopiperidine-1-carboxylate (900 mg) as a light yellow syrup, which was used directly in the next step. MS: (ES) m/z calculated for $C_{19}H_{25}NNaO_5$ [M+Na]$^+$ 370.2, found 370.1.

Step c:

The Boc-piperidone prepared above (900 mg, 2.6 mmol) was dissolved in THF (5 mL) and added dropwise to a solution of LiHMDS (1M, 3 mL, 3 mmol) in THF under $N_2$ at −78° C. The resulting solution was stirred at −78° C. for 30 min, followed by addition of MeI (710 mg, 5 mmol) and then the temperature was allowed to slowly warm up to −20° C. over 3 h. After quenching the reaction with saturated aqueous $NH_4Cl$, the mixture was extracted with EtOAc and washed with brine. The organic layer was concentrated in vacuo and the residue was purified by flash chromatography (5 to 25% EtOAc in hexane as eluent) to give (±)-(3S,4R)-tert-butyl 4-(3-(ethoxycarbonyl)phenyl)-3-methyl-2-oxopiperidine-1-carboxylate (230 mg) as a light yellow syrup, which was used directly in the next step. MS: (ES) m/z calculated for $C_{20}H_{27}NNaO_5$ [M+Na]$^+$ 384.2, found 384.1.

Step d:

The Boc-methylpiperidone prepared above (230 mg, 0.63 mmol) was dissovled in $CH_2Cl_2$ (5 mL) and treated with 4N HCl in dioxane (5 mL, 20 mmol). After stirring at room temperature for 2 h, the solvent was concentrated in vacuo and the residue was dissolved in THF (5 mL). To this solution cooled in an ice-bath was added slowly $BH_3 \cdot Me_2S$ (2M, 1 mL). The resulting mixture was stirred at 0° C. for 6 h, followed by standing at 4° C. for 72 h. The solvent was concentrated in vacuo and the residue dissolved in EtOH (5 mL) with conc. HCl (0.1 mL, 12 mmol). The mixture was stirred at 50° C. for 30 min. The organic layer was concentrated in vacuo and the residue was purified by flash chromatography (2 to 20% MeOH in $CH_2Cl_2$ with 2% $NH_4OH$ as eluent) to give 110 mg of (±)-ethyl 3-((3S,4R)-3-methylpiperidin-4-yl)benzoate as a light yellow foam, which was used directly in the next step. MS: (ES) m/z calculated for $C_{15}H_{22}NO_2$ [M+H]$^+$ 248.2, found 248.2.

Step e:

The amine prepared above (110 mg, 0.44 mmol) was dissolved in $CH_2Cl_2$ (10 mL) and charged with N,N-diisopropylethylamine (390 mg, 3 mmol), (2S)-2-cyclopropyl-N-(3-fluoro-5-(trifluoromethyl)benzyl)-5-oxotetrahydro-2H-pyran-2-carboxamide (120 mg, 0.33 mmol) and followed by addition of $NaBH(OAc)_3$ (110 mg, 0.52 mmol). The resulting mixture was stirred at room temperature for 1 h and then at 45° C. overnight. The reaction mixture was cooled to room temperature, quenched with saturated aqueous $NaHCO_3$, extracted with 10% MeOH in $CH_2Cl_2$ and dried over $MgSO_4$. After filtration and concentration in vacuo, the residue was purified by flash chromatography (2 to 5% MeOH in $CH_2Cl_2$ as eluent) and by preparative TLC (60% EtOAc in hexane as eluent) to give a mixture (75 mg) of ethyl 3-[(3S,4R)-1-[(3R,6S)-6-cyclopropyl-6-[[3-fluoro-5-(trifluoromethyl)phenyl]methylcarbamoyl]tetrahydropyran-3-yl]-3-methyl-4-piperidyl]benzoate and ethyl 3-[(3R,4S)-1-[(3R,6S)-6-cyclopropyl-6-[[3-fluoro-5-(trifluoromethyl)phenyl]methylcarbamoyl]tetrahydropyran-3-yl]-3-methyl-4-piperidyl]benzoate as a yellow foam and was used directly in the next step. MS: (ES) m/z calculated for $C_{32}H_{39}F_4N_2O_4$ [M+H]$^+$ 591.3, found 591.2.

Step f:

To a solution of the ester prepared above (75 mg, 0.13 mmol) in MeOH (5 mL) and water (2 mL) was added LiOH monohydrate (210 mg, 5 mmol). The resulting mixture was stirred at 80° C. for 2 h, diluted with 2 N HCl and extracted with 10% MeOH in $CH_2Cl_2$ and dried over $MgSO_4$. After filtration and concentration in vacuo, the residue was purified by preparative TLC (20% MeOH in EtOAc as eluent) and then by reverse phase HPLC (C18 column, acetonitrile-$H_2O$ with 0.1% TFA as eluent) to give 30 mg of title compound (mixture of diastereomers) as an off-white solid. $^1$H NMR (400 MHz, $CD_3OD$) δ 8.87 (br, 1H), 7.85-7.91 (m, 2H), 7.27-7.51 (m, 5H), 4.68 (ddd, J=4.0, 7.0, 15.6 Hz, 1H), 4.37 (dt, J=4.6, 15.4 Hz, 1H), 4.26-4.20 (m, 1H), 3.75-3.55 (m, 3H), 3.34-3.15 (m, 3H), 2.90 (q, J=11.9 Hz, 1H), 2.70-2.63 (m, 1H), 2.57-2.52 (m, 1H), 2.33-2.20 (m, 1H), 2.10-1.96 (m, 2H), 1.72-1.55 (m, 3H), 1.15-1.06 (m, 1H), 0.77 (d, J=8.0 Hz, 3H), 0.76-0.67 (m, 1H), 0.61-0.38 (m, 3H). MS: (ES) m/z calculated for $C_{30}H_{35}F_4N_2O_4$ $[M+H]^+$ 563.3, found 563.3.

Example 4

Synthesis of 5-[(2S)-4-[(3R,6S)-6-cyclopropyl-6-[[3-fluoro-5-(trifluoromethyl)phenyl]methylcarbamoyl]tetrahydropyran-3-yl]-2-methyl-piperazin-1-yl]-2-fluoro-benzoic acid (50% EtOAc in hexane as eluent) to give methyl 5-[(2S)-4-[(3R,6S)-6-cyclopropyl-6-[[3-fluoro-5-(trifluoromethyl)phenyl]methylcarbamoyl]tetrahydropyran-3-yl]-2-methyl-piperazin-1-yl]-2-fluoro-benzoate (60 mg) as a yellow foam that was used directly in the next step. MS: (ES) m/z calculated for $C_{30}H_{35}F_5N_3O_4$ $[M+H]^+$ 596.3, found 596.4.

Step b:

To a solution of the ester prepared above (60 mg, 0.10 mmol) in MeOH (5 mL) and water (2 mL) was added LiOH monohydrate (210 mg, 5 mmol). The resulting mixture was stirred at 80° C. for 2 h, diluted with 2 N HCl and extracted with 10% MeOH in $CH_2Cl_2$ and dried over $MgSO_4$. After

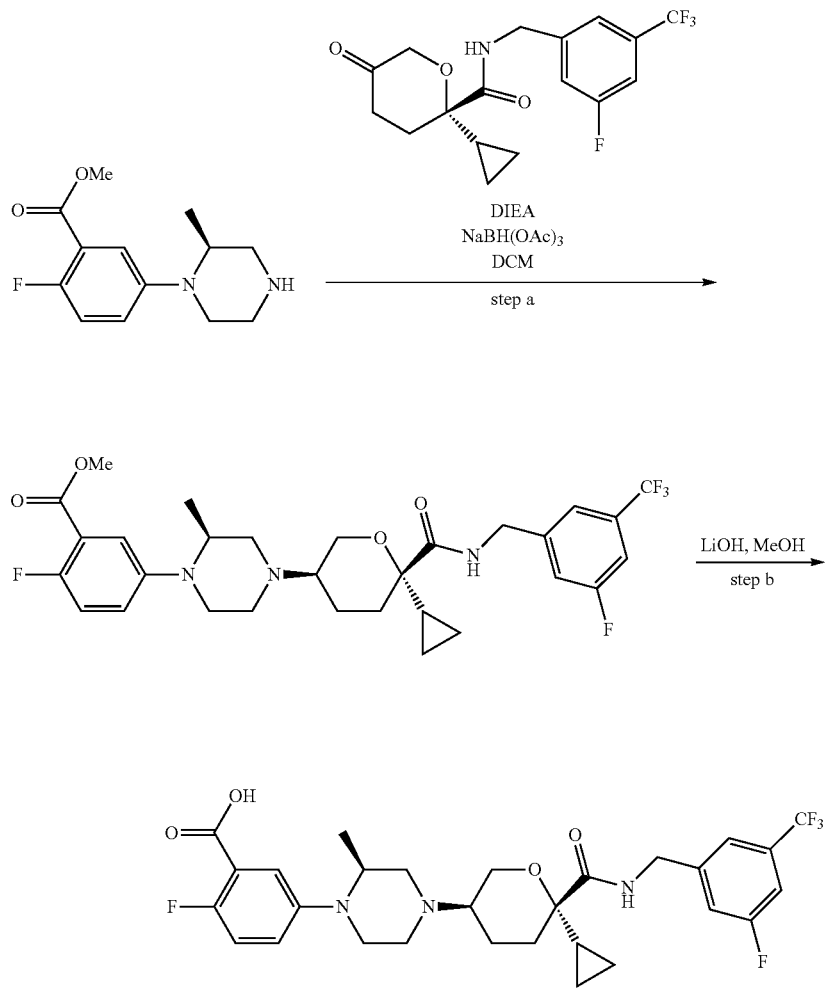

Step a:

To a mixture of (S)-methyl 2-fluoro-5-(2-methylpiperazin-1-yl)benzoate di-HCl salt (150 mg, 0.46) and N,N-diisopropylethylamine (390 mg, 3 mmol) in $CH_2Cl_2$ (10 mL) were added (2S)-2-cyclopropyl-N-(3-fluoro-5-(trifluoromethyl)benzyl)-5-oxotetrahydro-2H-pyran-2-carboxamide (150 mg, 0.42 mmol) and NaBH(OAc)$_3$ (211 mg, 1 mmol). The resulting mixture was stirred at room temperature for 1 h and then at 45° C. overnight. The reaction mixture was cooled to room temperature, quenched with saturated aqueous NaHCO$_3$, extracted with 10% MeOH in $CH_2Cl_2$ and dried over MgSO$_4$. After filtration and concentration in vacuo, the residue was purified by flash chromatography (2 to 5% MeOH in $CH_2Cl_2$ as eluent) and then by preparative TLC filtration and concentration in vacuo, the residue was purified by preparative TLC (EtOAc as eluent) and then by reverse phase HPLC (C18 column, acetonitrile-H$_2$O with 0.1% TFA as eluent) to give 30 mg of the title compound as an off-white solid. $^1$H NMR (400 MHz, CD$_3$OD) δ 8.67 (br, 1H), 7.51-7.29 (m, 4H), 7.16-6.99 (m, 2H), 4.59 (dd, J=6.8, 15.4 Hz, 1H), 4.43 (dd, J=5.6, 15.4 Hz, 1H), 3.99 (ddd, J=2.2, 4.3, 11.4 Hz, 1H), 3.54 (dt, J=3.3, 6.3 Hz, 1H), 3.44-3.32 (m, 1H), 3.10-3.02 (m, 2H), 2.86-2.82 (m, 2H), 2.75-2.67 (m, 1H), 2.67-2.47 (m, 3H), 2.05-1.97 (m, 1H), 1.55 (dt, J=3.6, 13.4 Hz, 1H), 1.44-1.26 (m, 1H), 1.15-1.02 (m, 1H), 0.94 (d, J=6 Hz, 3H), 0.94-0.83 (m, 1H), 0.77-0.66 (m, 1H), 0.61-0.36 (m, 3H). MS: (ES) m/z calculated for $C_{29}H_{33}F_5N_3O_4$ $[M+H]^+$ 582.2, found 582.2.

Example 5

Synthesis of 5-[(2S)-4-[(3R,6S)-6-cyclopropyl-6-[4-[3-(trifluoromethyl)phenyl]piperazine-1-carbonyl]tetrahydropyran-3-yl]-2-methyl-piperazin-1-yl]-2-fluoro-benzoic acid

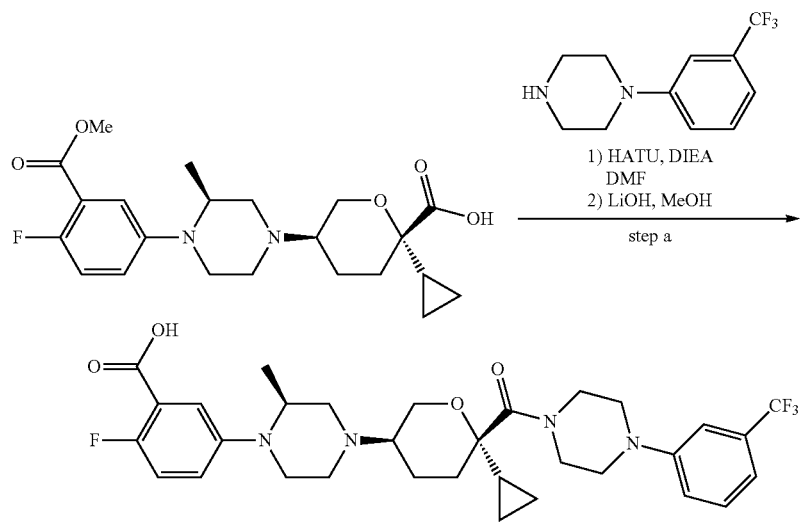

Step a:

To a mixture of (2S,5R)-2-cyclopropyl-5-[(3S)-4-(4-fluoro-3-methoxycarbonyl-phenyl)-3-methyl-piperazin-1-yl]tetrahydropyran-2-carboxylic acid (70 mg, 0.17 mmol), 1-(3-(trifluoromethyl)phenyl)piperazine (70 mg, 0.3 mmol), N,N-diisopropylethylamine (130 mg, 1 mmol) in DMF (5 mL) was added HATU (110 mg, 0.29 mmol). The resulting solution was stirred at room temperature for 1 h. The reaction mixture was quenched with water, extracted with ethyl acetate and washed with brine. The organic layer was concentrated in vacuo and the residue was purified by flash chromatography (10 to 35% ethyl acetate in hexane as eluent) to give 85 mg of the intermediate ester. This was dissolved in MeOH (5 mL) and water (2 mL) and treated with LiOH monohydrate (210 mg, 5 mmol). The resulting mixture was stirred at room temperature for 2 h, diluted with 2 N HCl and extracted with 10% MeOH in $CH_2Cl_2$ and dried over $MgSO_4$. After filtration and concentration in vacuo, the residue was purified by preparative TLC (EtOAc as eluent) and then by reverse phase HPLC (C18 column, acetonitrile-$H_2O$ with 0.1% TFA as eluent) to give 50 mg of the title compound as an off-white solid. $^1$H NMR (400 MHz, $CD_3OD$) δ 7.18-7.80 (m, 7H), 4.20-4.40 (m, 4H), 3.20-3.98 (m, 14H), 3.01-2.88 (m, 1H), 2.63 (d, J=13.7 Hz, 1H), 2.35-2.25 (m, 1H), 1.85-1.78 (m, 1H), 1.56-1.48 (m, 1H), 1.30-1.20 (m, 1H), 1.04-0.94 (m, 3H), 0.92-0.83 (m, 1H), 0.74-0.60 (m, 2H), 0.49-0.40 (m, 1H). MS: (ES) m/z calculated for $C_{32}H_{39}F_4N_4O_4$ [M+H]$^+$ 619.3, found 619.2.

Synthesis of (2S,5R)-2-cyclopropyl-5-[(3S,4R)-4-(4-fluorophenyl)-3-methoxycarbonyl-1-piperidyl]tetrahydropyran-2-carboxylic acid

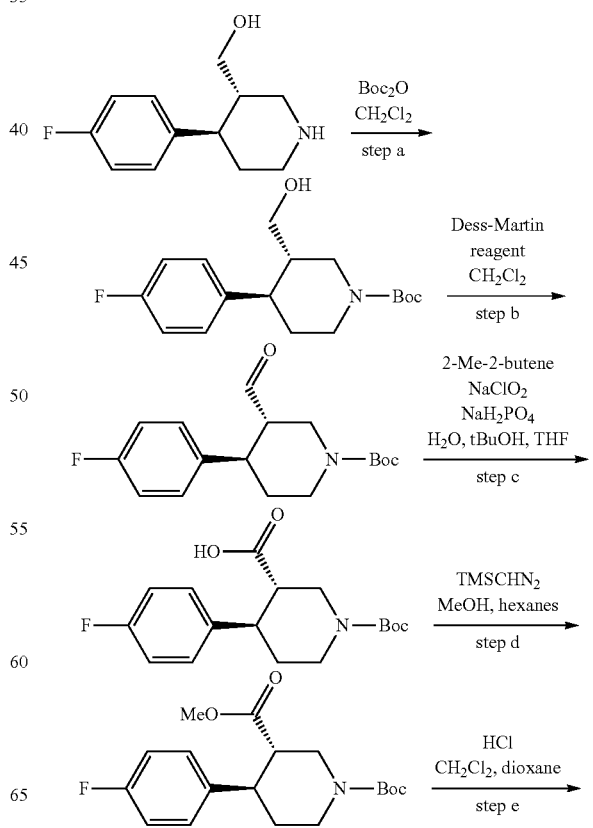

-continued

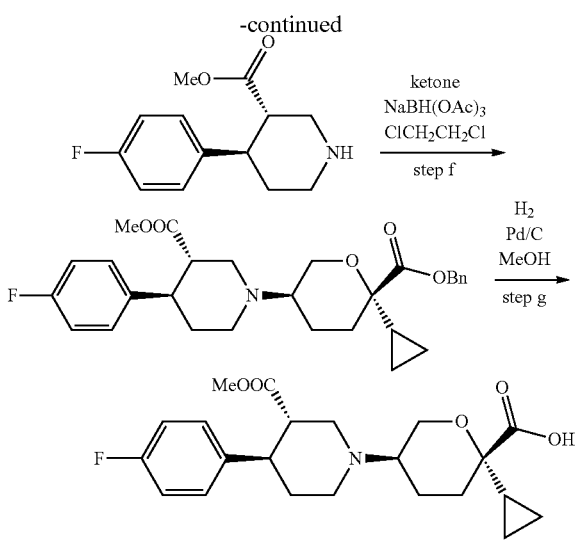

Step a:

[(3S,4R)-4-(4-Fluoro-phenyl)-piperidin-3-yl]-methanol (300 g, 143 mm, 1 equiv) was suspended in CH$_2$Cl$_2$ (10 m) and Boc anhydride (3.23 g, 14.8 mmol, 1.03 equiv) was added. This was stirred for 2 h then concentrated to give the crude, which was used in the next reaction without further purification.

Step b:

To the crude from step a (298 mg, 0.965 mmol, 1 equiv) was added CH$_2$Cl$_2$ (2 mL) and Dess-Martin periodinane (449 mg, 1.06 mmol, 1.1 equiv). The reaction was stirred for 1.5 h at room temperature. This mixture was then purified by silica gel chromatography (hexanes:EtOAc as eluent) to give (3S,4R)-4-(4-fluoro-phenyl)-3-hydroxymethyl-piperidine-1-carboxylic acid tert-butyl ester (167 mg, 56%).

Step c:

To (3S,4R)-4-(4-Fluoro-phenyl)-3-hydroxymethyl-piperidine-1-carboxylic acid tert-butyl ester (167 mg, 0.543 mmol, 1 equiv) was added t-BuOH (3.5 mL) and 2-methyl-2-butene in THF (2M, 2 mL, 4 mmol, 7 equiv). This was cooled in an ice bath and a mixture of NaClO$_2$ (80%, 329 mg, 2.9 mmol, 5 equiv) and NaH$_2$PO$_4$ (535 mg, 3.88 mmol, 7 equiv) in H$_2$O (1.8 mL) was added. The mixture was stirred for 30 min then concentrated. The residue was partitioned between EtOAc and H$_2$O, separated and extracted with EtOAc (3×). The organic was dried over Na$_2$SO$_4$, filtered, and concentrated to give the crude (176 mg).

Step d:

To the crude from the previous step (4.17 g, 11 mmol, 1 equiv) was added MeOH (15 mL) and the solution was cooled in an ice bath. Trimethylsilyldiazomethane in hexanes (2M, 10 mL, 20 mmol, 1.8 equiv) was added until the solution remains yellow. This was then concentrated and purified by silica gel chromatography (hexanes:EtOAc as eluent) to give (3S,4R)-4-(4-Fluoro-phenyl)-piperidine-1,3-dicarboxylic acid 1-tert-butyl ester 3-methyl ester (3.69 g).

Step e:

To (3S,4R)-4-(4-Fluoro-phenyl)-piperidine-1,3-dicarboxylic acid 1-tert-butyl ester 3-methyl ester (3.67 g, 10.9 mmol, 1 equiv) was added CH$_2$Cl$_2$ (10 mL) and HCl in dioxane (4M, 10 mL, 40 mmol, 3.7 equiv). This was stirred for 1.5 h, then concentrated. The residue was diluted with CH$_2$Cl$_2$ and washed with saturated aqueous NaHCO$_3$. The aqueous was extracted with CH$_2$Cl$_2$ (2×), then the organic was dried over Na$_2$SO$_4$, filtered and concentrated to give (3S,4R)-4-(4-Fluoro-phenyl)-piperidine-3-carboxylic acid methyl ester (2.55 g).

Step f:

To (3S,4R)-4-(4-fluoro-phenyl)-piperidine-3-carboxylic acid methyl ester (2.55 g, 10.8 mmol, 1.1 equiv) was added (2S)-2-Cyclopropyl-5-oxo-tetrahydro-pyran-2-carboxylic acid benzyl ester (2.73 g, 9.95 mmol, 1 equiv) in dichloroethane (30 mL) and the mixture was cooled in an ice bath. NaBH(OAc)$_3$ (3.28 g, 15.5 mmol, 1.5 equiv) was added and the reaction was then stirred overnight at room temperature. The reaction was diluted with CH$_2$Cl$_2$ and washed with saturated aqueous NaHCO$_3$. The aqueous was extracted with CH$_2$Cl$_2$ (2×) and the organic was then dried over Na$_2$SO$_4$, filtered and concentrated. The crude was purified by silica gel chromatography (hexanes:EtOAc as eluent) to give the product (3.74 g) as a cis/trans mixture.

Step g:

To the mixture from step f (3.74 g, 7.54 mmol) was added MeOH (25 mL) followed by 10% wet Degussa type Pd/C (304 mg). The reaction was stirred under H$_2$ for 3 h. The reaction was then filtered through celite, rinsing with MeOH and CH$_2$Cl$_2$. The solution was then concentrated and purified by silica gel chromatography (CH$_2$Cl$_2$:MeOH as eluent) to give (2S,5R)-2-cyclopropyl-5-[(3S,4R)-4-(4-fluorophenyl)-3-methoxycarbonyl-1-piperidyl]tetrahydropyran-2-carboxylic acid (1.318 g, 43%) as the pure isomer.

Example 6

Synthesis of (3S,4R)-1-[(3R,6S)-6-cyclopropyl-6-[8-fluoro-6-(trifluoromethyl)-2,4-dihydro-1,3-benzoxazine-3-carbonyl]tetrahydropyran-3-yl]-4-(4-fluorophenyl)piperidine-3-carboxylic acid

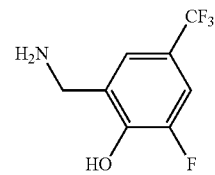

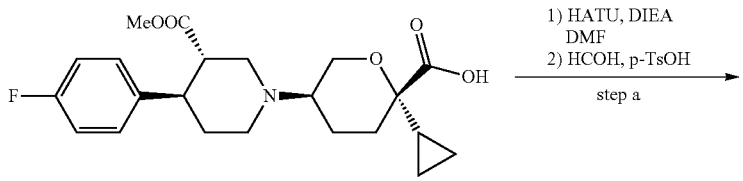

1) HATU, DIEA DMF
2) HCOH, p-TsOH
step a

-continued

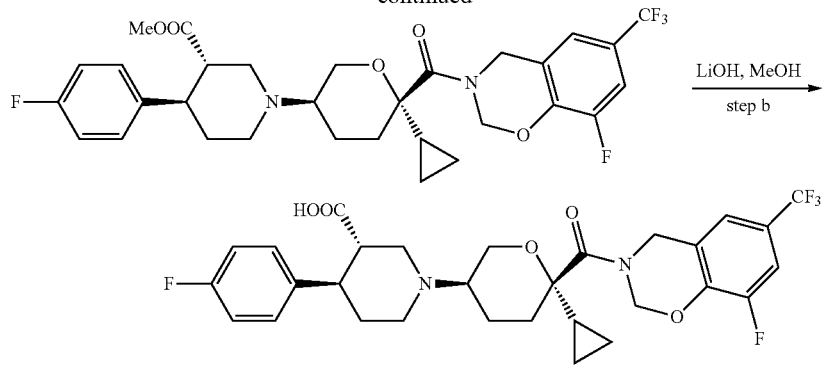

Step a:

To a mixture of (2S,5R)-2-cyclopropyl-5-[(3S,4R)-4-(4-fluorophenyl)-3-methoxycarbonyl-1-piperidyl]tetrahydropyran-2-carboxylic acid (100 mg, 0.25 mmol), 2-(aminomethyl)-6-fluoro-4-(trifluoromethyl)phenol (80 mg, 0.38 mmol), and N,N-diisopropylethylamine (390 mg, 3 mmol) in DMF (6 mL) was added HATU (150 mg, 0.39 mmol). The resulting solution was stirred at room temperature for 1 h. The reaction mixture was quenched with water, extracted with ethyl acetate and washed with brine. The organic layer was concentrated in vacuo and the residue was dissolved in toluene (10 mL) and treated with paraformaldehyde (600 mg, 20 mmol) and p-TsOH (150 mg, 0.87 mmol). The resulting mixture was stirred at 100° C. for 6 h. After cooling to room temperature, the mixture was diluted with EtOAc and washed with sat NaHCO$_3$ solution, brine and dried over MgSO$_4$. After filtration and concentration in vacuo, the residue was purified by flash chromatography (10% to 30% EtOAc in hexane as eluent) to give methyl (3S,4R)-1-[(3R,6S)-6-cyclopropyl-6-[8-fluoro-6-(trifluoromethyl)-2,4-dihydro-1,3-benzoxazine-3-carbonyl]tetrahydropyran-3-yl]-4-(4-fluorophenyl)piperidine-3-carboxylate (80 mg) as a yellow foam, which was used directly in the next step. MS: (ES) m/z calculated for $C_{31}H_{34}F_5N_2O_5$ [M+H]$^+$ 609.2, found 609.3.

Step b:

The ester prepared above (80 mg, 0.13 mmol) was dissolved in MeOH (5 mL) and water (2 mL) and then treated with LiOH monohydrate (210 mg, 5 mmol). The resulting mixture was stirred at 60° C. for 1 h, diluted with 2 N HCl and extracted with 10% MeOH in CH$_2$Cl$_2$ and dried over MgSO$_4$. After filtration and concentration in vacuo, the residue was purified by preparative TLC (EtOAc as eluent) and then by reverse phase HPLC (C18 column, acetonitrile-H$_2$O with 0.1% TFA as eluent) to give 50 mg of the title compound as an off-white solid. $^1$H NMR (400 MHz, CD$_3$OD) δ 7.40-7.36 (m, 2H), 7.32-7.20 (m, 2H), 7.04 (td, J=2.4, 9.1 Hz, 1H), 6.20 (br, 1H), 5.75 (br, 1H), 4.98-4.88 (m, 1H), 4.45-4.36 (m, 1H), 3.77-3.40 (m, 4H), 3.35-2.98 (m, 8H), 2.65 (dt, J=3.6, 13.7 Hz, 1H), 2.33-2.23 (m, 1H), 2.09-1.95 (m, 2H), 1.84-1.72 (m, 1H), 1.65-1.58 (m, 1H), 1.25-1.15 (m, 1H), 0.65-0.46 (m, 3H). MS: (ES) m/z calculated for $C_{30}H_{32}F_5N_2O_5$ [M+H]$^+$ 595.2, found 595.3.

Synthesis of ethyl 3-[(3R,4S)-3-methyl-4-piperidyl]benzoate

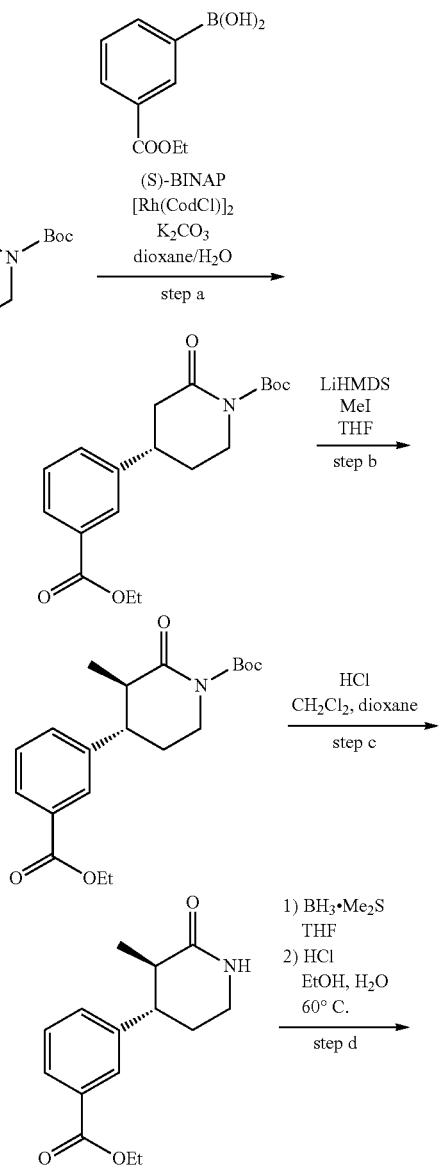

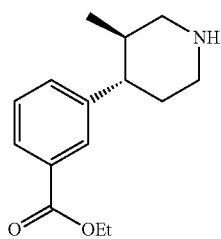

Step a:

3-Carbethoxyphenylboronic acid (6.0 g, 31 mmol, 2.2 equiv) was dissolved in dioxane (50 mL) and cooled in an ice bath. $K_2CO_3$ (4.6 g, 33 mmol, 2.4 equiv) was added followed by $H_2O$ (5 mL). $N_2$ was bubbled through the solution for 2 min, then $(Rh(cod)Cl)_2$ (600 mg, 1.2 mmol, 0.08 equiv) and (S)-BINAP (1.68 g, 2.56 mmol, 0.18 equiv) was added. $N_2$ was bubbled through the solution for 5 more min, then 6-oxo-3,6-dihydro-2H-pyridine-1-carboxylic acid tert-butyl ester (2.70 g, 14 mmol, 1 equiv) was added slowly. $N_2$ was bubbled through the solution for 5 more min, then the reaction was allowed to warm to room temperature over 1 h. The reaction was heated to 45° C. for 1 h, then was allowed to cool to room temperature and stirred overnight. The reaction was diluted with EtOAc, washed with $H_2O$, then brine and then concentrated. The residue was purified by silica gel chromatography (5% to 20% EtOAc in hexanes) to give (S)-4-(3-ethoxycarbonyl-phenyl)-2-oxo-piperidine-1-carboxylic acid tert-butyl ester (3.5 g, 74%).

Step b:

LiHMDS (1M, 13.4 mL, 13.4 mmol, 1.3 equiv) was added to THF (20 mL) and this solution was cooled to −60° C. (S)-4-(3-Ethoxycarbonyl-phenyl)-2-oxo-piperidine-1-carboxylic acid tert-butyl ester (3.5 g, 10 mmol, 1 equiv) in THF was then added over 10 min while keeping the internal temperature below −45° C. The reaction was stirred for 45 min in the −78° C. bath, then MeI (2 mL) was added. The reaction was stirred in the bath for 3 h. then quenched by adding $NH_4OH$ and warmed to room temperature. The mixture was extracted with EtOAc (150 mL) and concentrated. The resulting residue was purified by silica gel chromatography (5% to 15% EtOAc in hexanes) to give (3R,4S)-4-(3-Ethoxycarbonyl-phenyl)-3-methyl-2-oxo-piperidine-1-carboxylic acid tert-butyl ester (3.0 g, 83%).

Step c:

(3R,4S)-4-(3-Ethoxycarbonyl-phenyl)-3-methyl-2-oxo-piperidine-1-carboxylic acid tert-butyl ester (3.0 g, 8.3 mmol) was dissolved in $CH_2Cl_2$ (20 mL) and HCl in dioxane (4N, 20 mL, 80 mmol) was added. This mixture was allowed to stir at room temperature for 4 h then concentrated to give the product, which was used directly in the next step.

Step d:

3-((3R,4S)-3-Methyl-2-oxo-piperidin-4-yl)-benzoic acid ethyl ester (8.3 mmol, 1 equiv) was dissolved in THF (35 mL) and $BH_3 \cdot SMe_2$ in THF (2M, 12 mL, 24 mmol, 3 equiv) was slowly added. The reaction was allowed to sit in a 4° C. refrigerator for 3 days, then the solution was concentrated. The residue was dissolved in EtOH (35 mL) and concentrated HCl (1.8 mL, 22 mmol) was added. This solution was stirred at 60° C. for 2 h then concentrated. The residue was purified by silica gel chromatography (5% to 15% MeOH in $CH_2Cl_2$) to give ethyl 3-[(3R,4S)-3-methyl-4-piperidyl]benzoate (1.2 g, 59%).

Example 7

Synthesis of 3-[(3R,4S)-1-[(3R,6S)-6-cyclopropyl-6-[8-fluoro-6-(trifluoromethyl)-2,4-dihydro-1,3-benzoxazine-3-carbonyl]tetrahydropyran-3-yl]-3-methyl-4-piperidyl]benzoic acid

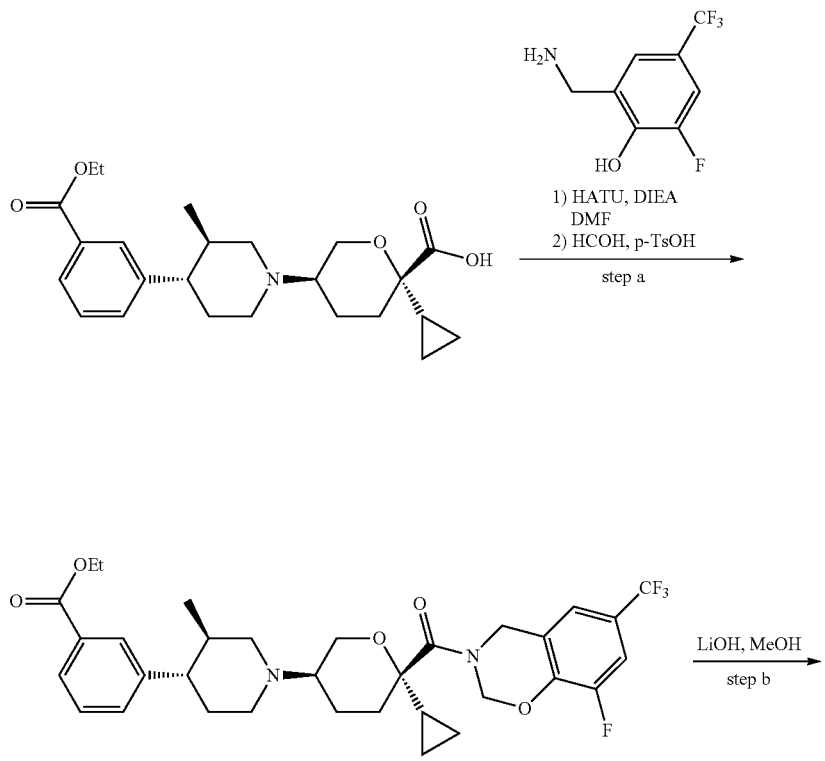

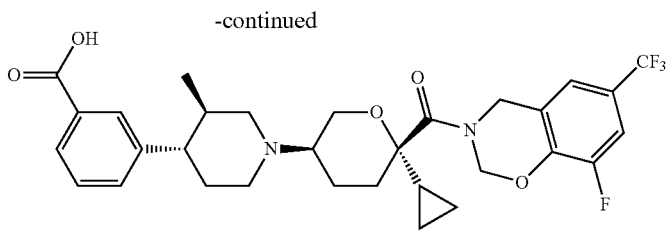

Step a:

To a mixture of (2S,5R)-2-cyclopropyl-5-[(3R,4S)-4-(3-ethoxycarbonylphenyl)-3-methyl-1-piperidyl]tetrahydropyran-2-carboxylic acid (85 mg, 0.21 mmol), 2-(aminomethyl)-6-fluoro-4-(trifluoromethyl)phenol (60 mg, 0.29 mmol), N,N-diisopropylethylamine amine (390 mg, 3 mmol) in DMF (6 mL) was added HATU (120 mg, 0.32 mmol). The resulting solution was stirred at room temperature for 1 h. The reaction mixture was quenched with water (25 mL), extracted with ethyl acetate (50 mL) and washed with brine (25 mL). The organic layer was concentrated in vacuo and the residue was dissolved in toluene (10 mL) and treated with paraformaldehyde (600 mg, 20 mmol) and p-TsOH (150 mg, 0.87 mmol) at 100° C. for 6 h. After cooling to room temperature, the mixture was diluted with EtOAc and washed with saturated aqueous NaHCO$_3$ (20 mL), brine (20 mL) and dried over MgSO$_4$. After filtration and concentration in vacuo, the residue was purified by preparative TLC (35% EtOAc in hexane as eluent) to give ethyl 3-[(3R,4S)-1-[(3R,6S)-6-cyclopropyl-6-[8-fluoro-6-(trifluoromethyl)-2,4-dihydro-1,3-benzoxazine-3-carbonyl]tetrahydropyran-3-yl]-3-methyl-4-piperidyl]benzoate (15 mg) as a yellow foam and this was used directly in the next step. MS: (ES) m/z calculated for C$_{33}$H$_{39}$F$_4$N$_2$O$_5$ [M+H]$^+$ 619.3, found 619.3.

Step b:

The ester prepared above (15 mg, 0.024 mmol) was dissolved in MeOH (5 mL) and water (2 mL) and then treated with LiOH monohydrate (100 mg, 2.5 mmol) at 60° C. for 3 h. The reaction was diluted with 2 N HCl, extracted with 10% MeOH in CH$_2$Cl$_2$ and dried over MgSO$_4$. After filtration and concentration in vacuo, the residue was purified by preparative TLC (EtOAc as eluent) and followed by reverse phase HPLC (C18 column, acetonitrile-H$_2$O with 0.1% TFA as eluent) to give 7 mg of the title compound as an off-white solid. $^1$H NMR (400 MHz, CD$_3$OD) δ 7.94-7.82 (m, 2H), 7.48-7.37 (m, 4H), 6.20 (br, 1H), 5.75 (br, 1H), 4.98-4.90 (m, 1H), 4.45-4.35 (m, 1H), 3.70-3.38 (m, 4H), 3.35-3.02 (m, 4H), 2.90-2.80 (m, 1H), 2.68-2.62 (m, 1H), 2.60-2.53 (m, 1H), 2.32-1.92 (m, 3H), 1.85-1.70 (m, 1H), 1.65-1.55 (m, 1H), 1.32-1.20 (m, 2H), 0.75 (d, J=6.7 Hz, 3H), 0.65-0.46 (m, 3H). MS: (ES) m/z calculated for C$_{31}$H$_{35}$F$_4$N$_2$O [M+H]$^+$ 591.2, found 591.3.

Synthesis of 2-(aminomethyl)-6-chloro-4-(trifluoromethyl)phenol

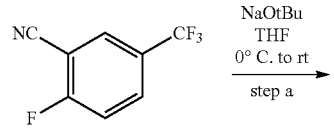

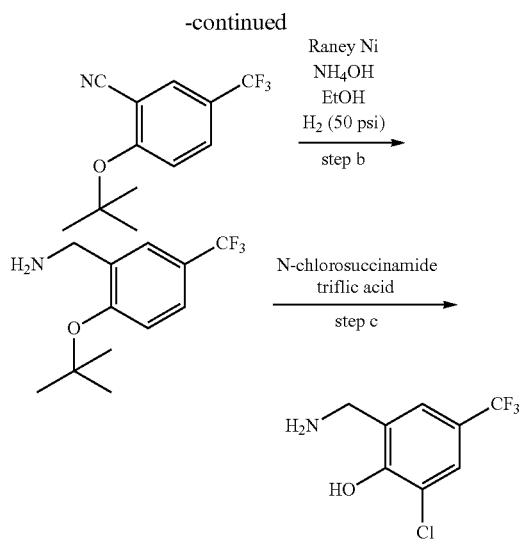

Step a:

A solution of 2-fluoro-5-(trifluoromethyl)benzonitrile (50.0 g, 265 mmol, 1 equiv) in THF (1.0 L) was treated with NaOtBu (30.5 g, 317 mmol, 1.2 equiv) for 10 min on ice and then at room temperature overnight. The mixture was then concentrated and the residue was diluted with H$_2$O (400 mL) and extracted with hexanes (2×300 mL). The combined organic was dried over MgSO$_4$, filtered and concentrated to give a yellow oil (61.7 g, 96%) that solidified upon standing. This was used in step b.

Step b:

2-tert-Butoxy-5-trifluoromethyl-benzonitrile (20.0 g, 82.3 mmol) was dissolved in EtOH (100 mL). NH$_4$OH (10 mL) was added, followed by Raney Nickel slurry in water (5 mL). The reaction was shaken under H$_2$ (50 psi) overnight. The mixture was filtered through celite and concentrated. The residue was dissolved in hexanes and dried over MgSO$_4$, filtered and concentrated to give a yellow oil (19.8 g, 97%).

Step c:

Trifluoroacetic acid (2 mL) was added to 2-tert-butoxy-5-trifluoromethyl-benzylamine (2.5 g, 10 mmol, 1 equiv) with stirring. Triflic acid (10 mL) was carefully added to the solution, followed by portionwise addition of N-chlorosuccinimide (2.7 g, 20 mmol, 2 equiv). The reaction was stirred at room temperature for 2 h, then poured into H$_2$O and neutralized with saturated aqueous NaHCO$_3$. The mixture was extracted with EtOAc (2×25 mL), then the combined organic was dried over MgSO$_4$, filtered and concentrated. The resulting brown residual was dissolved in minimal MeOH and a gray precipitate formed. The solid was filtered and washed with minimal MeOH to give the product as a gray solid (850 mg, 37%).

Example 8

Synthesis of 3-[(3R,4S)-1-[(3R,6S)-6-[8-chloro-6-(trifluoromethyl)-2,4-dihydro-1,3-benzoxazine-3-carbonyl]-6-cyclopropyl-tetrahydropyran-3-yl]-3-methyl-4-piperidyl]benzoic acid

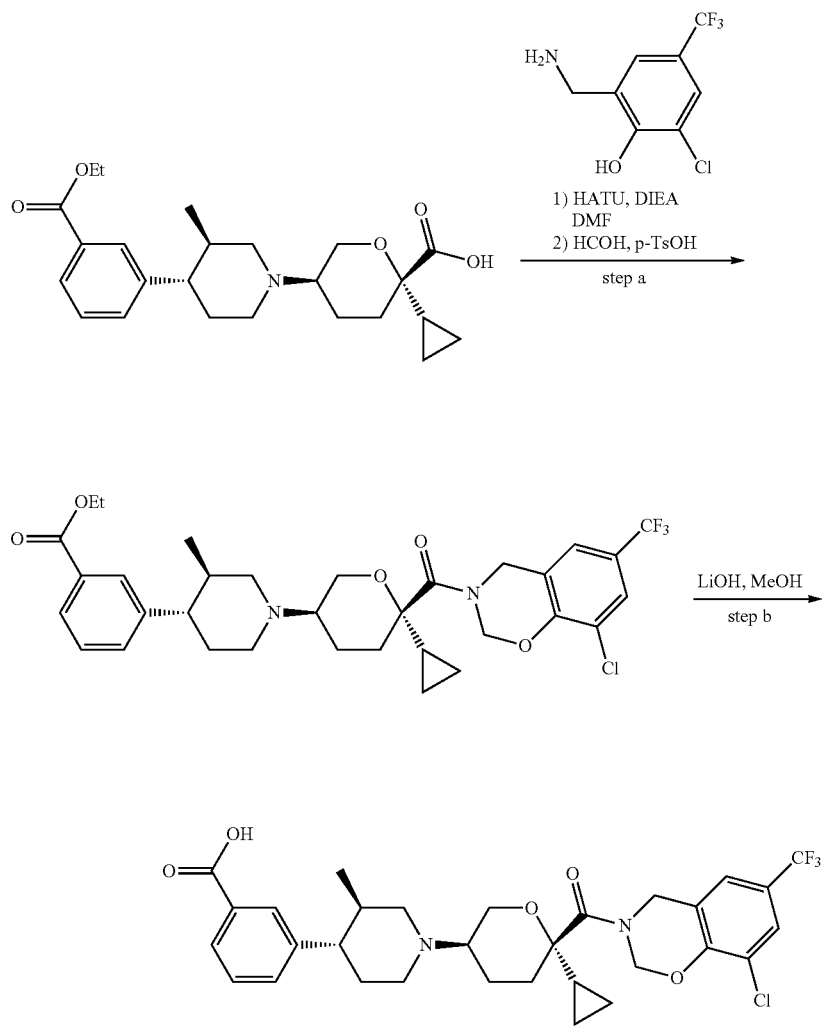

Step a:

To a mixture of the (2S,5R)-2-cyclopropyl-5-[(3R,4S)-4-(3-ethoxycarbonylphenyl)-3-methyl-1-piperidyl]tetrahydropyran-2-carboxylic acid (80 mg, 0.19 mmol), 2-(aminomethyl)-6-fluoro-4-(trifluoromethyl)phenol (50 mg, 0.22 mmol), N,N-diisopropylethylamine (260 mg, 2 mmol) in DMF (6 mL) was added HATU (100 mg, 0.26 mmol). The resulting solution was stirred at room temperature for 1 h. The reaction mixture was quenched with water, extracted with ethyl acetate and washed with brine. The organic layer was concentrated in vacuo and the residue was dissolved in toluene (10 mL) and treated with paraformaldehyde (600 mg, 20 mmol) and p-TsOH (150 mg, 0.87 mmol). The resulting mixture was stirred at 100° C. for 6 h. After cooling to room temperature, the mixture was diluted with EtOAc (25 mL) and washed with saturated aqueous NaHCO₃ solution (15 mL), brine (15 mL) and dried over MgSO₄. After filtration and concentration in vacuo, the residue was purified by preparative TLC (35% EtOAc in hexane as eluent) give 50 mg of ethyl 3-[(3R,4S)-1-[(3R,6S)-6-[8-chloro-6-(trifluoromethyl)-2,4-dihydro-1,3-benzoxazine-3-carbonyl]-6-cyclopropyl-tetrahydropyran-3-yl]-3-methyl-4-piperidyl]benzoate as a yellow foam that was used directly in the next step. MS: (ES) m/z calculated for $C_{33}H_{39}ClF_3N_2O_5$ [M+H]$^+$ 635.2, found 635.2.

Step b:

The ester prepared above (50 mg, 0.079 mmol) in MeOH (5 mL) and water (2 mL) was treated with LiOH monohydrate (210 mg, 5 mmol) at 60° C. for 3 h. This mixture was diluted with 2 N HCl and extracted with 10% MeOH in CH₂Cl₂ and dried over MgSO₄. After filtration and concentration in vacuo, the residue was purified by reverse phase HPLC (C18 column, acetonitrile-H₂O with 0.1% TFA as eluent) to give 40 mg of the title compound as an off-white solid. $^1$H NMR (400 MHz, CD₃OD) δ 7.96-7.84 (m, 2H), 7.61-7.53 (m, 2H), 7.45 (d, J=4.7 Hz, 2H), 6.17 (br, 1H), 5.88 (br, 1H), 4.98-4.90 (m, 1H), 4.45-4.35 (m, 1H), 3.70-3.37 (m, 4H), 3.35-3.05 (m, 4H), 2.85 (t, J=12.2 Hz, 1H), 2.65 (td, J=3.7, 13.9 Hz, 1H), 2.54 (dt, J=4.8, 11.2 Hz, 1H), 2.34-2.26 (m, 1H), 2.16-1.92 (m, 2H), 1.85-1.70 (m, 1H), 1.65-1.55 (m, 1H), 1.32-1.20 (m, 2H), 0.75 (d, J=6.7 Hz, 3H), 0.65-0.46 (m, 3H). MS: (ES) m/z calculated for $C_{31}H_{35}ClF_3N_2O_5$ [M+H]$^+$ 607.2, found 607.4.

Example 9

Synthesis of 5-[(3R,4S)-1-[(3R,6S)-6-cyclopropyl-6-[[3-fluoro-5-(trifluoromethyl)phenyl]methylcarbamoyl]tetrahydropyran-3-yl]-3-methyl-4-piperidyl]-2-fluoro-benzoic acid

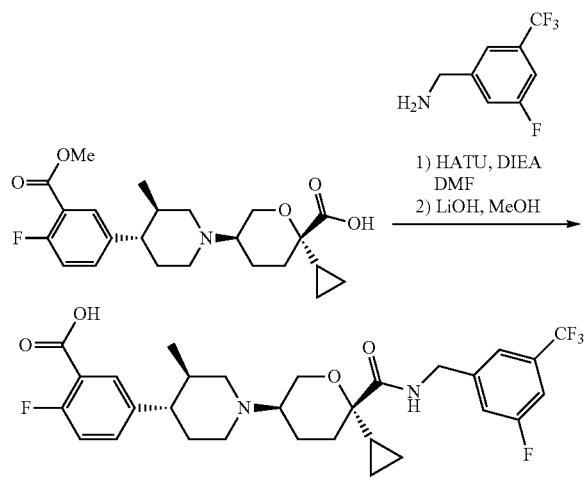

To a mixture of (2S,5R)-2-cyclopropyl-5-[(3R,4S)-4-(4-fluoro-3-methoxycarbonyl-phenyl)-3-methyl-1-piperidyl]tetrahydropyran-2-carboxylic acid (35 mg, 0.083 mmol), 3-fluoro-5-trifluoromethyl-benzylamine (40 mg, 0.2 mmol), and N,N-diisopropylethylamine (130 mg, 1 mmol) in DMF (5 mL) was added HATU (60 mg, 0.15 mmol). The resulting solution was stirred at room temperature for 1 h. The reaction mixture was quenched with water (5 mL), extracted with ethyl acetate (25 mL) and washed with brine (25 mL). The organic layer was concentrated in vacuo and the residue purified by preparative TLC (75% EtOAc in hexane as eluent) to give 50 mg of the intermediate ester. This was dissolved in MeOH (5 mL) and water (2 mL) and then treated with LiOH monohydrate (210 mg, 5 mmol). The resulting mixture was stirred at 60° C. for 3 h, diluted with 2 N HCl and extracted with 10% MeOH in CH$_2$Cl$_2$ and dried over MgSO$_4$. After filtration and concentration in vacuo, the residue was purified by reverse phase HPLC (C18 column, acetonitrile-H$_2$O with 0.1% TFA as eluent) to give 50 mg of the title compound as an off-white solid. $^1$H NMR (400 MHz, CD$_3$OD) δ 8.87 (t, J=6.3 Hz, 1H), 7.79 (dd, J=2.4, 6.9 Hz, 1H), 7.53-7.32 (m, 3H), 7.20 (dd, J=8.5, 10.6 Hz, 1H), 4.98-4.90 (m, 1H), 4.66 (dd, J=7.0, 15.6 Hz, 1H), 4.36 (dd, J=5.4, 15.6 Hz, 1H), 4.23-4.15 (m, 1H), 3.69-3.52 (m, 3H), 3.44-3.22 (m, 3H), 3.22-3.10 (m 1H), 2.87 (t, 0.1=12.0 Hz, 1H), 2.70-2.60 (m, 1H), 2.54 (dt, J=3.9, 11.8 Hz 1H), 2.30-2.20 (m, 1H), 2.10-1.86 (m, 3H), 1.75-1.57 (m, 2H), 1.17-1.05 (m, 1H), 0.78 (d, J=6.5 Hz, 3H), 0.70-0.46 (m, 3H). MS: (ES) m/z calculated for C$_{30}$H$_{34}$F$_5$N$_2$O$_4$ [M+H]$^+$ 581.2, found 581.4.

Example 10

Synthesis of 3-[(3R,4S)-1-[(3R,6S)-6-cyclopropyl-6-[4-[3-fluoro-5-(trifluoromethyl)phenyl]piperazine-1-carbonyl]tetrahydropyran-3-yl]-3-methyl-4-piperidyl]benzoic acid

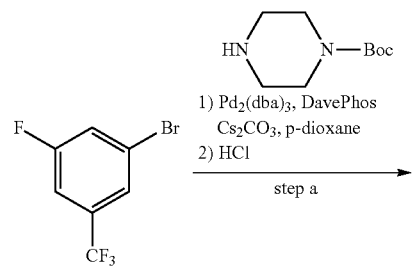

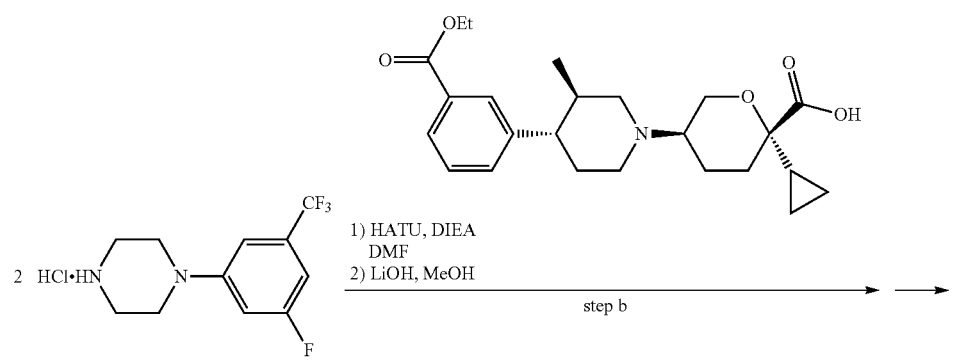

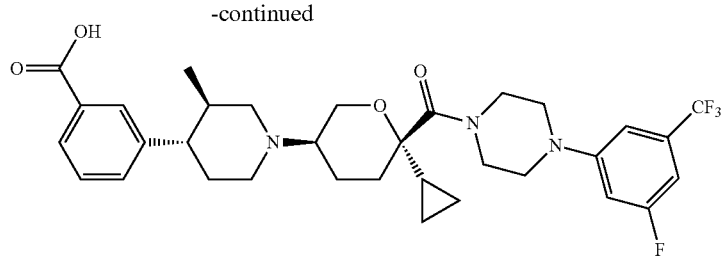

Step a:

To a mixture of 1-bromo-3-fluoro-5-(trifluoromethyl)benzene (1.0 g, 4.1 mmol), tert-butyl piperazine-1-carboxylate (1.0 g, 5.4 mmol), and Cs$_2$CO$_3$ (2.4 g, 7.4 mmol) in p-dioxane (10 mL) was added DavePhos (120 mg, 0.3 mmol). The resulting mixture was purged with nitrogen gas and then heated to 100° C. for 13 h. After cooling to room temperature, the reaction mixture was diluted with EtOAc and filtered through celite. The filtrate was concentrated in vacuo and the residue was purified by flash chromatography (2 to 25% ethyl acetate in hexane as eluent) to give 1.2 g of the intermediate Boc-piperazine. This was dissolved in CH$_2$Cl$_2$ (5 mL) and treated with 4N HCl in dioxane (6 mL, 24 mmol). After stirring at room temperature for 3 h, the solvent was concentrated in vacuo to give 1.2 g of 1-(3-fluoro-5-(trifluoromethyl)phenyl)piperazine dihydrochloride salt as a yellow solid, which was used directly in the next step. MS: (ES) m/z calculated for C$_{11}$H$_{13}$F$_4$N$_2$ [M+H]$^+$ 249.1, found 249.1.

Step b:

To a mixture of the piperazine di-HCl salt prepared above (60 mg, 0.19 mmol), (2S,5R)-2-cyclopropyl-5-[(3R,4S)-4-(3-ethoxycarbonylphenyl)-3-methyl-1-piperidyl]tetrahydropyran-2-carboxylic acid (75 mg, 0.18 mmol), and N,N-diisopropylethylamine (130 mg, 1 mmol) in DMF (5 mL) was added HATU (110 mg, 0.29 mmol). The resulting solution was stirred at room temperature for 1 h. The reaction was quenched with water, extracted with ethyl acetate and washed with brine. The organic layer was concentrated in vacuo and the residue purified by preparative TLC (75% EtOAc in hexane as eluent) to give 15 mg of the intermediate ester. This was dissolved in MeOH (5 mL) and water (2 mL) and then treated with LiOH monohydrate (210 mg, 5 mmol) at room temperature for 2 h, diluted with 2 N HCl, extracted with 10% MeOH in CH$_2$Cl$_2$ and dried over MgSO$_4$. After filtration and concentration in vacuo, the residue was purified by reverse phase HPLC (C18 column, acetonitrile-H$_2$O with 0.1% TFA as eluent) to give 12 mg of the title compound as an off-white solid. $^1$H NMR (400 MHz, CD$_3$OD) δ 7.97-7.85 (m, 2H), 7.51-7.42 (m, 2H), 7.08-6.94 (m, 2H), 6.82 (d, J=13.7 Hz, 1H), 4.38-4.30 (m, 2H), 4.30-4.14 (m, 4H), 3.90-3.55 (m, 5H), 3.48-3.05 (m, 4H), 2.92-2.82 (m, 1H), 2.66-2.49 (m, 2H), 2.27-1.98 (m, 4H), 1.85-1.72 (m, 1H), 1.60-1.50 (m, 1H), 1.25-1.18 (m, 1H), 0.95-0.82 (m, 1H), 0.78 (d, J=6.5 Hz, 3H), 0.74-0.60 (m, 2H), 0.50-0.42 (m, 1H). MS: (ES) m/z calculated for C$_{33}$H$_{40}$F$_4$N$_3$O$_4$ [M+H]$^+$ 618.3, found 618.3.

Example 11

Synthesis of (2S,5R)-2-cyclopropyl-N-[[3-fluoro-5-(trifluoromethyl)phenyl]methyl]-5-[4-hydroxy-4-(3-pyridyl)-1-piperidyl]tetrahydropyran-2-carboxamide

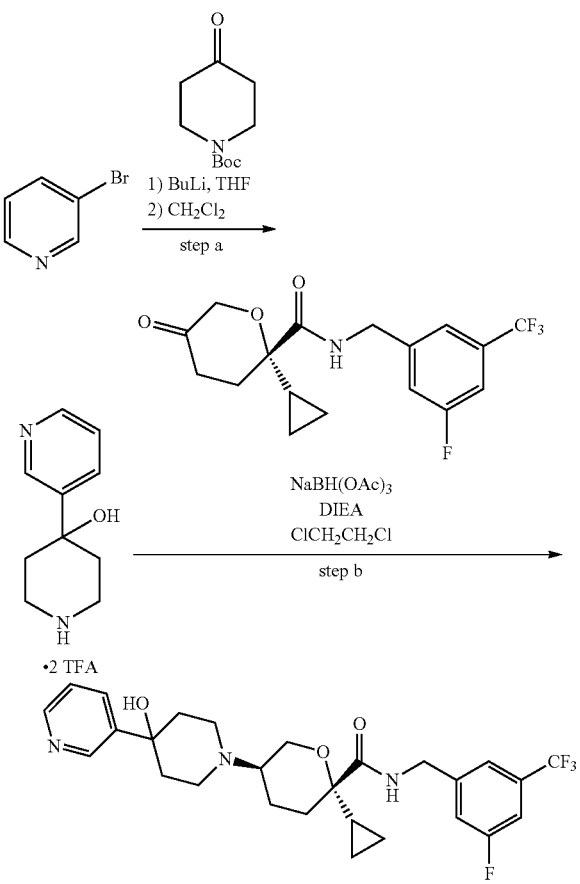

Step a:

To a −78° C. solution of 3-bromopyridine (1.58 g, 10 mmol) in 20 mL of THF was added BuLi (1.6M, 6.25 mL, 10 mmol). The resulting mixture was stirred at −78° C. for 20 min. A solution of 1-Boc-4-piperidone (1.99 g, 10 mmol) in THF (10 mL) was added dropwise. The reaction mixture was slowly warmed to room temperature overnight. The reaction was quenched with aqueous NH$_4$Cl (10 mL) and extracted with ether (100 mL). The combined organic was washed with brine and dried over MgSO$_4$. After concentration, the crude was purified by silica gel chromatography (20% EtOA in hexane) to gave a colorless oil (1.5 g, 50%), which was dissolved in CH$_2$Cl$_2$ (30 mL) and cooled to 0° C. 2.0 mL of TFA was added and the resulting mixture was stirred at room temperature for 4 hours before it was concentrated under reduced pressure to give a sticky oil (2.1 g, 95%), which was used in the next step without further purification.

Step b:

The TFA salt of the amine (202 mg, 0.5 mmol) was dissolved in 1,2-dichloroethane (2 mL) at room temperature followed by addition of iPr$_2$NEt (130 mg, 1 mmol). The resulting mixture was stirred at room temperature for 30 min. A solution of the ketone (104 mg, 0.3 mmol) in 1,2-dichloroethane (1.0 mL) was added followed by addition of NaBH(OAc)$_3$ (318 mg, 1.5 mmol). The resulting mixture was stirred at room temperature overnight. The reaction was quenched by addition of 5 mL of aqueous NaHCO$_3$ and extracted with 30 mL of CH$_2$Cl$_2$. The combined organic was washed with brine and dried over MgSO$_4$. After concentration, the crude was purified by reverse phase preparative HPLC to give the desired product (12 mg). $^1$H NMR (400 MHz, Chloroform-d) δ 8.75 (s, 1H), 7.37 (s, 1H), 7.22 (d, J=8.7 Hz, 2H), 7.00-6.84 (m, 2H), 4.69 (dd, J=15.6, 7.1 Hz, 1H), 4.42 (dd. J=15.6, 5.6 Hz, 1H), 3.91 (ddd, J=10.9, 4.4, 2.2 Hz, 1H), 3.35 (t, J=10.7 Hz, 1H), 3.08-2.68 (m, 4H), 2.69-2.56 (m, 1H), 2.50-1.96 (m, 6H), 1.98-1.88 (m, 1H), 1.75-1.69 (m, 2H), 1.55-1.35 (m, 2H), 1.12 (tt, J=8.5, 5.5 Hz, 1H), 0.61-0.35 (m, 4H). MS: (ES) m/z calculated for C$_{27}$H$_{32}$F$_4$N$_3$O$_3$ [M+1] 522.2, found 522.2.

Example 12

Synthesis of 2-[3-[[[(2S,5R)-2-cyclopropyl-5-[4-(4-fluorophenyl)-1-piperidyl]tetrahydropyran-2-carbonyl]amino]methyl]-5-(trifluoromethyl)phenoxy]acetic acid

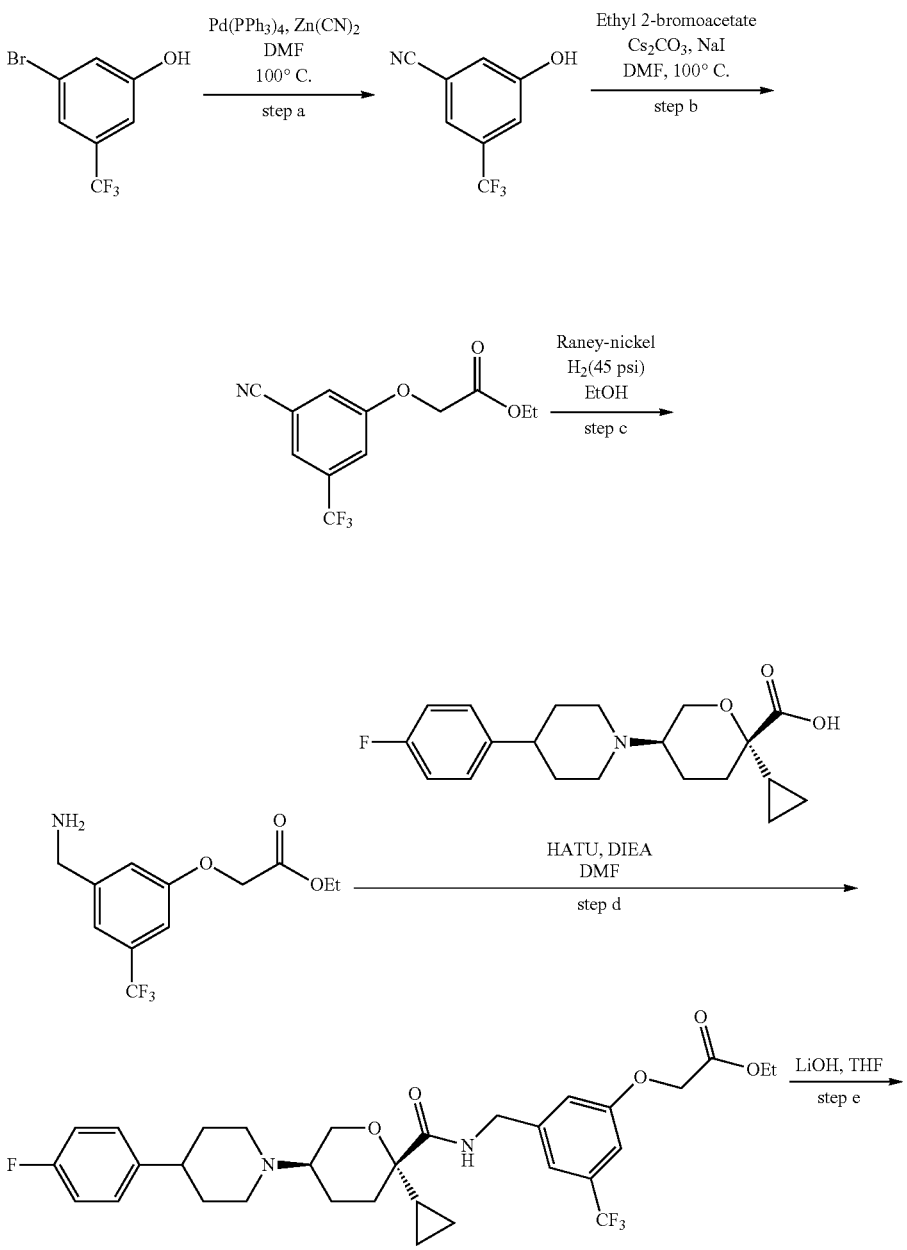

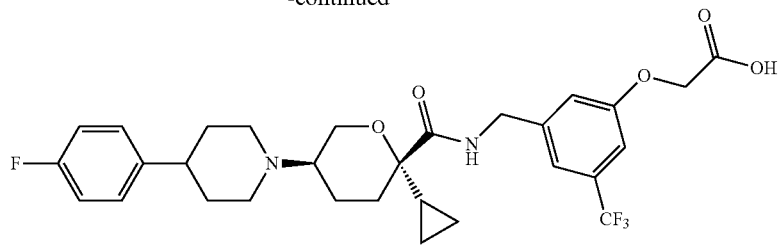

Step a:
To a solution of 3-bromo-5-trifluoromethylphenol (7.2 g, 30 mmol) in DMF (100 mL) was added Zn(CN)$_2$ (3.51 g, 30 mmol) and Pd(PPh$_3$)$_4$ (3.5 g, 6 mmol). The resulting mixture was stirred at 100° C. under nitrogen atmosphere for 4 hours. EtOAc (250 mL) was added and the mixture was washed with water (2×50 mL) and brine (100 mL) before it was dried over MgSO$_4$ and concentrated under reduced pressure. The residue was purified by silica gel chromatography (20% EtOA in hexane) to give a colorless oil (3.36 g, 60%).

Step b:
To a solution of 3-cyno-5-trifluoromethylphenol (1.87 g, 10 mmol) in DMF (20 mL) was added ethyl, 2-bromoacetate (2.5 g, 15 mmol), Cs$_2$CO$_3$ (6.5 g, 20 mmol) and NaI (1.5 g, 10 mmol). The resulting mixture was stirred at 100° C. overnight before it was cooled down to room temperature. EtOAc (250 mL) was added and the mixture was washed with water (2×50 mL) and brine (100 mL) before it was dried over MgSO$_4$ and concentrated under reduced pressure. The residue was purified by silica gel chromatography (10% EtOA in hexane) to give a colorless oil (2.18 g, 80%).

Step c:
To a solution of the cyanide (1.35 g, 5 mmol) in EtOH (20 mL) was added Raney-nickel slurry (1 mL) and NH$_4$OH (2 ml). The resulting suspension was stirred at room temperature under 45 psi of hydrogen for 4 hours. The reaction mixture was filtered through a pad of Celite and concentrated under reduced pressure to give a light blue oil (1.1 g) that was used in the next step without further purification.

Step d:
To a solution of (2S,5R)-2-cyclopropyl-5-[4-(4-fluoro-phenyl)-1-piperidyl]tetrahydropyran-2-carboxylic acid intermediate (52 mg, 0.149 mmol) in DMF (2 mL) was added the amine from step c (100 mg), triethylamine (0.5 ml) and HATU (190 mg). The resulting mixture was stirred at room temperature overnight. EtOAc (20 mL) was added and the mixture was washed with saturated aqueous NaHCO$_3$ (2×5 mL) and brine (5 mL). The combined organic was dried over MgSO$_4$ and concentrated under reduced pressure. The residue was purified by preparative TLC (100% EtOAc) to give the desired product (35 mg).

Step e:
A mixture of the ester (35 mg) in THF (1 mL) and 1N aqueous LiOH (1 mL) was stirred at room temperature overnight. 1N aqueous HCl was slowly added to adjust the pH of the mixture to 7.0 and then the mixture was extracted with 2:1 CHCl$_3$:iPrOH (20 mL). The organic was dried over MgSO$_4$ and concentrated under reduced pressure. The residue was purified using reverse phase HPLC to give the desired product (15 mg). $^1$H NMR (400 MHz, CD$_3$OD) δ 7.51 (brs, 1H), 7.40-7.30 (m, 2H), 7.24-7.18 (m, 2H), 7.02-6.95 (m, 2H), 4.55, 4.44 (ABq, J=15.4 Hz, 2H), 3.94 (ddd. J=11.2, 4.4, 2.2 Hz, 1H), 3.39 (t, J=11.0 Hz, 1H), 3.00-2.90 (m, 4H), 2.58-2.41 (m, 3H), 2.39-2.24 (m, 2H), 2.00-1.92 (m, 1H), 1.82-1.60 (m, 4H), 1.52 (td. J=13.5, 3.7 Hz, 1H), 1.40-1.26 (m, 1H), 1.10-1.02 (m, 1H), 0.70-0.64 (m, 1H), 0.57-0.49 (m, 1H), 0.46-0.30 (m, 3H). MS: (ES) m/z calculated for C$_{30}$H$_{35}$F$_4$N$_2$O$_5$ [M+H]$^+$ 579.2, found 579.6.

Synthesis of (2S,5R)-2-cyclopropyl-5-[4-(4-fluoro-3-methoxycarbonyl-phenyl)-1-piperidyl]tetrahydro-pyran-2-carboxylic acid

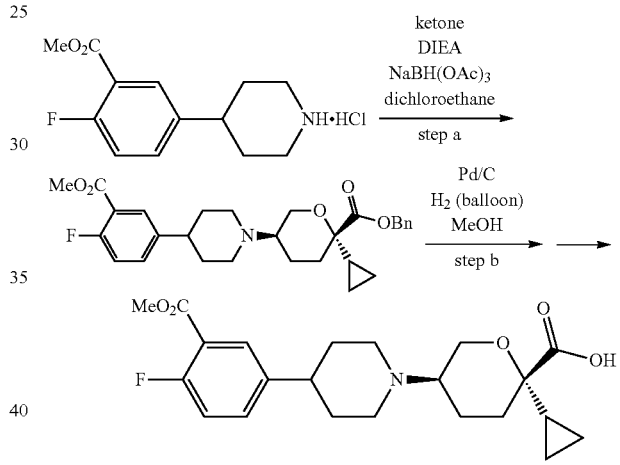

Step a:
2-Fluoro-5-piperidin-4-yl-benzoic acid methyl ester hydrochloride (5.0 g, 18 mmol, 1 equiv) and diisopropylethylamine (3.2 mL, 18.2 mmol, 1 equiv) in 1,2-dichloroethane (100 mL) was stirred at reflux until homogeneous. The solution was allowed to cool to room temperature and (2S)-2-Cyclopropyl-5-oxo-tetrahydro-pyran-2-carboxylic acid benzyl ester (5.0 g, 18.2 mmol, 1 equiv) was added followed by NaBH(OAc)$_3$ (7.7 g, 36.4 mmol, 2 equiv). This was stirred at room temperature for 2 days then neutralized with saturated aqueous NaHCO$_3$. The organic layer was separated, dried over MgSO$_4$, filtered and concentrated to give the crude.

Step b:
To the crude from step a (18.2 mmol) was added MeOH (100 mL) and 10% Pd/C (50% wet, 7.7 g, 3.6 mmol, 0.2 equiv). This was stirred under a balloon filled with H$_2$. When complete, the reaction was filtered through celite and the filter cake was rinsed with 1:1 MeOH:AcOH. The solution was then concentrated. The residue was diluted with acetone. The resulting white precipitate is filtered to give (2S,5R)-2-cyclopropyl-5-[4-(4-fluoro-3-methoxycarbonyl-phenyl)-1-piperidyl]tetrahydropyran-2-carboxylic acid (1.1 g, 15%) as the pure cis diastereomer.

Synthesis of 5-chloro-7-(trifluoromethyl)-1,2,3,4-tetrahydroisoquinoline

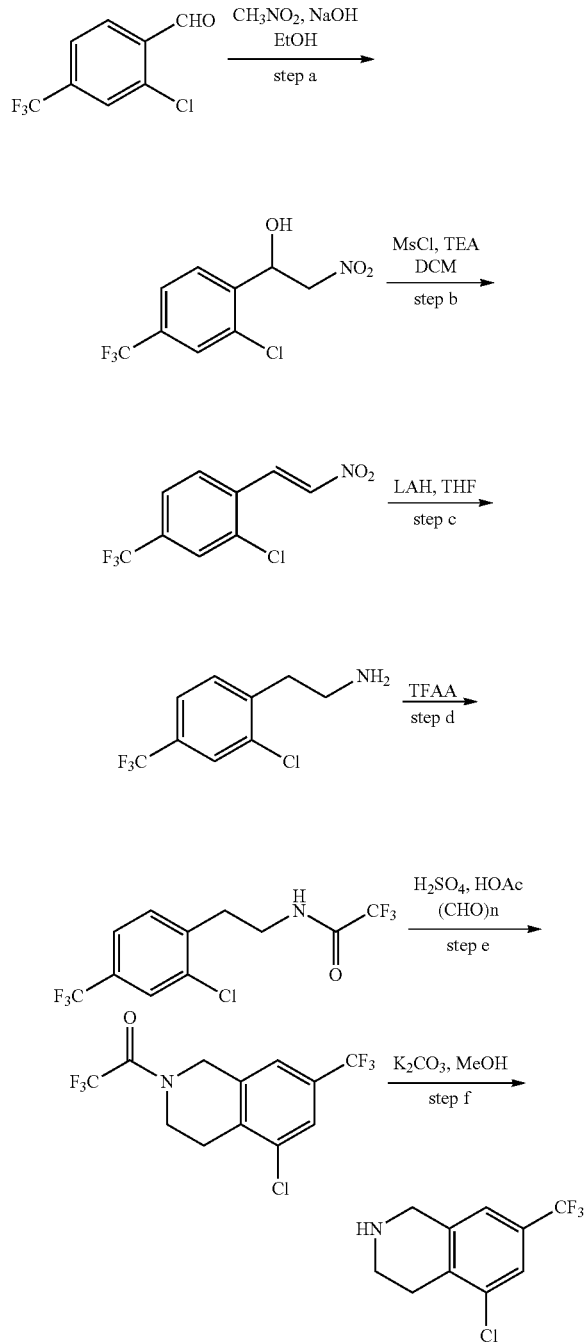

Step a:

To a 0° C. solution of 2-chloro-4-trifluoromethylbenzaldehyde (1.8 g, 9 mmol) in EtOH (20 mL) was added CH₃NO₂ (610 mg, 10 mmol). Aqueous NaOH (10M, 1 mL) was added dropwise and the resulting mixture was stirred at room temperature for one hour. The reaction was quenched with 1N HCl (10 mL) and extracted with EtOAc (200 mL). The combined organic was washed with aq. NaHCO₃ and brine before it was dried over MgSO₄ and concentrated under reduced pressure to give a colorless oil, which was used in the next step without further purification.

Step b:

The oil obtained from the previous step was dissolved in CH₂Cl₂ (20 mL) and the solution was cooled to 0° C. followed by addition of triethylamine (3.3 g, 30 mmol). MsCl (3.42 g, 30 mmol) was added dropwise and the resulting mixture was stirred at room temperature for 30 minutes before it was diluted with CH₂Cl₂ (200 mL). The combined organic was washed with aqueous NaHCO₃ and brine before it was dried over MgSO₄ and concentrated under reduced pressure. The residue was purified by silica gel chromatography (5% EtOAc in hexane) to give 1.35 g of the desired product as a yellow solid.

Step c:

To a 0° C. solution of product from the previous step (625 mg, 2.5 mmol) in THF (20 mL) was added dropwise a solution of LiAlH₄ in THF (1M, 8 mL). The resulting mixture was warmed to 50° C. for five hours. The mixture was cooled to 0° C. and slowly quenched with water followed by filtration through a pad of celite and washed with MTBE. The filtrate was dried and concentrated to give a colorless oil, which was used in the next step.

Step d:

The oil from step c was dissolved in CH₂Cl₂ (20 mL) and the solution was cooled to 0° C. Trifluoroacetic anhydride (630 mg, 3 mmol) was added dropwise followed by stirring at room temperature for one hour. The mixture was diluted with of CH₂Cl₂ (100 mL) and washed with aqueous NaHCO₃ and brine before it was dried over MgSO₄ and concentrated under reduced pressure. The residue was purified by silica gel chromatography (10% EtOAc in hexane) to give 600 mg of the desired product as a white solid.

Step e:

To a solution of TFA-protected amine from the previous step (1.0 g, 3.13 mmol) in a mixture of H₂SO₄ (4 mL) and HOAc (8 mL) was added paraformaldehyde (290 mg). The resulting mixture was stirred at room temperature for 72 hours before it was diluted with EtOAc (200 mL). The mixture was washed with water and brine and dried over MgSO₄ followed by concentration under reduced pressure. The residue was purified by silica gel chromatography (10% EtOAc in hexane) to give 300 mg of the desired product as a white solid.

Step f:

The solid from step e was dissolved in a mixture of MeOH (6 mL) and water (2 mL) followed by addition of K₂CO₃ (300 mg). The resulting mixture was stirred at room temperature overnight. 200 mL of CHCl₃:iPrOH (2:1) was added and the organic was separated and dried over MgSO₄ followed by concentration under reduced pressure. The residue was purified by silica gel chromatography (50% EtOAc in hexane) to give 190 mg of the desired product as a colorless oil.

Example 13

Synthesis of 5-[(3R,4S)-1-[(3R,6S)-6-[5-chloro-7-(trifluoromethyl)-3,4-dihydro-1H-isoquinoline-2-carbonyl]-6-cyclopropyl-tetrahydropyran-3-yl]-3-methyl-4-piperidyl]-2-fluoro-benzoic acid

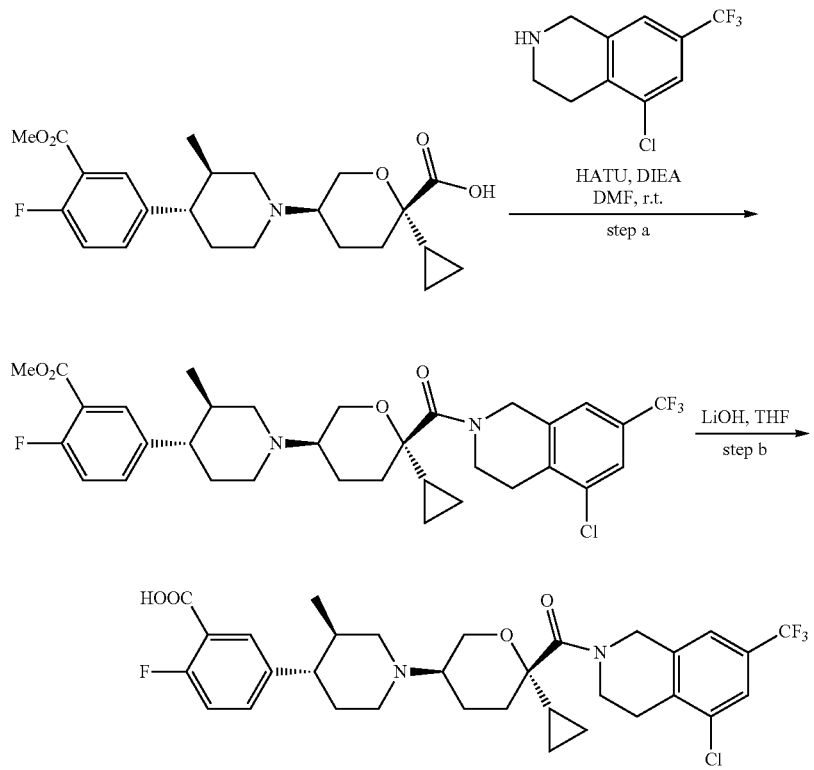

Step a:

To a solution of the acid intermediate (52 mg, 0.149 mmol) in DMF (2 mL) was added the amine (100 mg), triethylamine (0.5 ml) and HATU (190 mg). The resulting mixture was stirred at room temperature overnight. EtOAc (20 mL) was added and the mixture was washed with saturated aqueous $NaHCO_3$ (2×5 mL) and brine (5 mL). The combined organic was dried over $MgSO_4$ and concentrated under reduced pressure. The residue was purified by preparative TLC (100% EtOAc) to give 25 mg of the desired product.

Step b:

The product from step a was treated with aqueous LiOH in THF as previously described to give the final product (12 mg). $^1$H NMR (400 MHz, $CD_3OD$) δ 7.43-7.40 (m, 1H), 7.34-7.26 (m, 1H), 7.20-7.14 (m, 1H), 7.04-6.96 (m, 2H), 5.49-5.16 (m, 1H), 4.85-4.52 (m, 1H), 4.25-3.96 (m, 2H), 3.30-3.18 (m, 1H), 3.12-2.85 (m, 4H), 2.59-2.38 (m, 3H), 2.36-2.19 (m, 2H), 2.09-1.97 (m, 1H), 1.85-1.74 (m, 2H), 1.73-1.58 (m, 2H), 1.56-1.38 (m, 1H), 1.34-1.27 (m, 1H), 1.23-0.97 (m, 1H), 0.78 (d, J=6.5 Hz, 3H), 0.76-0.20 (m, 4H). MS: (ES) m/z calculated for $C_{32}H_{36}F_4ClN_2O_4$ [M+H]$^+$ 623.2, found 623.1.

Example 14

Synthesis of 3-[(3R,4S)-1-[(3R,6S)-6-[5-chloro-7-(trifluoromethyl)-3,4-dihydro-1H-isoquinoline-2-carbonyl]-6-cyclopropyl-tetrahydropyran-3-yl]-4-piperidyl]benzoic acid

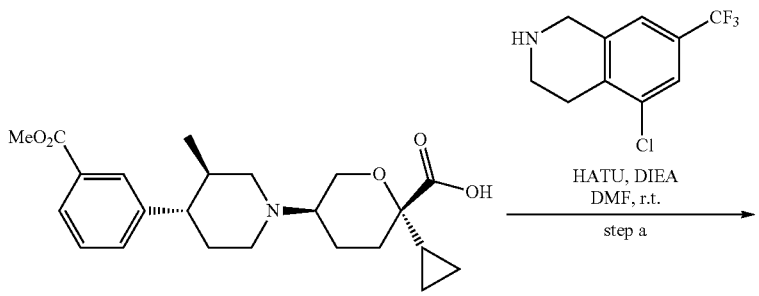

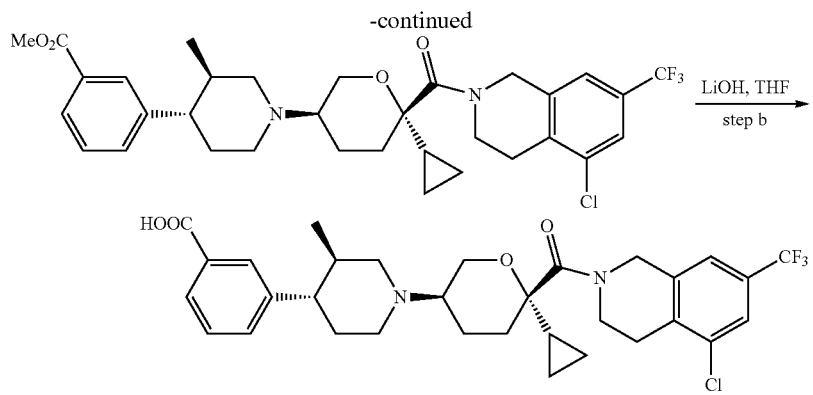

Step a:

To a solution of the acid intermediate (52 mg, 0.149 mmol) in DMF (2 mL) was added the amine (100 mg), triethylamine (0.5 ml) and HATU (190 mg). The resulting mixture was stirred at room temperature overnight. EtOAc (20 mL) was added and the mixture was washed with saturated aqueous NaHCO$_3$ (2×5 mL) and brine (5 mL). The combined organic was dried over MgSO$_4$ and concentrated under reduced pressure. The residue was purified by preparative TLC (100% EtOAc) to give 25 mg of the desired product.

Step b:

The product from step a was treated with aqueous LiOH in THF as previously described to give the final product (12 mg). $^1$H NMR $^1$H NMR (400 MHz, CD$_3$OD) δ 7.41-7.38 (m, 2H), 7.34-7.26 (m, 1H), 7.20-7.14 (m, 1H), 7.04-6.96 (m, 2H), 5.49-5.16 (m, 1H), 4.85-4.52 (m, 1H), 4.25-3.96 (m, 2H), 3.30-3.18 (m, 1H), 3.12-2.85 (m, 4H), 2.59-2.38 (m, 3H), 2.36-2.19 (m, 2H), 2.09-1.97 (m, 1H), 1.85-1.74 (m, 2H), 1.73-1.58 (m, 2H), 1.56-1.38 (m, 1H), 1.34-1.27 (m, 1H), 1.23-0.97 (m, 1H), 0.78 (d, J=6.5 Hz, 3H), 0.76-0.20 (m, 4H). MS: (ES) m/z calculated for C$_{32}$H$_{37}$F$_3$ClN$_2$O$_4$ [M+H]$^+$ 605.2, found 605.1.

Example 15

Synthesis of N-[[3,5-bis(trifluoromethyl)phenyl]methyl]-5-spiro[indene-1,4'-piperidine]-1'-yl-tetrahydropyran-2-carboxamide

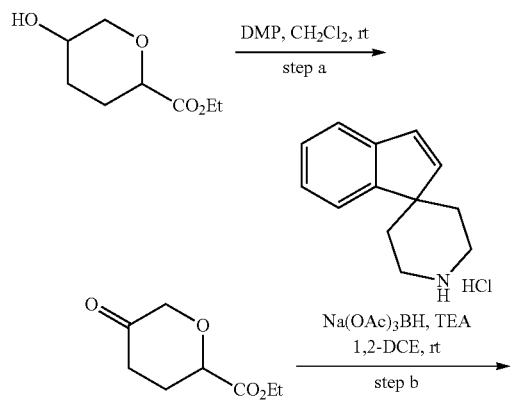

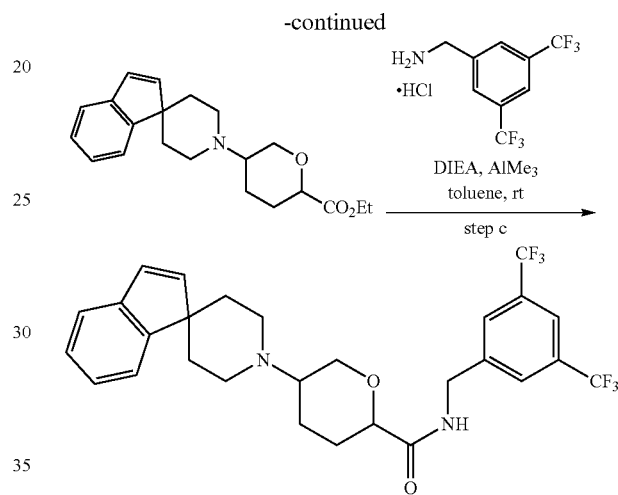

Step a:

Ethyl 5-hydroxytetrahydropyran-2-carboxylate (2.0 g, 11.5 mmol) was dissolved in anhydrous CH$_2$Cl$_2$ (80 mL) and Dess-Martin periodinane (7.3 g, 17.2 mmol) was added. The reaction mixture was stirred at rt overnight, then 10% Na$_2$S$_2$O$_3$ solution (50 mL) and saturated NaHCO$_3$ (50 mL) were added. The mixture was stirred for 15 min and the organic layer was separated, dried over MgSO$_4$, filtered and evaporated. The residue was diluted with Et$_2$O, white solid was filtered off and the filtrate was evaporated to give the crude product as a yellow oil (1.5 g, 76%).

Step b:

To a suspension of 4-spiroindene-piperidine hydrochloride (554 mg, 2.5 mmol) in anhydrous 1,2-dichloroethane (10 mL), triethylamine (0.35 mL, 2.5 mmol) was added and the mixture was stirred at rt for 15 min. The crude ketone from step a (400 mg, 2.3 mmol) was added followed by solid NaBH(OAc)$_3$ (0.97 g, 4.6 mmol). The reaction mixture was stirred at rt overnight, then H$_2$O (10 mL) and 2M K$_2$CO$_3$ (10 mL) were added. The organic layer was separated and the aqueous phase was further extracted with CH$_2$Cl$_2$ (2×15 mL). The combined organics were dried over MgSO$_4$, filtered and evaporated. The residue was purified by column chromatography (silica gel, CH$_2$Cl$_2$→10% MeOH in CH$_2$Cl$_2$) to give the product as a mixture of diastereomers (460 mg, 59%). MS: (ES) m/z calculated for C$_{21}$H$_{28}$NO$_3$ [M+H]$^+$ 342.2, found 342.1.

Step c:

To a suspension of 3,5-bis(trifluoromethyl)phenyl)-methanamine hydrochloride (195.7 mg, 0.7 mmol) in anhydrous toluene (1 mL). N,N-diisopropylethylamine (0.12 mL, 0.7 mmol) was added and the mixture was stirred at rt for 15 min. 2M AlMe₃ (0.7 mL, 1.4 mmol) was added dropwise and after 10 min., ester from step b (120 mg, 0.35 mmol) in anhydrous toluene (2 mL) was added. The mixture was stirred at rt overnight then H₂O (5 mL) and potassium tartrate (500 mg) were added. The organic layer was separated and the aqueous phase was further extracted with Et₂O. The combined organics were dried over MgSO₄, filtered and evaporated. The residue was purified by column chromatography (silica gel, CH₂Cl₂→1:1 CH₂Cl₂:EtOAc) and then by C18 HPLC to give the product as a mixture of diastereomers (75 mg, 33%). ¹H NMR (400 MHz, CDCl₃) δ 7.83-7.71 (m, 3H), 7.41-7.27 (m, 4H), 7.05 (t, J=6.3 Hz, 1H), 6.94-6.87 (m, 1H), 6.74-6.66 (m, 1H), 4.80-4.32 (m, 3H), 4.21-3.92 (m, 1H), 3.90-3.60 (m, 2H), 3.27-2.89 (m, 6H), 2.86-2.63 (m, 1H), 2.58-2.38 (m, 1H), 2.24-1.94 (m, 2H), 1.72-1.47 (m, 2H). MS: (ES) m/z calculated for C₂₈H₂₉F₆N₂O₂ [M+H]⁺ 539.2, found 539.2.

Example 16

Synthesis of (2S,5R)-5-[4-(4-fluorophenyl)-1-piperidyl]-2-isopropyl-N-[[5-(trifluoromethyl)-3-pyridyl]methyl]tetrahydropyran-2-carboxamide and (2R,5S)-5-[4-(4-fluorophenyl)-1-piperidyl]-2-isopropyl-N-[[5-(trifluoromethyl)-3-pyridyl]methyl]tetrahydropyran-2-carboxamide

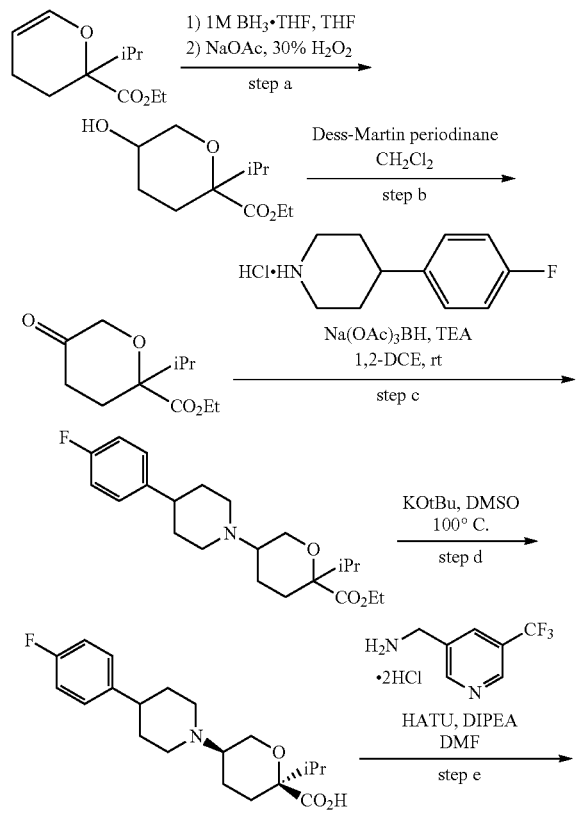

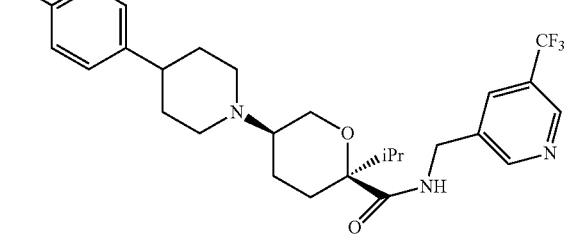

Step a:
2-Isopropyl-3,4-dihydro-2H-pyran-2-carboxylic acid ethyl ester (7.0 g, 35.0 mmol) was dissolved in anhydrous THF (100 mL) and cooled to −10° C., then 1M BH₃ in THF (75 mL, 75.0 mmol) was added dropwise. The reaction was kept at 4° C. overnight, then cooled to −10° C. and a solution of NaOAc (5.7 g, 70 mmol) in H₂O (15 mL) was slowly added. After 10 min. 35% H₂O₂ (10.2 mL, 105 mmol) was added and the reaction mixture was stirred at rt for 3 h. The reaction was diluted with brine (50 mL) and the organic layer was separated, dried over MgSO₄, filtered and evaporated. The residue was diluted with Et₂O (150 mL), white solid was filtered off and the filtrate was evaporated to give crude product as oil (7.5 g, 98%).

Step b:
The oxidation step was carried out analogously to example 15 to give a yellow oil, 96%.

Step c:
The reductive amination step was carried out analogously to example 15 to give the product as a mixture of diastereomers (52%). MS: (ES) m/z calculated for C₂₂H₃₃FNO₃ [M+H]⁺ 378.2, found 378.1.

Step d:
The product from Step c (4.6 g, 12.2 mmol) was dissolved in DMSO (25 mL) and KOtBu (3.4 g, 30.5 mmol) was added. The mixture was stirred at 100° C. for 20 min. then cooled down and diluted with H₂O (100 mL). AcOH (10 mL) and extracted with EtOAc (3×100 mL). The combined organics were dried over MgSO₄, filtered and evaporated. The residue was diluted with Et₂O (50 mL), white solid of the product ((rac)-cis diastereomer) was filtered off and dried under vacuum (600 mg, 14%). MS: (ES) m/z calculated for C₂₀H₂₉FNO₃ [M+H]⁺ 350.2, found 350.1.

Step e:
To the mixture of the acid from Step d (40 mg, 0.115 mmol), HATU (87 mg, 0.23 mmol) in anhydrous DMF (1 mL), diisopropylethylamine (0.1 mL, 0.575 mmol) was added. The mixture was stirred at rt for 15 min then 5-trifluoromethyl-pyridin-3-yl)-methylamine dihydrochloride (29 mg, 0.116 mmol) was added. The reaction was stirred at rt overnight, then diluted with H₂O (8 mL) and extracted with EtOAc (2×5 mL). The combined organics were dried over MgSO₄, filtered and evaporated. The residue was purified by preparative TLC (silica gel, 2:8 hexanes:EtOAc) to give the product as a (rac)-cis diastereomer (10 mg, 17%). ¹H NMR (400 MHz, CD₃OD) δ 8.85-8.76 (m, 2H), 8.14 (brs, 1H), 7.28-7.13 (m, 2H), 7.06-6.90 (m, 2H), 4.54, 4.49 (ABq, J=15.1 Hz, 2H), 3.97 (ddd, J=11.3, 4.6, 2.4 Hz, 1H), 3.35 (t, J=10.9 Hz, 1H), 3.00-2.83 (m, 2H), 2.57-2.21 (m, 5H), 2.01-1.92 (m, 1H), 1.88-1.58 (m, 5H), 1.44 (td, J=13.2, 3.6 Hz, 1H), 1.36-1.23 (m, 1H), 0.91 (d, J=6.9 Hz, 3H), 0.83 (d, J=6.9 Hz, 3H). MS: (ES) m/z calculated for C₂₇H₃₄F₄N₃O₂ [M+H]⁺ 508.3, found 508.0.

Example 17

Synthesis of (2S,5R)-2-cyclopropyl-5-[4-(4-fluorophenyl)-1-piperidyl]-N-[[3-fluoro-5-(trifluoromethyl)phenyl]methyl]tetrahydropyran-2-carboxamide

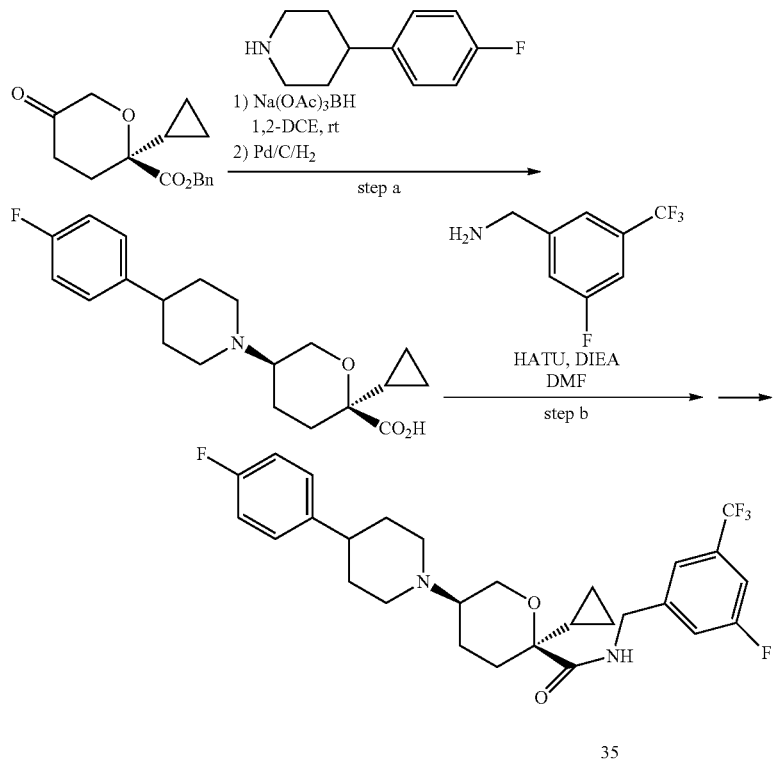

Step a:

To a solution of 4-(4-fluorophenyl)piperidine (3.3 g, 13.9 mmol) and benzyl (2S)-2-cyclopropyl-5-oxo-tetrahydropyran-2-carboxylate (4.0 g, 14.6 mmol) in anhydrous 1,2-dichloroethane (100 mL), solid NaBH(OAc)$_3$ (5.9 g, 27.8 mmol) was added. The reaction mixture was stirred at rt overnight, then H$_2$O (100 mL) and 2M K$_2$CO$_3$ (10 mL) were added. The organic layer was separated and the aqueous phase was further extracted with CH$_2$Cl$_2$ (2×50 mL). The combined organics were dried over MgSO$_4$, filtered and evaporated. The residue was re-dissolved in MeOH (100 mL) and 10% Pd/C (50% wet) (3 g, 1.4 mmol) was added under N$_2$. The reaction mixture was vigorously stirred under H$_2$ atmosphere (balloon) overnight, then filtered through celite and evaporated. The residue was diluted with acetone (15 mL) and Et$_2$O (15 mL). The product as white solid was filtered off, washed with Et$_2$O (15 mL) and dried under vacuum (850 mg, 15%). MS: (ES) m/z calculated for C$_{20}$H$_{27}$FNO$_3$ [M+H]$^+$ 348.2, found 348.4.

Step b:

The amide coupling step was carried out analogously to example 16 to give a yellowish solid, 52%. $^1$H NMR (400 MHz, CD$_3$OD) δ 7.51 (brs, 1H), 7.40-7.30 (m, 2H), 7.24-7.18 (m, 2H), 7.02-6.95 (m, 2H), 4.55, 4.44 (ABq, J=15.4 Hz, 2H), 3.94 (ddd, J=11.2, 4.4, 2.2 Hz, 1H), 3.39 (t, J=11.0 Hz, 1H), 3.00-2.90 (m, 2H), 2.58-2.41 (m, 3H), 2.39-2.24 (m, 2H), 2.00-1.92 (m, 1H), 1.82-1.60 (m, 4H), 1.52 (td, J=13.5, 3.7 Hz, 1H), 1.40-1.26 (m, 1H), 1.10-1.02 (m, 1H), 0.70-0.64 (m, 1H), 0.57-0.49 (m, 1H), 0.46-0.30 (m, 2H). MS: (ES) m/z calculated for C$_{28}$H$_{32}$F$_5$N$_2$O$_2$ [M+H]$^+$ 523.2, found 523.0.

Example 18

Synthesis of [(2S,5R)-2-cyclopropyl-5-[4-(4-fluorophenyl)-1-piperidyl]tetrahydropyran-2-yl]-[5-fluoro-7-(trifluoromethyl)-3,4-dihydro-1H-isoquinolin-2-yl]methanone

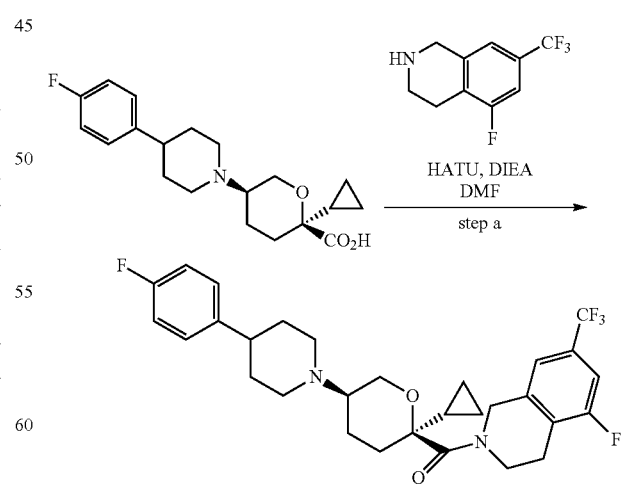

Step a:

The title compound was obtained by an amide coupling analogous to example 16 (18%). $^1$H NMR (400 MHz, CD$_3$OD) δ 7.38 (brs, 1H), 7.34-7.26 (m, 1H), 7.25-7.14 (m, 2H), 7.04-6.91 (m, 2H), 5.49 (brd, J=17.4 Hz, 0.5H), 5.16 (brd, J=17.3 Hz, 0.5H), 4.85-4.52 (m, 1H), 4.25-3.96 (m, 2H), 3.30-3.18 (m, 1H), 3.12-2.85 (m, 4H), 2.59-2.38 (m, 3H), 2.36-2.19 (m, 2H), 2.09-1.97 (m, 1H), 1.85-1.74 (m, 2H), 1.73-1.58 (m, 2H), 1.56-1.38 (m, 2H), 1.34-1.27 (m, 1H), 1.23-0.97 (m, 1H), 0.76-0.20 (m, 4H). MS: (ES) m/z calculated for C$_{30}$H$_{34}$F$_5$N$_2$O$_2$ [M+H]$^+$ 549.3, found 549.0.

Example 19

Synthesis of 5-[(2S)-4-[(3R,6S)-6-cyclopropyl-6-[6-(trifluoromethyl)-2,4-dihydro-1,3-benzoxazine-3-carbonyl]tetrahydropyran-3-yl]-2-methyl-piperazin-1-yl]-2-fluoro-benzoic acid Step a:

To a solution of t-butyl (3S)-3-methylpiperazine-1-carboxylate (10.0 g, 50.0 mmol) and methyl 5-bromo-2-fluoro-benzoate (11.6 g, 50 mmol) in anhydrous, degassed 1,4-dioxane (100 mL), anhydrous Cs$_2$CO$_3$ (24.4 g, 75.0 mmol) was added, followed by DavePhos (1.2 g, 3.0 mmol) and Pd$_2$(dba)$_3$ (2.3 g, 2.5 mmol). The reaction mixture was stirred under N$_2$, at 100° C. overnight, then cooled down to rt, filtered thought celite and evaporated. The residue was re-dissolved in EtOAc (200 mL), washed with 0.5M AcOH (2×100 mL), dried over MgSO$_4$, filtered and evaporated. Crude t-butyl (3S)-4-(4-fluoro-3-methoxycarbonyl-phenyl)-3-methyl-piperazine-1-carboxylate was dissolved in 1,4-dioxane (40 mL) and 4M HCl in 1,4-dioxane (40 mL). The reaction mixture was stirred at rt for overnight, then evaporated. The residue was diluted with saturated NaHCO$_3$ (100

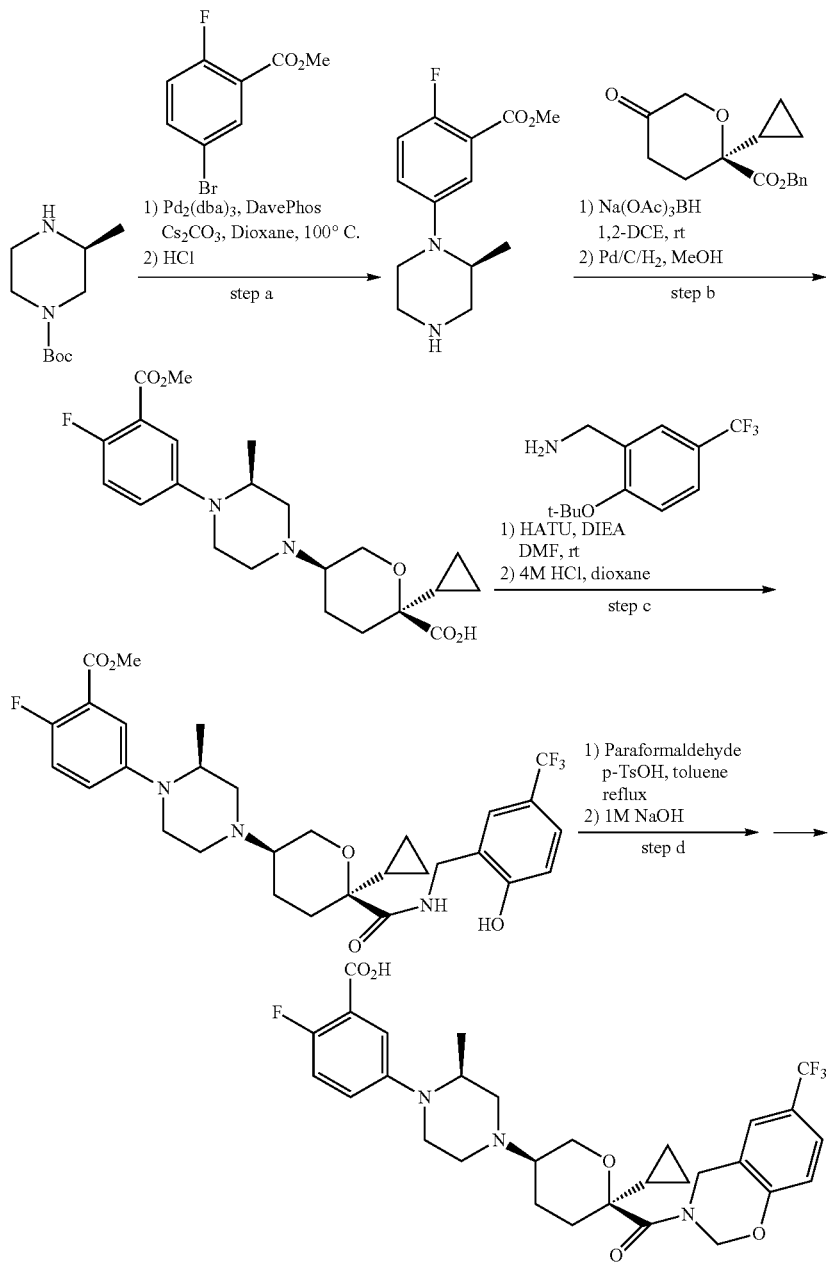

mL) and extracted with EtOAc (2×100 mL). The combined organics were dried over MgSO₄, filtered and evaporated. The crude product (5 g, 40%) was used without further purification.

Step b:

The reductive amination step and the acid synthesis were carried out analogously to example 17. The product was purified by column chromatography (silica gel, CH₂Cl₂→9:1 CH₂Cl₂:MeOH) to give yellow solid (32%). MS: (ES) m/z calculated for C$_{22}$H$_{30}$FN$_2$O$_5$ [M+H]$^+$ 421.2, found 421.0.

Step c:

To the mixture of the acid from Step b (150 mg, 0.36 mmol) and HATU (205 mg, 0.54 mmol) in anhydrous DMF (3 mL), diisopropylethylamine (0.19 mL, 1.1 mmol) was added. The mixture was stirred at rt for 15 min. then 2-t-butoxy-5-(trifluoromethyl)phenyl]methanamine (99 mg, 0.4 mmol) was added. The reaction was stirred at rt for overnight, then diluted with H₂O (8 mL) and extracted with EtOAc (2×5 mL). The combined organics were dried over MgSO₄, filtered and evaporated. The residue was dissolved in 1,4-dioxane (2 mL) and 4M HCl in 1,4-dioxane (2 mL) and stirred at rt for 1 h, then evaporated. The residue was diluted with saturated NaHCO₃ (10 mL) and extracted with EtOAc (3×5 mL). The combined organics were dried over MgSO₄, filtered and evaporated. The crude product (170 mg, 80%) was used without further purification.

Step d:

The mixture of the crude phenol from Step c (170 mg, 0.29 mmol), paraformaldehyde (900 mg) and p-TsOH.H₂O (300 mg) in toluene (10 mL) was stirred under reflux (Dean Stark apparatus) for 3 h, and then evaporated. The residue was diluted with saturated NaHCO₃ (10 mL) and extracted with EtOAc (3×5 mL). The combined organics were dried over MgSO₄, filtered and evaporated. The crude ester was dissolved in MeOH (2 mL) and 4M NaOH solution (0.5 mL, 1:1 MeOH:H₂O) was added. The mixture was stirred at rt for 2 h, and then AcOH (0.5 mL) was added. The reaction mixture was purified by C18 HPLC to give the product (52 mg, 22%). ¹H NMR (400 MHz, CD₃OD) δ 7.65 (s, 1H), 7.54 (s, 1H), 7.51-7.44 (m, 1H), 7.35 (s, 1H), 7.23-7.13 (m, 1H), 7.04 (d, J=8.6 Hz, 1H), 6.27-6.09 (m, 1H), 5.73-5.57 (m, 1H), 4.87-4.76 (m, 1H), 4.48-4.33 (m, 1H), 3.71-3.34 (m, 4H), 3.28-2.85 (m, 5H), 2.64 (dt, J=14.0, 3.7 Hz, 1H), 2.37-2.24 (m, 1H), 1.82-1.67 (m, 1H), 1.58 (td, J=13.2, 3.6 Hz, 1H), 1.35-1.14 (m, 2H), 1.05-0.85 (m, 3H), 0.72-0.36 (m, 4H). MS: (ES) m/z calculated for C$_{30}$H$_{34}$F$_4$N$_3$O$_5$ [M+H]$^+$ 592.2, found 592.0.

Example 20

Synthesis of 5-[(2S)-4-[(3R,6S)-6-cyclopropyl-6-[8-fluoro-6-(trifluoromethyl)-2,4-dihydro-1,3-benzoxazine-3-carbonyl]tetrahydropyran-3-yl]-2-methyl-piperazin-1-yl]-2-fluoro-benzoic acid

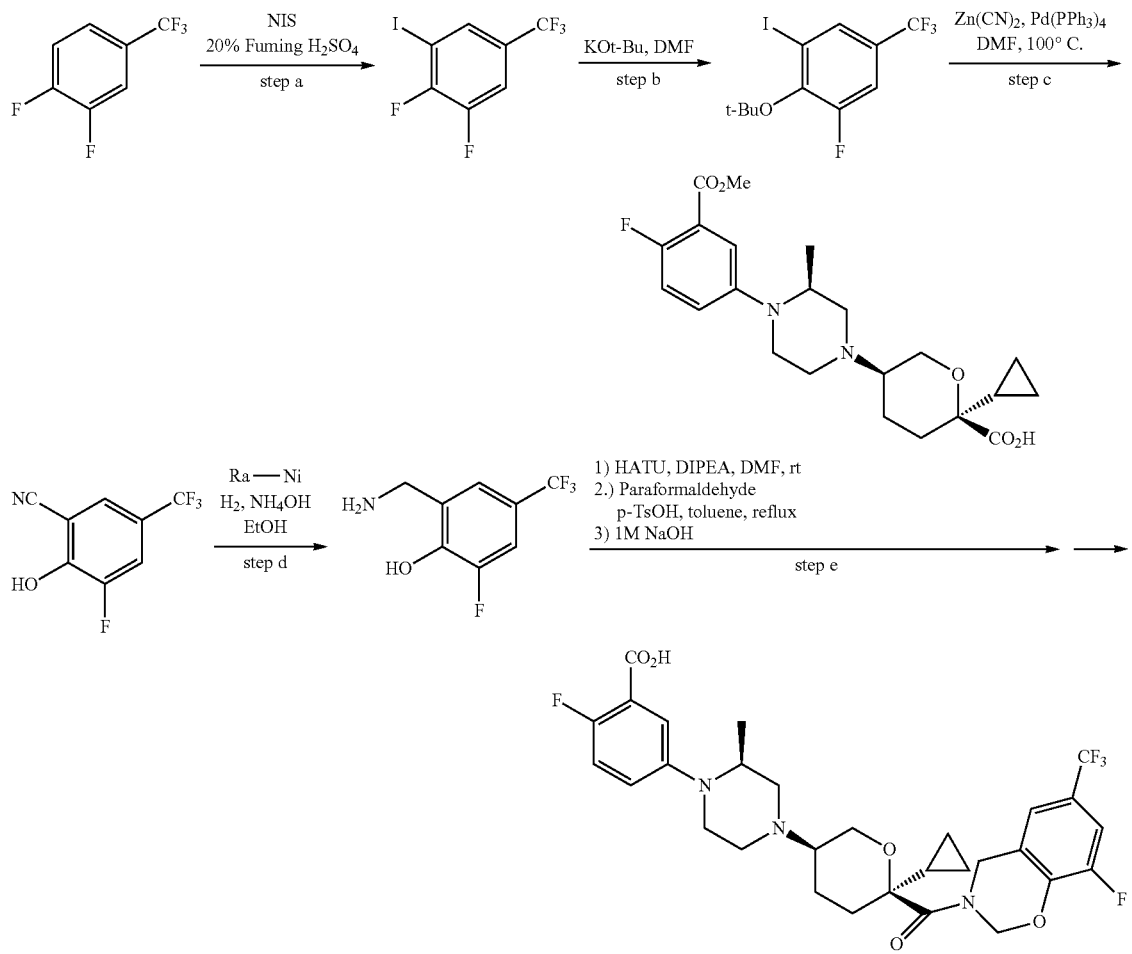

Step a:

To 20% fuming H₂SO₄ (100 mL) cooled to 0° C., 1,2-difluoro-4-(trifluoromethyl)benzene (52.0 g, 285.7 mmol) was added, followed by solid NIS (70.7 g, 314.3 mmol). The dark brown, thick mixture was stirred at 0° C. for 5 min., then slowly warmed up to rt, and stirred for 1 h. The reaction mixture was poured into ice and extracted with hexanes (2×300 mL). The combined organics were washed with 10% Na₂SO₃ solution, saturated NaHCO₃, and finally with brine. The organic layer was dried over MgSO₄, filtered and evaporated to give the crude product as a clear oil (74 g, 84%).

Step b:

To 1,2-difluoro-3-iodo-5-(trifluoromethyl)benzene from Step a (60.0 g, 194.8 mmol) in anhydrous DMF (200 mL) cooled to 0° C., solid KOtBu (24.0 g, 214.3 mmol) was added. The reaction was stirred at 0° C. for 30 min. then diluted with H₂O (1 L) and extracted with hexanes (3×300 mL). Combined organics were dried over MgSO₄, filtered and evaporated. The residue was purified by filtration through short silica-gel pad and washing with 10% EtOAc in hexanes to give a yellow oil (63 g, 89%).

Step c:

2-t-Butoxy-1-fluoro-3-iodo-5-(trifluoromethyl)benzene from Step b (30.0 g, 82.9 mmol) was dissolved in anhydrous, degassed DMF (200 mL), then Zn(CN)₂ (9.7 g, 82.9 mmol) was added followed by Pd(PPh₃)₄ (4.7 g, 4.1 mmol). The reaction mixture was stirred under N₂ at 100° C. for overnight, then diluted with H₂O (1 L) and extracted with Et₂O (2×300 mL). The combined organics were washed with 1M NaOH (2×80 mL) and then the aqueous layer was neutralized with 2M HCl and extracted using Et₂O (2×300 mL). The combined organics were dried over MgSO₄, filtered and evaporated to give the crude product as yellow oil (11 g, 65%) that was used without further purification.

Step d:

3-Fluoro-2-hydroxy-5-(trifluoromethyl)benzonitrile from Step c (11.0 g, 53.6 mmol) was dissolved in EtOH (50 mL) and 28% NH₄OH (5 mL) and Raney-nickel 2800 slurry in H₂O (3 mL) was added. The reaction mixture was shaken in a Parr apparatus under H₂ (50 psi) overnight and then filtered through celite and evaporated. The crude product was washed with Et₂O to give the product as a yellow solid (4.6 g, 41%). MS: (ES) m/z calculated for $C_8H_8F_4NO$ [M+H]⁺ 210.1, found 210.2.

Step e:

The title compound was obtained analogously to the previous examples (27%). ¹H NMR (400 MHz, CD₃OD) δ 7.69-7.60 (m, 1H), 7.46-7.28 (m, 3H), 7.18 (t, J=9.5 Hz, 1H), 6.40-6.14 (m, 1H), 5.85-5.63 (m, 1H), 5.11-4.92 (m, 1H), 4.51-4.31 (m, 1H), 3.71-3.36 (m, 4H), 3.28-2.74 (m, 6H), 2.65 (dt, J=13.4, 3.4 Hz, 1H), 2.40-2.24 (m, 1H), 1.83-1.67 (m, 1H), 1.59 (td. J=13.5, 3.8 Hz, 1H), 1.32-1.11 (m, 1H), 1.08-0.84 (m, 3H), 0.77-0.27 (m, 4H). MS: (ES) m/z calculated for $C_{30}H_{33}F_5N_3O_5$ [M+H]⁺ 610.2, found 610.0.

Example 21

Synthesis of 5-[1-[(3R,6S)-6-cyclopropyl-6-[8-fluoro-6-(trifluoromethyl)-2,4-dihydro-1,3-benzoxazine-3-carbonyl]tetrahydropyran-3-yl]-4-piperidyl]-2-fluoro-benzoic acid

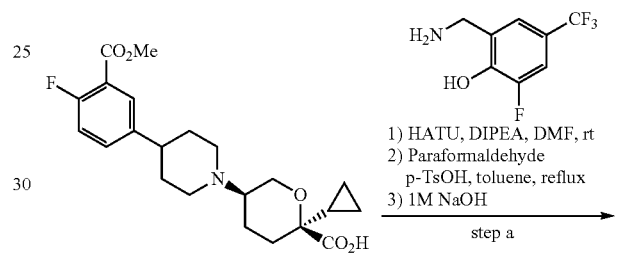

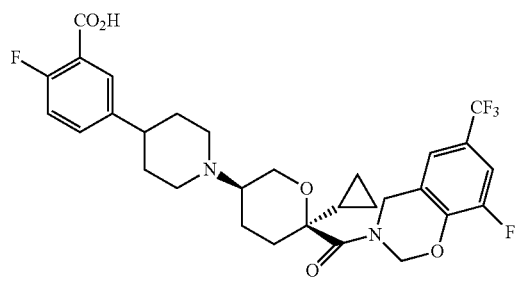

Step a:

The title compound was obtained analogously to the previous examples (42%). ¹H NMR (400 MHz, CD₃OD) δ 7.80 (dd, J=6.9, 2.5 Hz, 1H), 7.53-7.43 (m, 1H), 7.44-7.34 (m, 2H), 7.17 (dd, J=10.6, 8.5 Hz, 1H), 6.25 (brs, 1H), 5.72 (brs, 1H), 5.12-4.91 (m, 2H), 4.51-4.21 (m, 1H), 3.75-3.51 (m, 3H), 3.46-3.35 (m, 1H), 3.23-3.08 (m, 2H), 2.99-2.86 (m, 1H), 2.70-2.56 (m, 1H), 2.33-2.20 (m, 1H), 2.20-2.06 (m, 2H), 1.95-1.67 (m, 3H), 1.68-1.53 (m, 1H), 1.32-1.11 (m, 1H), 0.79-0.22 (m, 4H). MS: (ES) m/z calculated for $C_{30}H_{32}F_5N_2O_5$ [M+H]⁺ 595.2, found 595.0.

Example 22

Synthesis of 5-[(2S)-4-[(3R,6S)-6-cyclopropyl-6-[4-fluoro-7-(trifluoromethyl)-3,4-dihydro-1H-isoquinoline-2-carbonyl]tetrahydropyran-3-yl]-2-methyl-piperazin-1-yl]-2-fluoro-benzoic acid

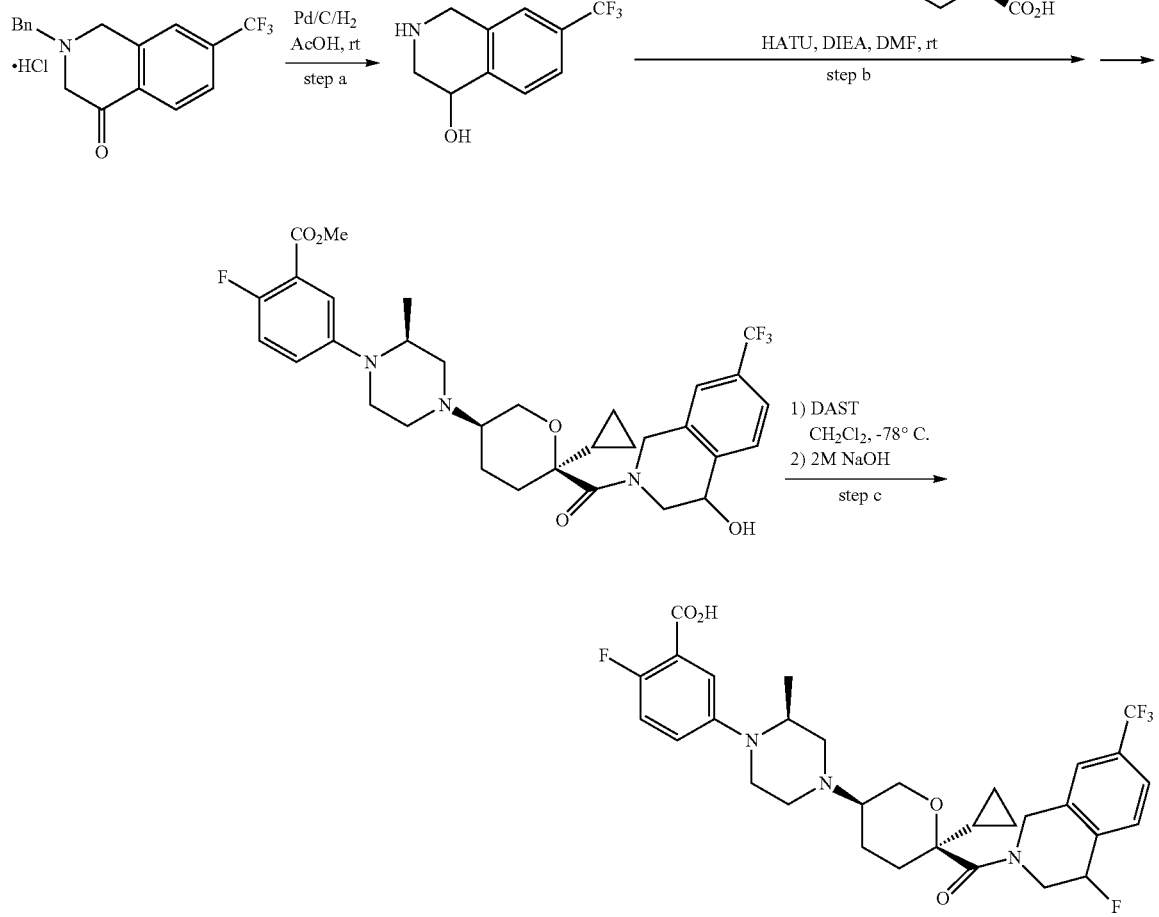

Step a:
2-Benzil-7-(trifluoromethyl)-1,3-dihydroisoquinolin-4-one (3.0 g, 8.8 mmol) was dissolved in AcOH (40 mL) and 10% Pd/C (50% wet) (1.9 g, 0.9 mmol) was added under $N_2$. The reaction mixture was vigorously stirred under $H_2$ atmosphere (balloon) overnight, then filtered through celite and evaporated. The residue was washed with $CH_3CN$ and $Et_2O$ to give a greenish solid (2 g, 90%). MS: (ES) m/z calculated for $C_{10}H_{11}F_3NO$ [M+H]$^+$ 218.1, found 218.0.

Step b:
The amide coupling step was carried out analogously to the previous examples (53%). MS: (ES) m/z calculated for $C_{32}H_{38}F_4N_3O_5$ [M+H]$^+$ 620.3, found 620.0.

Step c:
To the crude alcohol from Step b (111 mg, 0.18 mmol) in anhydrous $CH_2Cl_2$ (5 mL) cooled to −78° C., (diethylamino)sulfur trifluoride (94 μL, 0.72 mmol) was added and the reaction was stirred at −78° C. for 1 h. MeOH (1 mL) was added and the solvent was evaporated. The residue was dissolved in MeOH (1 mL) and 4M NaOH solution (1 mL, 1:1 MeOH:$H_2O$) was added. The mixture was stirred at rt for 1 h, and then AcOH (0.5 mL) was added. The reaction mixture was purified by C18 HPLC to give the product (15 mg, 10%). $^1$H NMR (400 MHz, $CD_3OD$) δ 7.73-7.63 (m, 4H), 7.42-7.29 (m, 1H), 7.22-7.12 (m, 1H), 5.94-5.58 (m, 2H), 5.52-5.25 (m, 1H), 4.50-4.22 (m, 1H), 3.80-3.36 (m, 3H), 3.26-2.80 (m, 7H), 2.68-2.56 (m, 2H), 2.35-2.20 (m, 1H), 1.86-1.46 (m, 2H), 1.35-0.30 (m, 8H). MS: (ES) m/z calculated for $C_{31}H_{35}F_5N_3O_4$ [M+H]$^+$ 608.3, found 608.0.

Synthesis of methyl 2-fluoro-5-[[(3R)-pyrrolidin-3-yl]amino]benzoate

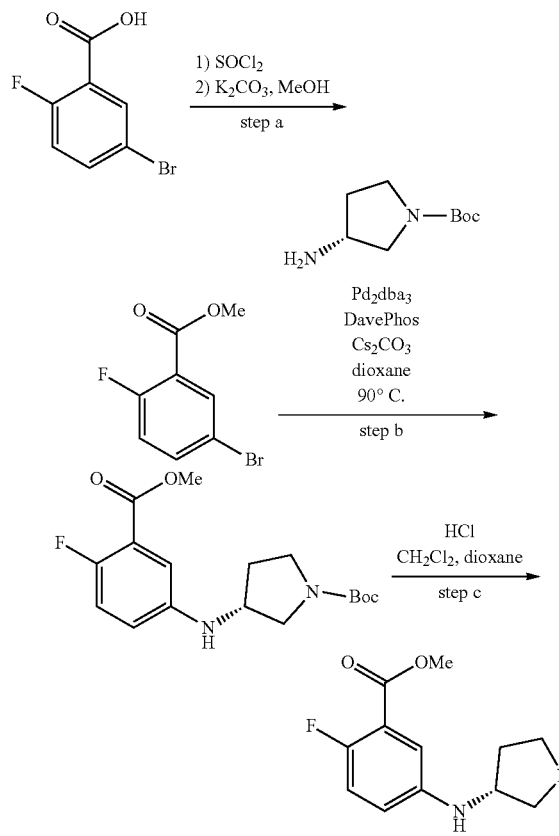

Step a:
To 5-bromo-2-fluoro-benzoic acid (6.38 g, 29.1 mmol, 1 equiv) was added thionyl chloride (10 mL, 290 mmol, 10 equiv). The mixture was stirred at 80° C. until complete, then concentrated. K$_2$CO$_3$ (10.87 g, 78.6 mmol, 2.7 equiv) was added, followed by MeOH (30 mL). This solution was stirred at room temperature. The reaction was filtered and the solid was rinsed with CH$_2$Cl$_2$. The organic was then washed with H$_2$O, dried over MgSO$_4$, filtered and concentrated to give the product (3.29 g, 14.1 mmol, 49%).

Step b:
To 5-bromo-2-fluoro-benzoic acid methyl ester (652 mg, 2.80 mmol, 1 equiv) was added Cs$_2$CO$_3$ (2.34 g, 7.18 mmol, 2.5 equiv) followed by 2-dicyclohexylphosphino-2'-(N,N-dimethylamino)biphenyl (132 mg, 0.335 mmol, 0.12 equiv), dioxane (6 mL), and (R)-3-Amino-pyrrolidine-1-carboxylic acid tert-butyl ester (0.695 mL, 3.37 mmol, 1.2 equiv). N$_2$ was bubbled through the mixture for 5 min, then Pd$_2$(dba)$_3$ was added to the reaction and N$_2$ was again bubbled through the mixture for 5 min. The reaction was then heated to 90° C. for 2 days. The reaction was allowed to cool to room temperature, then diluted with CH$_2$Cl$_2$, washed with H$_2$O (3×20 mL) then brine and dried over MgSO$_4$, filtered and concentrated to give the crude. This was purified by silica gel chromatography (hexanes/EtOAc) to give the product (328 mg, 0.969 mmol, 35%).

Step c:
To (R)-3-(4-Fluoro-3-methoxycarbonyl-phenylamino)-pyrrolidine-1-carboxylic acid tert-butyl ester (328 mg, 0.969 mmol) was added CH$_2$Cl$_2$ (1 mL) followed by 4 N HCl in dioxane (1 mL, 4 mmol). This was stirred overnight and then concentrated. The residue was partitioned between saturated NaHCO$_3$ and EtOAc. The layers were separated, then the aqueous layer was extracted with 2:1 CHCl$_3$:iPrOH (5×). This was then dried over Na$_2$SO$_4$, filtered and concentrated to give (R)-2-fluoro-5-(pyrrolidin-3-ylamino)-benzoic acid methyl ester (216 mg).

Example 23

Synthesis of 5-[[(3R)-1-[(3R,6S)-6-cyclopropyl-6-[6-(trifluoromethyl)-2,4-dihydro-1,3-benzoxazine-3-carbonyl]tetrahydropyran-3-yl]pyrrolidin-3-yl]amino]-2-fluoro-benzoic acid

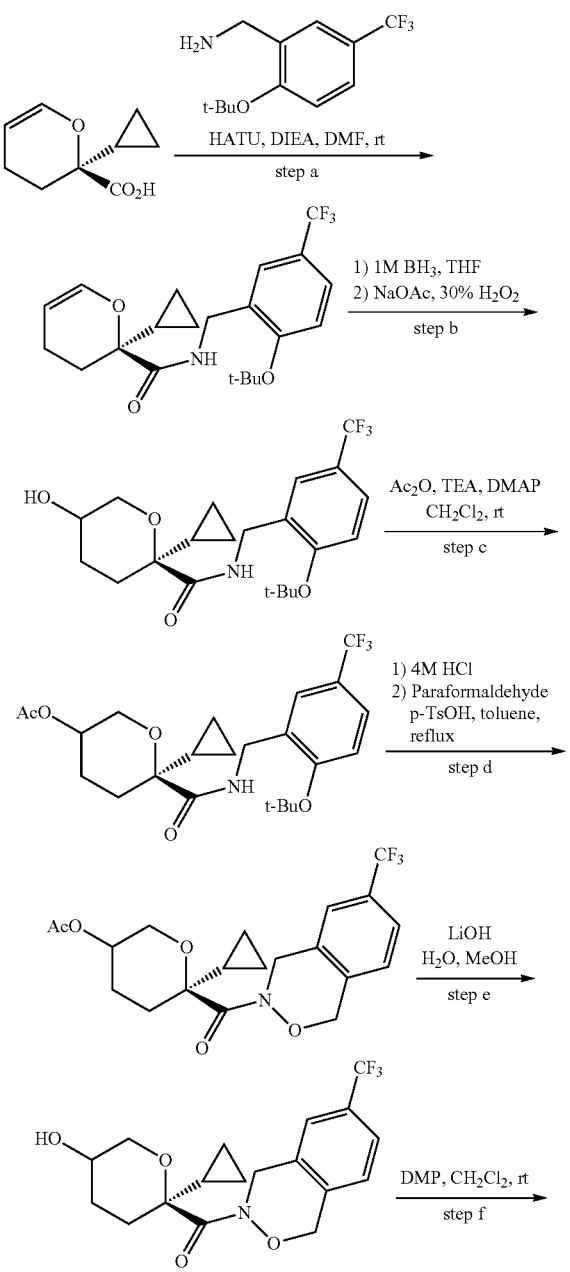

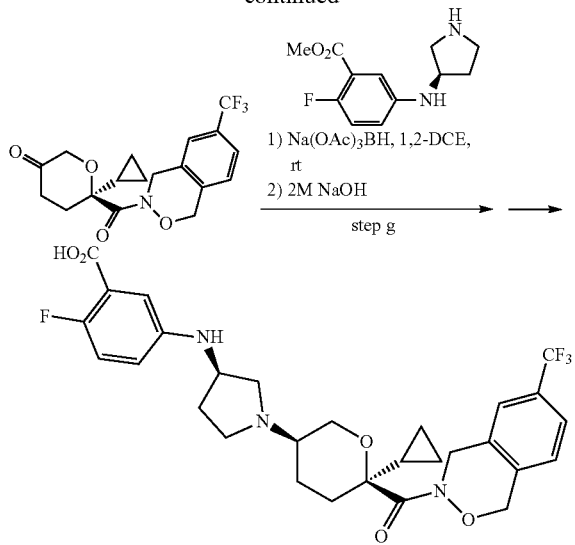

Step a:

To the mixture of (2S)-2-cyclopropyl-3,4-dihydropyran-2-carboxylic acid (6.5 g, 38.9 mmol) and HATU (16.3 g, 42.8 mmol) in anhydrous DMF (80 mL), diisopropylethylamine (13.5 mL, 77.8 mmol) was added and the mixture was stirred at rt for 15 min. Then a solution of the 2-t-butoxy-5-(trifluoromethyl)phenyl]methanamine (10.5 g, 42.8 mmol) in anhydrous DMF (20 mL) was added and the reaction was stirred at rt for 1 day. This was diluted with $H_2O$ (600 mL) and extracted using EtOAc (3×200 mL). The combined organic layers were washed with brine (4×50 mL), dried over $MgSO_4$, filtered and evaporated. The crude product was purified by column chromatography (silica gel, hexanes→9:1 hexanes:EtOAc) to give a white solid (10.4 g, 67%).

Step b:

The product from step a (10.0 g, 25.2 mmol) was dissolved in anhydrous THF (100 mL) and cooled to −10° C., then 1M $BH_3$ in THF (25.2 mL, 25.2 mmol) was added dropwise. The reaction was kept at 4° C. overnight, then cooled to −10° C. and a solution of NaOAc (4.1 g, 50.4 mmol) in $H_2O$ (15 mL) was slowly added. After 10 min, 35% $H_2O_2$ (7.6 mL, 75.6 mmol) was added and the reaction mixture was stirred at rt for 3 h. This was diluted with brine (50 mL) and the organic layer was separated, dried over $MgSO_4$, filtered and evaporated. The residue was diluted with $Et_2O$ (150 mL), a white solid was filtered off and the filtrate was evaporated to give crude product as oil (10.5 g, quant).

Step c:

To the product from Step b (10.4 g, 25.2 mmol) was added triethylamine (5.3 mL, 37.8 mmol) and DMAP (0.3 g, 2.5 mmol) in anhydrous $CH_2Cl_2$ (150 mL). Acetic anhydride (3.6 mL, 37.8 mmol) was added dropwise at rt and the mixture was stirred for 1 day. The reaction was washed with $H_2O$ (100 mL) then a saturated solution of $NaHCO_3$ (100 mL), and the organic layer was dried over $MgSO_4$, filtered and evaporated. Crude product was purified by column chromatography (silica gel, hexanes→7:3 hexanes:EtOAc) to give a yellow thick oil (8.0 g, 70%).

Step d:

The product from Step c (8.0 g, 17.5 mmol) was dissolved in anhydrous 1,4-dioxane (10 mL) and 4M HCl in 1,4-dioxane (30 mL); stirred at rt for 1 h then evaporated. The residue was dissolved in toluene (10 mL), then paraformaldehyde (20 g) and p-TsOH.$H_2O$ (332 mg) were added and the reaction was stirred under reflux (Dean Stark apparatus) for 2 h, and then evaporated. The residue was purified by column chromatography (silica gel, hexanes→7:3 hexanes:EtOAc) to give a yellow thick oil (6.2 g, 86%).

Step e:

The product from Step d (6.2 g, 15.0 mmol) was dissolved in MeOH (70 mL) and solution of LiOH.$H_2O$ (3.1 g, 75 mmol) in $H_2O$ (35 mL) was added. The reaction mixture was stirred at rt for 2 h, then neutralized to pH=7 with 2M AcOH and evaporated. The residue was diluted with brine (100 mL), extracted using $CH_2Cl_2$ (3×50 mL) and combined organic layer were dried over $MgSO_4$, filtered and evaporated to give white solid (5.3 g, 95%).

Step f:

The oxidation step was carried out analogously to the previous examples to give a yellow oil (quant).

Step g:

To the product from Step f (150 mg, 0.4 mmol) and methyl 2-fluoro-5-[[(3R)-pyrrolidin-3-yl]amino]benzoate (98 mg, 0.4 mmol) in anhydrous 1,2-dichloroethane (5 mL), $NaBH(OAc)_3$ (174 mg, 0.8 mmol) was added. The reaction mixture was stirred at rt for overnight then washed with saturated solution of $NaHCO_3$ (10 mL). The organic layer was separated, dried over $MgSO_4$, filtered and evaporated. The residue was dissolved in MeOH (1 mL) and 4M NaOH solution (1 mL, 1:1 MeOH:$H_2O$) was added. The mixture was stirred at rt for 1 h, and then AcOH (0.5 mL) was added. The reaction mixture was purified by C18 HPLC to give the product (39 mg, 12%). $^1$H NMR (400 MHz, $CD_3OD$) δ 7.57-7.40 (m, 2H), 7.14-6.95 (m, 3H), 6.86-6.77 (m, 1H), 6.27-6.07 (m, 1H), 5.69-5.54 (m, 1H), 4.38-4.10 (m, 2H), 3.57-3.34 (m, 2H), 2.63-2.51 (m, 2H), 2.29-2.16 (m, 2H), 2.15-1.90 (m, 2H), 1.80-1.62 (m, 2H), 1.55 (td, J=13.3, 3.8 Hz, 2H), 1.30-1.09 (m, 2H), 0.72-0.36 (m, 5H). MS: (ES) m/z calculated for $C_{29}H_{32}F_4N_3O_5$ [M+H]$^+$ 578.2, found 577.9.

Example 24

Synthesis of 3-[(2S)-4-[(3R,6S)-6-cyclopropyl-6-[6-(trifluoromethyl)-2,4-dihydro-1,3-benzoxazine-3-carbonyl]tetrahydropyran-3-yl]-2-methyl-piperazin-1-yl]propanoic acid

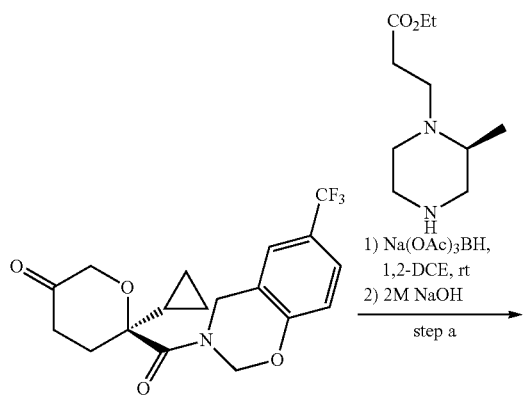

-continued

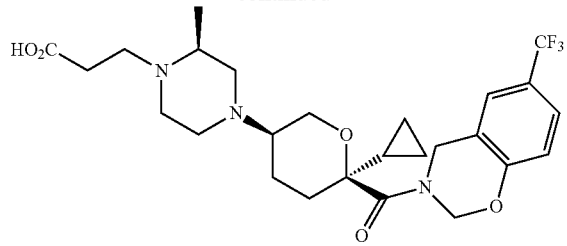

Step a:
The title compound was obtained analogously to the previous examples but using ethyl 3-[(2S)-2-methylpiperazin-1-yl]propanoate (7.5%). $^1$H NMR (400 MHz, CD$_3$OD) δ 7.56-7.43 (m, 2H), 7.05-6.97 (m, 1H), 6.22-6.06 (m, 1H), 5.80-5.61 (m, 1H), 4.16-3.98 (m, 1H), 3.60-3.39 (m, 2H), 3.27-2.87 (m, 8H), 2.79-2.57 (m, 4H), 2.57-2.41 (m, 2H), 2.05-1.91 (m, 1H), 1.54-1.39 (m, 2H), 1.32 (d, J=6.4 Hz, 3H), 1.22-1.06 (m, 1H), 0.70-0.33 (m, 4H). MS: (ES) m/z calculated for C$_{26}$H$_{35}$F$_3$N$_3$O$_5$ [M+H]$^+$ 526.3, found 526.0.

Example 25

Synthesis of 5-[(2S)-4-[(3R,6S)-6-cyclopropyl-6-[8-ethoxy-6-(trifluoromethyl)-2,4-dihydro-1,3-benzoxazine-3-carbonyl]tetrahydropyran-3-yl]-2-methyl-piperazin-1-yl]-2-fluoro-benzoic acid

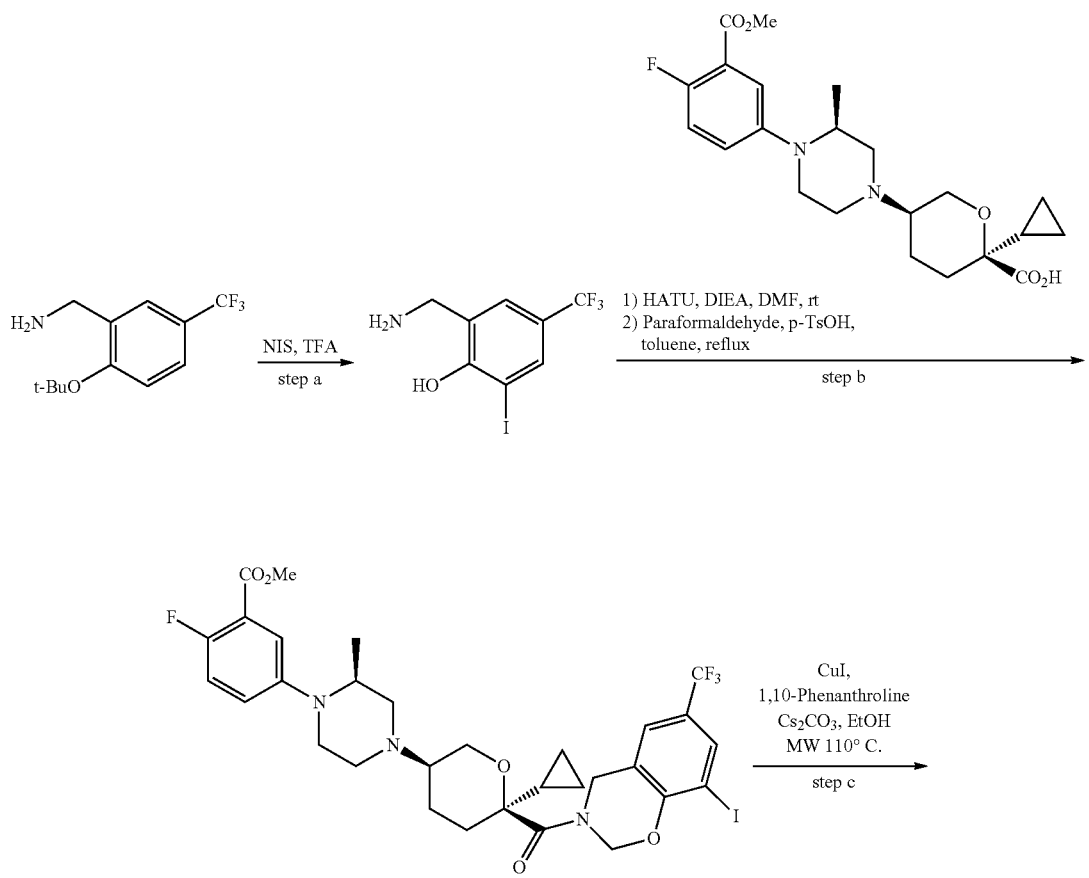

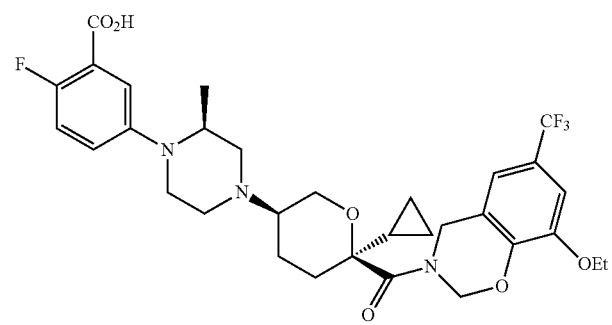

Step a:

To a solution of 2-tert-butoxy-5-(trifluoromethyl)phenyl]methanamine (4.0 g, 16.2 mmol) in TFA (20 mL), N-iodosuccinimide (4.4 g, 19.4 mmol) was added and the reaction was stirred at rt for 30 min. This was evaporated, then the residue was dissolved in EtOAc (250 mL) and washed with saturated solution of NaHCO$_3$ (50 mL) then 10% Na$_2$SO$_3$ (50 mL). The organic layer was dried over MgSO$_4$, filtered and evaporated to give a yellow solid (4.8 g, 93%).

Step b:

Step b was carried out analogously to the previous examples to give a yellow solid (90%). MS: (ES) m/z calculated for C$_{31}$H$_{35}$F$_4$IN$_3$O$_5$ [M+H]$^+$ 732.2, found 732.2.

Step c:

The product from Step b (100 mg, 0.14 mmol), 1,10-phenanthroline (13 mg, 0.07 mmol), CuI (13 mg, 0.07 mmol) and Cs$_2$CO$_3$ (91 mg, 0.28 mmol) were placed in a microwave vial and diluted with anhydrous EtOH (3 mL). The reaction was carried out in a microwave reactor at 110° C. for 1 h, then AcOH (1 mL) was added and reaction mixture was purified by C18 HPLC to give the product (12 mg, 10%). $^1$H NMR (400 MHz, CD$_3$OD) δ 7.78-7.59 (m, 1H), 7.45-7.27 (m, 1H), 7.25-7.03 (m, 3H), 6.32-6.15 (m, 1H), 5.69-5.51 (m, 1H), 4.83-4.72 (m, 1H), 4.51-4.34 (m, 1H), 4.10 (q, J=7.0 Hz, 2H), 3.70-3.36 (m, 4H), 3.27-2.82 (m, 5H), 2.64 (dt, J=13.7, 3.6 Hz, 1H), 2.37-2.25 (m, 1H), 1.83-1.66 (m, 1H), 1.59 (td, J=13.4, 3.7 Hz, 1H), 1.42 (t, J=7.0 Hz, 3H), 1.39-1.14 (m, 2H), 1.07-0.85 (m, 3H), 0.73-0.37 (m, 4H). MS: (ES) m/z calculated for C$_{32}$H$_{38}$F$_4$N$_3$O$_6$ [M+H]$^+$ 636.3, found 636.0.

Synthesis of methyl 3-[(3R,4S)-3-methyl-4-piperidyl]benzoate

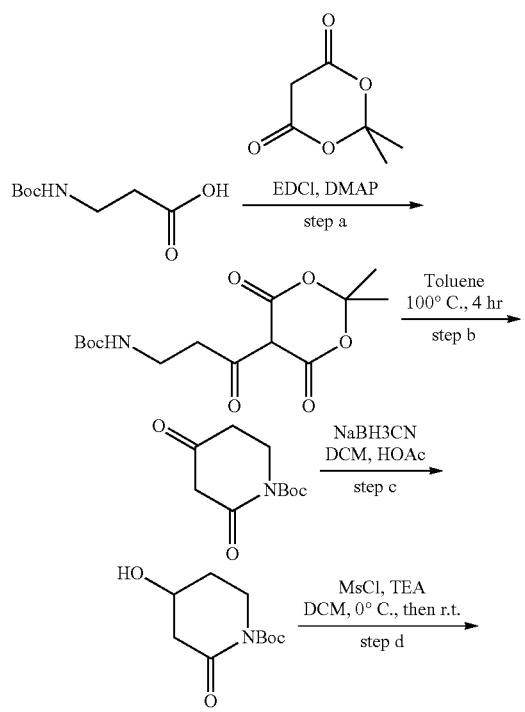

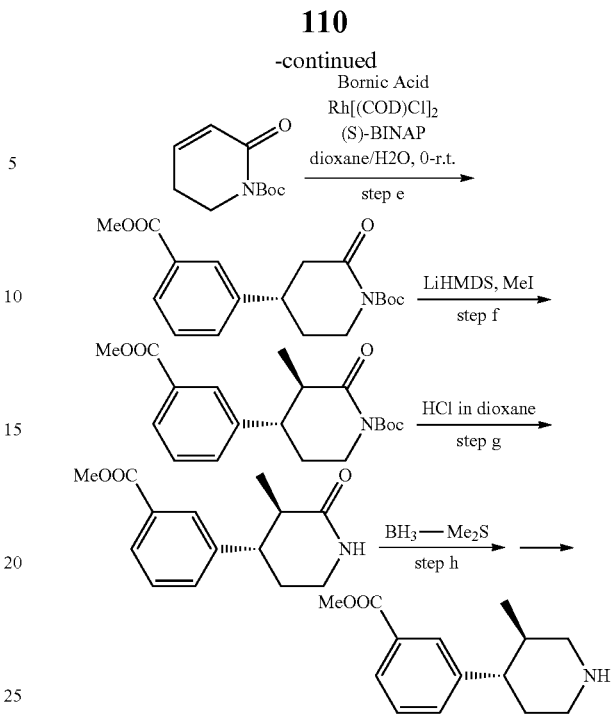

Step a:

EDCI (191.7 g, 1.0 mol) was added to an ice bath cooled solution of 3-(tert-butoxycarbonylamino)propanoic acid (189.2 g, 1.0 mol), meldrum's acid (144.1 g, 1.0 mol) and DMAP (135.0 g, 1.1 mol) in DMF (400 mL). The resulting reaction was allowed to stir at room temperature overnight. The reaction was quenched with 200 mL of H$_2$O. The resulting mixture was added dropwise to H$_2$O (2.0 L) while being mechanically stirred. The resulting solid was filtered and washed thoroughly with water until pH ~7 to give the product (283 g, 90% yield). $^1$H NMR (300 MHz, CDCl$_3$): δ 4.9 (bs, 1H), 3.55 (q, 2H), 3.45-3.25 (t, 3H), 1.75 (s, 6H), 1.4 (s, 9H).

Step b:

A solution of tert-butyl-3-(2,2-dimethyl-4,6-dioxo-1,3-dioxan-5-yl)-3-oxopropylcarbamate (100 g, 317.46 mmol) in toluene (1500 mL) was heated at 100° C. for 4 hours. The reaction was cooled to room temperature and concentrated under reduced pressure to afford the crude product. Purification by MTBE-trituration gave the product (56 g, 83% yield). $^1$H NMR (300 MHz, CDCl$_3$): δ 4.1 (t, 2H), 3.5 (s, 2H), 2.6 (t, 2H), 1.55 (s, 9H).

Step c:

tert-Butyl 2,4-dioxopiperidine-1-carboxylate (106.5 g, 500 mmol) was dissolved in CH$_2$Cl$_2$ (1.0 L) and HOAc (60 mL). The resulting solution was cooled to 0° C., then NaBH$_3$CN (37.8 g, 600 mmol) was added in portions. After stirring at room temperature overnight, the reaction mixture was cooled to 0° C. and aqueous NH$_4$OH was slowly added to adjust the pH to 9. The organic phase was separated and washed with brine (2×400 mL) then dried over MgSO$_4$, filtered and concentrated to give the product as a sticky oil.

Step d:

The product from step c was dissolved in CH$_2$Cl$_2$ (1.0 L) and the solution was cooled to 0° C. Triethylamine (151.5 g, 1.5 mol) was added and the resulting mixture was stirred at 0° C. for 30 minutes. Acetic anhydride (53.5 g, 525 mmol) was added dropwise. After stirring at room temperature overnight, water (400 ml) was added and the organic layer was separated and washed with a 5% KHSO$_4$ solution (3×300 mL). The organic phase was dried over MgSO$_4$ and then concentrated under reduced pressure. The residue was passed through a short pad of SiO$_2$ (500 g) and washed with 20% of EtOA in hexanes. The combined organic was concentrated to give the product (69 g) as a colorless oil which was directly used in the next step without further purification.

Step e:
Chloro(1,5-cyclooctadien)rhodium(I) dimer (493 mg, 1 mmol) and (S)-BINAP (1.56 g, 2.5 mmol) were added to a mixture of 3-methoxycarbonylphenylboronic acid (9.0 g, 50 mmol) in dioxane (65 mL). The resulting mixture was stirred at room temperature under nitrogen atmosphere for 1 hour. The mixture was cooled to 0° C. and H$_2$O (10 mL) was added, followed by 6-oxo-3,6-dihydro-2H-pyridine-1-carboxylic acid tert-butyl ester (9.3 g, 47.5 mmol) in dioxane (5 mL) and triethylamine (4.8 g, 47.5 mmol). The resulting mixture was stirred at room temperature overnight under nitrogen atmosphere. The mixture was diluted with heptane (65 mL), MTBE (17.5 mL), and H$_2$O (50 mL). The organic phase was separated and washed with H$_2$O (50 mL). The aqueous phase was combined and extracted with MTBE/heptane (1:2, 50 mL). The combined organics were washed with brine and dried over MgSO$_4$. Concentration under reduced pressure gave a pale solid which was washed with 10%6 EtOAc in hexane (100 mL) to give 10 g of a white solid (Compound 5, 60% yield, 99% ee). The % ee was measured by HPLC using a chiral column (Regiscell 25 cm×4.6 mm, 5 micron spherical) with 30% iPrOH in hexanes as eluent.

Step f:
4-(3-Methoxycarbonyl-phenyl)-2-oxo-piperidine-1-carboxylic acid tert-butyl ester (40 g, 120 mmol) was dissolved in anhydrous THF (120 mL) and the solution was cooled to −78° C. LiHMDS in THF (1M, 122 mL, 122 mmol) was added dropwise and the resulting mixture was stirred at −78° C. for 3 hours before MeI (33.84 g, 240 mmol) was added dropwise at the same temperature. The mixture was slowly warmed to room temperature overnight. Water (100 mL) was added and the organic layer was separated and washed with brine and dried. Concentration under reduced pressure gave a brown solid which was recrystallized with 10% EtOAc in hexane (400 mL) to give the product (35 g, 84%) as a pale solid.

Step g:
4-(3-Methoxycarbonyl-phenyl)-3-methyl-2-oxo-piperidine-1-carboxylic acid tert-butyl ester (10.4 g, 30 mmol) was added portionwise to HCl in dioxane (4M, 20 mL, 80 mmol). The resulting mixture was stirred at room temperature for two hours before it was concentrated under reduced pressure to give a white solid.

Step h:
The product from step g was dissolved in 30 mL of anhydrous THF. The resulting solution was cooled to −78° C. and a solution of BH$_3$.SMe$_2$ in THF (2M, 45 mL, 90 mmol) was added dropwise. After addition, the mixture was stirred at room temperature for 48 hours before it was cooled to −78° C. MeOH (10 mL) was cautiously added to quench the reaction. Concentrated HCl (8 mL) was added and the mixture was stirred at 60° C. for two hours. MeOH was removed under reduced pressure and the residue was diluted with water (20 mL). The resulting aqueous mixture was extracted with MTBE:heptane (1:2, 50 mL). The separated aqueous layer was adjusted to pH 9 by adding NH$_4$OH aqueous solution followed by extraction with iPrOH:CHCl$_3$ (1:2, 3×100 mL). The combined organic was washed with brine and dried over MgSO$_4$ before it was concentrated under reduced pressure. The residue was purified by silica gel chromatography (10% MeOH in CH$_2$Cl$_2$, plus 1% NH$_4$OH) to give the desired product as a colorless oil.

Synthesis of 2-(aminomethyl)-4,6-bis(trifluoromethyl)phenol

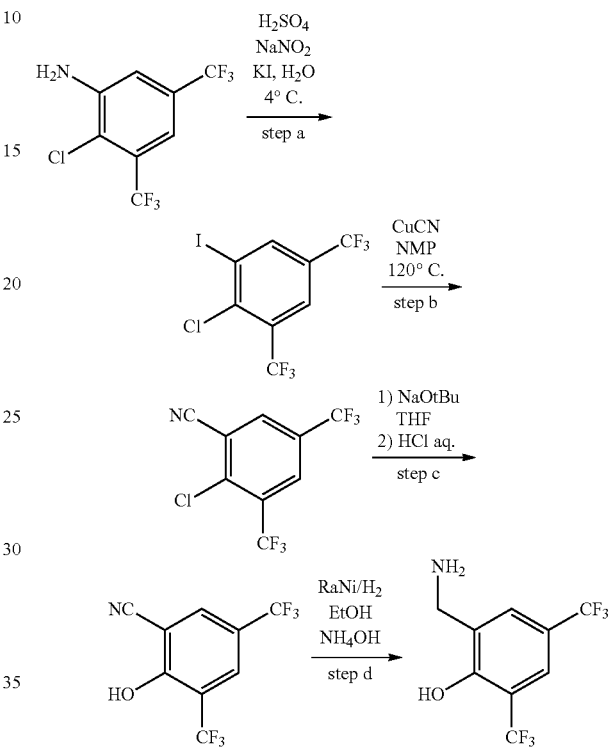

Step a:
A mixture of H2O (30 mL) and H2SO$_4$ (30 mL) was cooled in an ice bath, 2-Chloro-3,5-bis-trifluoromethyl aniline (5.00 g, 19.0 mmol, 1 equiv) was added in MeCN (30 mL) over 5 min. This was stirred for 10 min then NaNO$_2$ (2.36 g, 34.2 mmol, 1.8 equiv) in H2O (17 mL) was added dropwise over 5 min, during which the internal temperature reached 10° C. This was stirred 10 min, then poured into an ice cooled solution of KI (11.0 g, 66.5 mmol, 3.5 equiv) in H$_2$O (30 mL). This was stirred for 2 h then diluted with CHCl$_3$ (60 mL). The layers were separated and the aqueous was extracted with CHCl$_3$. The combined organic was washed with saturated aqueous NaHCO$_3$ (2×) then saturated aqueous Na$_2$S$_2$O$_3$. The organic was then dried over MgSO$_4$, filtered and concentrated to give the product (6.58 g, 93%) as a light brown oil.

Step b:
2-Chloro-1-iodo-3,5-bis-trifluoromethyl-benzene (11.8 g, 31.5 mmol, 1 equiv) was dissolved in N-methylpyrrolidone (32 mL) and CuCN (3.4 g, 38.2 mmol, 1.2 equiv) was added. The reaction was heated to 120° C. for 6 h. The reaction was allowed to cool to room temperature, then diluted with H$_2$O (100 mL) and heptane (100 mL). This was then filtered through celite and the layers were separated. The organic layer was filtered through silica gel (10 g) using heptane (50 mL) to elute. The solution was then concentrated to give the product (6.6 g, 76%).

Step c:

2-Chloro-3,5-bis-trifluoromethyl-benzonitrile (57.1 g, 209 mmol, 1 equiv) was dissolved in THF (417 mL) and cooled in an ice bath. NaOtBu (24.0 g, 250 mmol, 1.2 equiv) was added portionwise over 10 min, keeping the internal temperature below 8° C. After 30 min the reaction was allowed to warm to room temperature, then stirred for 3 h. Aqueous HCl (4N, 627 mL, 2.51 mol, 12 equiv) was added and this was stirred at room temperature overnight. The reaction was then heated to 50° C. for 2 h. The solution was concentrated, then heptane (400 mL) was added. The layers were separated and the organic was dried over MgSO$_4$, filtered and concentrated. The resulting oil was diluted with heptane to a total weight of 160 g, then cooled to −20° C. This was filtered and the solid was washed with cold heptane (60 mL) to give the product (23.6 g, 44%).

Step d:

2-Hydroxy-3,5-bis-trifluoromethyl-benzonitrile (2.79 g, 10.9 mmol) was dissolved in EtOH (50 mL) and NH$_4$OH (5 ml). Raney nickel slurry in water (2.00 mL) was added and the reaction was shaken under H$_2$ (40 psi) for 3 days. The reaction was filtered, the filter cake was rinsed with MeOH, and the combined solution was then concentrated. The resulting residue was taken up in MeOH and HCl in Et$_2$O (2M, 6 mL, 12 mmol) was added. The mixture was concentrated, then taken up in EtOAc. This was washed with NH$_4$OH then concentrated. The resulting solid was triturated with Et$_2$O to give 2-aminomethyl-4,6-bis-trifluoromethyl-phenol (1.55 g, 55%).

Example 26

Synthesis of 3-[(3R,4S)-1-[(3R,6S)-[6,8-bis(trifluoromethyl)-2,4-dihydro-1,3-benzoxazine-3-carbonyl]-6-cyclopropyl-tetrahydropyran-3-yl]-3-methyl-4-piperidyl]benzoic acid

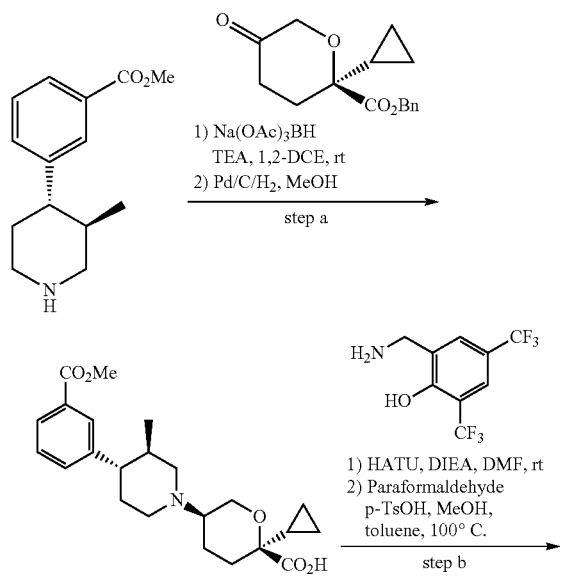

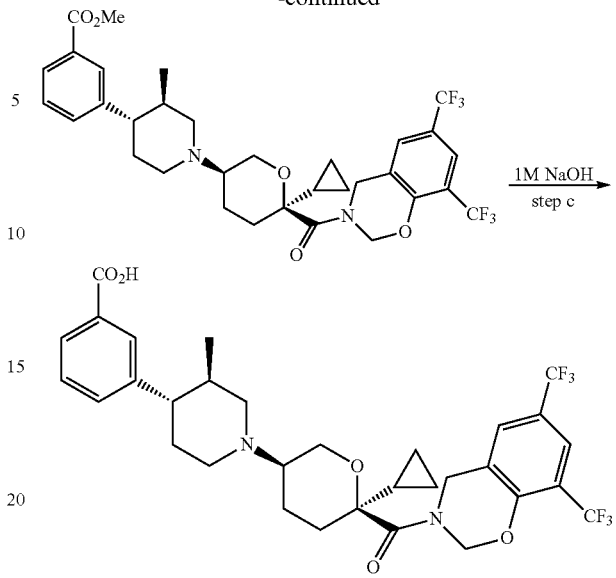

Step a:

To a mixture of 3-[(3R,4S)-3-methyl-4-piperidyl]benzoate (4.5 g, 19.3 mmol), benzyl (2S)-2-cyclopropyl-5-oxo-tetrahydropyran-2-carboxylate (5.8 mmol, 21.2 mmol) and triethylamine (5.4 mL) in anhydrous 1,2-dichloroethane (100 mL), Na(OAc)$_3$BH (8.2 g, 38.6 mmol) was added. The reaction mixture was stirred at rt overnight, then diluted with H$_2$O (100 mL) and the organic layer was separated. The aqueous layer was extracted with CH$_2$Cl$_2$ (50 mL), and the combined organics were dried over MgSO$_4$, filtered and evaporated. The residue was dissolved in MeOH (100 mL) and 10% Pd/C (50% wet) (2.1 g, 1.0 mmol) was added under N$_2$. The reaction mixture was vigorously shaken in a Parr shaker apparatus at 55 psi H$_2$ overnight, then filtered through celite and evaporated. The residue was diluted with acetone (45 mL) and the product was filtered off, washed with acetone (5 mL) and Et$_2$O (15 mL) and dried under vacuum (2.4 g, 31%).

Step b:

To the mixture of the acid from Step a (2.2 g, 5.5 mmol), HATU (2.2 g, 5.8 mmol) in anhydrous DMF (30 mL), diisopropylethylamine (1.9 mL, 11.0 mmol) was added. The mixture was stirred at rt for 15 min, then 2-(aminomethyl)-4,6-bis(trifluoromethyl)phenol (1.5 g, 5.8 mmol) in anhydrous DMF (10 mL) was added. The reaction was stirred at rt overnight, then diluted with H$_2$O (300 mL) and extracted with EtOAc (3×100 mL). The combined organics were washed with brine (4×50 mL) then dried over MgSO$_4$, filtered and evaporated. The residue was dissolved in toluene (300 mL) and paraformaldehyde (20 g), p-TsOH.H$_2$O (2.1 g, 1 mmol) and MsOH (0.7 mL, 11 mmol) were added. The reaction was stirred at reflux (Dean Stark apparatus) for 5 h, then cooled to rt, diluted with saturated NaHCO$_3$ (200 mL) and extracted with EtOAc (2×100 mL). The combined organics were dried over MgSO$_4$, filtered and evaporated. The crude ester was purified by column chromatography (silica gel, hexanes→1:1 hexanes:EtOAc) to give a white solid (2.5 g, 70%). MS: (ES) m/z calculated for C$_{33}$H$_{37}$F$_6$N$_2$O$_5$ [M+H]$^+$ 655.3, found 655.5.

Step c:

The product from Step b (2.5 g, 3.8 mmol) was diluted with 1M NaOH (40 mL, 95:5; MeOH:H$_2$O) and stirred at 40° C. for 5 h. AcOH (2.3 mL, 40 mmol) was added and the mixture was evaporated. The residue was diluted with H₂O (200 mL) and extracted using CH₂Cl₂ (2×100 mL). The combined organics were dried over MgSO₄, filtered and 2M HCl in Et₂O (5.7 mL, 11.4 mmol) was added. The mixture was evaporated and the residue was washed with Et₂O (50 mL) to give a yellowish solid that was the product as the HCl salt (2.15 g, 83%). $^1$H NMR (400 MHz, CD₃OD) δ 7.97-7.83 (m, 3H), 7.81-7.73 (m, 1H), 7.51-7.41 (m, 2H), 6.21-5.89 (m, 2H), 5.19-4.92 (m, 2H), 4.45-4.32 (m, 1H), 3.71-3.52 (m, 3H), 3.48-3.35 (m, 1H), 3.24-3.09 (m, 1H), 2.85 (t, J=12.0 Hz, 1H), 2.71-2.60 (m, 1H), 2.60-2.48 (m, 1H), 2.37-2.24 (m, 1H), 2.23-2.08 (m, 1H), 2.08-1.94 (m, 2H), 1.89-1.70 (m, 1H), 1.70-1.55 (m, 1H), 1.24-1.13 (m, 1H), 0.75 (d, J=6.6 Hz, 3H), 0.72-0.28 (m, 4H). MS: (ES) m/z calculated for C₃₂H₃₅F₆N₂O₅ [M+H]⁺ 641.2, found 641.5.

Example 27

Synthesis of 5-[(2S)-4-[(3R,6S)-6-[[3-chloro-5-(trifluoromethyl)phenyl]methylcarbamoyl]-6-cyclopropyl-tetrahydropyran-3-yl]-2-methyl-piperazin-1-yl]-2-fluoro-benzoic acid mmol) and DMF (0.5 mL) at ambient temperature. After addition of iPr₂NEt (25 μL, 0.144 mmol), the reaction was stirred for 1 minute before 3-chloro-5-trifluoromethylbenzylamine (18 μL, 0.116 mmol) was added. The reaction mixture was stirred overnight. The reaction was diluted with ethyl acetate (20 mL) and water (10 mL). The layers were separated and the aqueous phase was extracted with ethyl acetate (2×20 mL). After drying with anhydrous sodium sulfate, the crude reaction mixture was concentrated under reduced pressure. The product was purified using flash silica gel chromatography using a gradient of 15% to 33% ethyl acetate in hexanes. Methyl 5-[(2S)-4-[(3R,6S)-6-[[3-chloro-5-(trifluoromethyl)phenyl]methylcarbamoyl]-6-cyclopropyl-tetrahydropyran-3-yl]-2-methyl-piperazin-1-yl]-2-fluoro-benzoate was obtained in 59% yield (34.2 mg).

Step b:
Methyl 5-[(2S)-4-[(3R,6S)-6-[[3-chloro-5-(trifluoromethyl)phenyl]methylcarbamoyl]-6-cyclopropyl-tetrahydropyran-3-yl]-2-methyl-piperazin-1-yl]-2-fluoro-benzoate (34.2 mg, 0.0559 mmol) was dissolved in THF (0.25 mL) at ambient temperature. 1.5 N-lithium hydroxide solution (60 μL, 0.090 mmol) was added followed by methanol (60 μL).

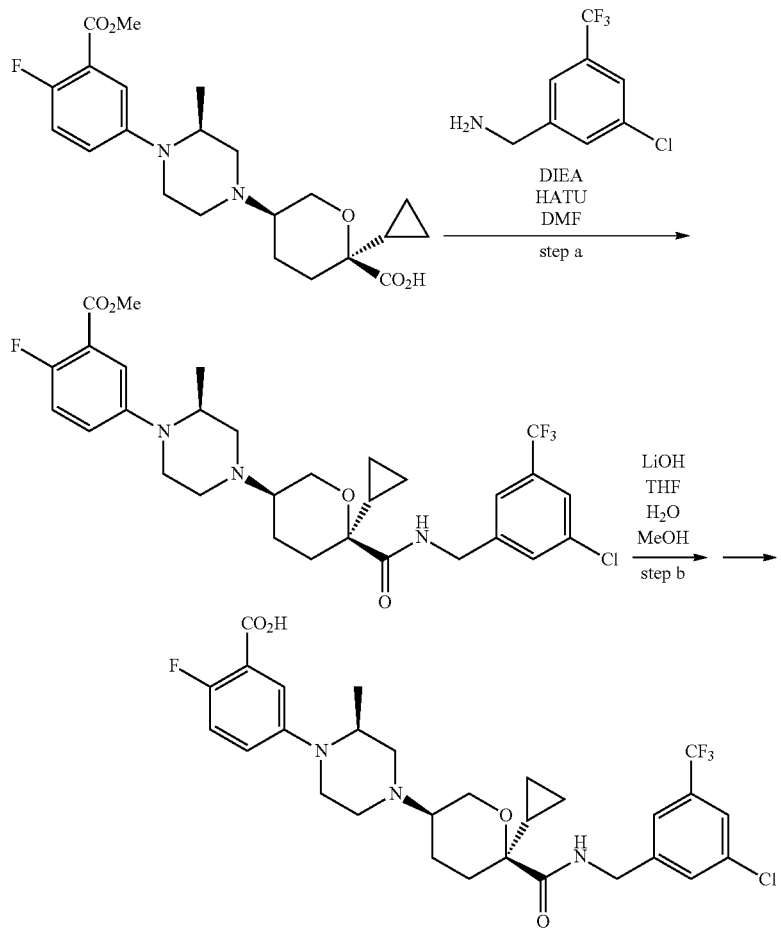

Step a:
In a 20 mL vial, (2S,5R)-2-cyclopropyl-5-[(3S)-4-(4-fluoro-3-methoxycarbonyl-phenyl)-3-methyl-piperazin-1-yl]tetrahydropyran-2-carboxylic acid (39.7 mg, 0.094 mmol) was added followed by HATU (38.2 mg, 0.100

The reaction mixture was stirred overnight. The crude product was purified using reverse phase HPLC using a gradient of acetonitrile in water with 0.01% trifluoromethylacetic acid (20%-95%). Upon removal of the solvent, 5-[(2S)-4-[(3R,6S)-6-[[3-chloro-5-(trifluoromethyl)phenyl]

methylcarbamoyl]-6-cyclopropyl-tetrahydropyran-3-yl]-2-methyl-piperazin-1-yl]-2-fluoro-benzoic acid was obtained as a bis TFA salt (39.0 mg, 84% yield). $^1$H NMR (400 MHz, Methanol-$d_4$) δ 8.85 (t, J=6.3 Hz, 1H), 7.71 (br, 1H), 7.63 (d, J=16 Hz, 1H), 7.61 (s, 1H), 7.40 (br, 1H), 7.22-7.17 (m, 1H), 4.84-4.90 (m, 1H), 4.70 (dd, J=15.5, 7.1 Hz, 1H), 4.32 (dd, J=15.6, 5.3 Hz 1H), 4.24 (d, J=11.3 Hz, 1H), 3.62 (t, J=10.8 Hz, 1H), 3.00-3.62 (m, 8H), 2.74-2.58 (m, 1H), 2.32-2.27 (m, 1H), 1.79-1.52 (m, 2H), 1.22-1.06 (m, 1H), 0.99 (br, 3H), 0.71 (dt, J=9.5, 4.6 Hz, 1H), 0.55 (dt, J=9.8, 5.4 Hz, 1H), 0.47 (ddq, J=13.9, 9.0, 4.4 Hz, 1H). MS: (ES) m/z calculated for $C_{29}H_{33}ClF_4N_3O_4$ [M+H]$^+$ 598.2, found 598.1.

Example 28

Synthesis of (3S,4R)-1-[(3R,6S)-6-cyclopropyl-6-[8-ethoxy-6-(trifluoromethyl)-2,4-dihydro-1,3-benzoxazine-3-carbonyl]tetrahydropyran-3-yl]-4-(4-fluorophenyl)piperidine-3-carboxylic acid

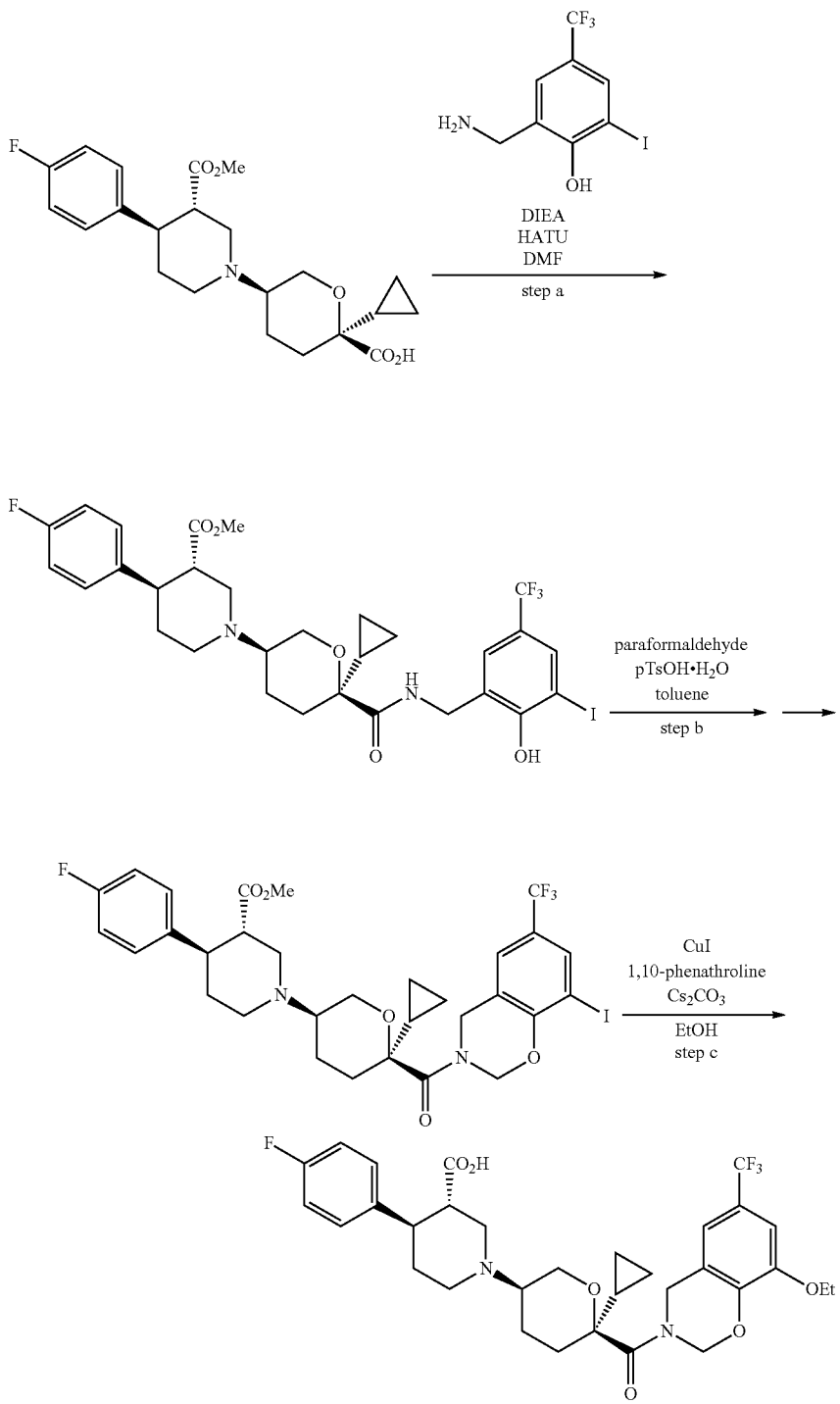

Step a:

A 20 mL vial was charged with (2S,5R)-2-cyclopropyl-5-[(3S,4R)-4-(4-fluorophenyl)-3-methoxycarbonyl-1-piperidyl]tetrahydropyran-2-carboxylic acid (360 mg, 0.887 mmol), HATU (356 mg, 0.936 mmol) and DMF (3.5 mL) at ambient temperature. iPr$_2$NEt (234 µL, 1.34 mL) was added and the reaction mixture was stirred for 15 minutes. Part of reaction mixture (1.56 mL) was removed for use in a different reaction. To the remaining reaction mixture was added 2-hydroxy-3-iodo-5-trifluoromethylbenzylamine (188 mg, 0.593 mmol) and the reaction was stirred for 5 hours. Additional 2-hydroxy-3-iodo-5-trifluoromethylbenzylamine (34.1 mg, 0.108 mmol) was added to drive the reaction to completion. When all starting material was consumed, the reaction was diluted with water (10 mL) and ethyl acetate (25 mL). The layers were separated and the aqueous layer was extracted with ethyl acetate (2×20 mL). The combined organic layer was dried over anhydrous sodium sulfate followed by removal of solvent under reduced pressure. The obtained crude product was used directly in the next step.

Step b:

Crude product from step a (0.5 mmol) was dissolved in toluene (5 mL). p-Toluene sulfonic acid monohydrate (195 mg, 1.03 mmol) was added followed by paraformaldehyde (~170 mg, 5.71 mmol). The reaction mixture was stirred at 100° C. The sublimed paraformaldehyde was scraped off from the wall into the reaction mixture, at the same time, more paraformaldehyde (one scoop every 10 to 20 minutes) was added. This process was continued while heating at 100° C. until the reaction conversion reached more than 60% (about 5 hours). The reaction mixture was cooled and diluted with ethyl acetate (20 mL) and saturated aqueous sodium bicarbonate (10 mL). The organic layer was separated and extracted with ethyl acetate (2×20 mL). The combined organic layer was dried over anhydrous sodium sulfate. After removal of solvent under reduced pressure, the product was purified using silica gel chromatography. The compound was eluted using a gradient of 17% to 50% ethyl acetate in hexanes. The product was obtained in 69% yield (247 mg).

Step c:

The product from the previous step (97.5 mg, 0.136 mmol) was added to a microwave vessel followed by cesium carbonate (89.5 mg, 0.275 mmol), 1,10-phenanthroline (12.0 mg, 0.0666 mmol), copper (1) iodide (12.9 mg, 0.0677 mmol) and ethanol (1 mL). The reaction mixture was irradiated under microwave for 45 minutes at 100° C. Water (0.1 mL) was added and it was further irradiated for 10 minutes at 100° C. After addition of 1N-NaOH (0.1 mL), the reaction was diluted with dichloromethane followed by filtration of the insoluble material. The filtrate was concentrated and purified using preparatice TLC using 17% methanol in ethyl acetate as the eluent. The obtained product was further purified using reverse phase HPLC to afford (3S,4R)-1-[(3R,6S)-6-cyclopropyl-6-[8-ethoxy-6-(trifluoromethyl)-2,4-dihydro-1,3-benzoxazine-3-carbonyl]tetrahydropyran-3-yl]-4-(4-fluorophenyl)piperidine-3-carboxylic acid (13.0 mg, 16% yield) as a TFA salt. $^1$H NMR (400 MHz, Methanol-d$_4$) δ 7.23-7.28 (m, 2H), 7.02-7.15 (m, 4H), 6.24-6.21 (m, 1H), 5.63-5.59 (m, 1H), 4.94-4.89 (m, 1H), 4.43-4.35 (m, 1H), 4.10 (q, J=7.0 Hz, 2H), 3.73-3.78 (m, 1H), 3.62-3.67 (m, 1H), 3.53-3.60 (m, 1H), 3.46-3.49 (m, 1H), 3.12-3.37 (m, 3H), 3.04-3.10 (m, 1H), 2.92-2.99 (m, 1H), 2.67-2.61 (m, 1H), 2.30-2.24 (m, 1H), 2.11-2.04 (m, 1H), 1.90-1.97 (m, 1H), 1.69-1.79 (m, 1H), 1.56-1.65 (m, 1H), 1.42 (t, J=7.0 Hz, 3H), 1.20-1.26 (m, 1H), 0.59-0.70 (m, 3H), 0.44-0.49 (m, 1H). MS: (ES) m/z calculated for C$_{32}$H$_{37}$F$_4$N$_2$O$_6$ [M+H]$^+$ 621.3, found 621.4.

Example 29

Synthesis of 5-[(3R,4S)-1-[(3R,6S)-6-[6,8-bis(trifluoromethyl)-2,4-dihydro-1,3-benzoxazine-3-carbonyl]6-cyclopropyl-tetrahydropyran-3-yl]-3-methyl-4-piperidyl]-2-fluorobenzoic acid

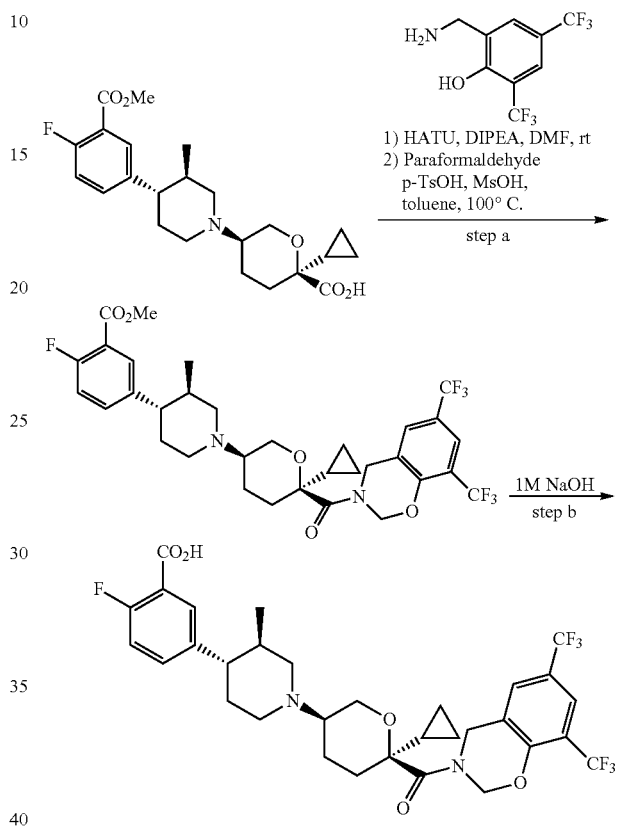

Step a:

To a mixture of the acid (2.2 g, 5.5 mmol) and HATU (2.2 g, 5.8 mmol) in anhydrous DMF (30 mL), diisopropylethylamine (1.9 mL, 11.0 mmol) was added. The mixture was stirred at rt for 15 min, then 2-(aminomethyl)-4,6-bis(trifluoromethyl)phenol (1.5 g, 5.8 mmol) in anhydrous DMF (10 mL) was added. The reaction was stirred at rt overnight, then diluted with H$_2$O (300 mL) and extracted with EtOAc (3×100 mL). The combined organics were washed with brine (4×50 mL) then dried over MgSO$_4$, filtered and evaporated. The residue was dissolved in toluene (300 mL) and paraformaldehyde (20 g), p-TsOH×H$_2$O (2.1 g, 11 mmol) and MsOH (0.7 mL, 11 mmol) were added. The reaction was stirred at reflux (Dean Stark apparatus) for 5 h, then cooled to rt, diluted with saturated NaHCO$_3$ (200 mL) and extracted with EtOAc (2×100 mL). The combined organics were dried over MgSO$_4$, filtered and evaporated. The crude ester was purified by column chromatography (silica gel, hexanes→1:1 hexanes:EtOAc) to give a white solid (2.5 g, 70%).

Step b:

The product from Step a (2.5 g, 3.8 mmol) was diluted with 1N NaOH (40 mL, 95:5; MeOH:H$_2$O) and stirred at 40° C. for 5 h. AcOH (2.3 mL, 40 mmol) was added and the mixture was evaporated. The residue was diluted with H$_2$O (200 mL) and extracted using CH$_2$Cl$_2$ (2×100 mL). The combined organics were dried over MgSO$_4$, filtered and 2M HCl in Et$_2$O (5.7 mL, 11.4 mmol) was added. The mixture was evaporated and the residue was washed with Et$_2$O (50 mL) to give the HCl salt of the product as a yellowish solid (2.15 g, 83%). $^1$H NMR (400 MHz, CD$_3$OD) δ 7.97-7.83 (m, 2H), 7.79-7.70 (m, 1H), 7.51-7.41 (m, 2H), 6.21-5.81 (m, 2H), 5.19-4.92 (m, 2H), 4.45-4.32 (m, 1H), 3.71-3.52 (m, 3H), 3.48-3.35 (m, 1H), 3.24-3.09 (m, 1H), 2.85 (t, J=12.0 Hz, 1H), 2.71-2.60 (m, 1H), 2.60-2.48 (m, 1H), 2.37-2.24 (m, 1H), 2.23-2.08 (m, 1H), 2.08-1.94 (m, 2H), 1.89-1.70 (m, 1H), 1.70-1.55 (m, 1H), 1.24-1.13 (m, 1H), 0.75 (d, J=6.6 Hz, 3H), 0.72-0.28 (m, 4H). MS: (ES) m/z calculated for C$_{32}$H$_{34}$F$_7$N$_2$O$_5$ [M+H]$^+$ 659.2, Found 658.7.

Biological Examples

In Vitro Assays
Reagents

THP-1 cells were obtained from the American Type Culture Collection (Manassas, Va.) and cultured in RPMI tissue culture medium supplemented with 10% fetal calf serum (FCS) in a humidified 5% CO$_2$ incubator at 37° C. Recombinant human chemokine proteins MCP-1 were obtained from R&D Systems (Minneapolis, Minn.). $^{125}$I-labeled MCP-1 protein was obtained from Amersham (Piscataway, N.J.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Ligand Binding Assay

Ligand binding assay can be used to determine the ability of potential CCR2 antagonists to block the interaction between CCR2 and its ligand MCP-1. CCR2 expressing THP-1 cells are centrifuged and resuspended in assay buffer (20 mM HEPES pH 7.1, 140 mM NaCl, 1 mM CaCl2, 5 mM MgCl2, and with 0.2% bovine serum albumin) to a concentration of 2.2×105 cells/mL. Binding assays are set up as follows. First, 0.09 mL of cells (1×105 THP-1 cells/well) was added to the assay plates containing the compounds, giving a final concentration of ~2-10 uM each compound for screening (or part of a dose response for compound IC50 determinations). Then 0.09 mL of 125I labeled MCP-1 (obtained from Amersham; Piscataway, N.J.) diluted in assay buffer to a final concentration of ~50 pM, yielding ~30,000 cpm per well, is added, the plates sealed and incubated for approximately 3 hours at 4° C. on a shaker platform. Reactions are aspirated onto GF/B glass filters pre-soaked in 0.3% polyethyleneimine (PEI) solution, on a vacuum cell harvester (Packard Instruments; Meriden, Conn.). Scintillation fluid (50 uL; Microscint 20, Packard Instruments) is added to each well, the plates are sealed and radioactivity measured in a Top Count scintillation counter (Packard Instruments). Control wells containing either diluent only (for total counts) or excess MCP-1 (1 ug/mL, for non-specific binding) are used to calculate the percent of total inhibition for compound. The computer program Prism from GraphPad, Inc. (San Diego, Ca) is used to calculate IC50 values. IC50 values are those concentrations required to reduce the binding of labeled MCP-1 to the receptor by 50%.

Calcium Flux Assay

Calcium flux assay measures an increase in intracellular calcium following ligand-induced receptor activation and may be employed as a secondary assay following primary screening. Such an assay may be carried out, for instance, on a FLIPR machine (Molecular Devices, Mountain View, Calif.). To begin an assay, chemokine expressing cells (such as THP-1 cells for CCR2 assay) are harvested by centrifugation of cell suspension, and resuspended to 1.5×10$^6$ cells/mL in HBSS (with 1% fetal calf serum). Cells are then labeled with a calcium indicator dye Fluo-4 AM for 45 minutes at 37° C. with gentle shaking. Following incubation, cells are pelleted, washed once with HBSS and resuspended in the same buffer at a density of 1.6×10$^6$ cells/mL. One hundred microliters of labeled cells are mixed with 10 uL of test compound at the appropriate concentrations on an assay plate. Chemokine protein (MCP-1 at a final concentration of 0.1 nM for CCR2 assay) is added to activate the receptor. The degree of inhibition is determined by comparing calcium signals between compound-treated and untreated cells. IC50 calculations are further performed by non-linear squares regression analysis using Graphpad Prism (Graphpad Software, San Diego, Calif.).

Conventional Migration Assay

Conventional migration assay was used to determine the efficacy of potential receptor antagonists in blocking migration mediated through chemokines (such as CCR2). This assay was routinely performed using the ChemoTX® microchamber system with a 5-μm pore-sized polycarbonate membrane. To begin such an assay, chemokine expressing cells (such as THP-1 cells for CCR2 assay) were harvested by centrifugation of cell suspension at 1000 RPM on a GS-6R Beckman centrifuge. The cell pellet was resuspended in chemotaxis buffer (HBSS with 0.1% BSA) at 10×10$^6$ cells/mL for the CCR2 assay. Test compounds at desired concentrations were prepared from 10 mM stock solutions by serial dilutions in chemotaxis buffer. An equal volume of cells and compounds were mixed and incubated at room temperature for 15 minutes. Afterwards, 20 μL of the mixture was transferred onto the porous membrane of a migration microchamber, with 29 μL of chemokine ligand (0.1 nM chemokine MCP-1 protein for CCR2 assay) placed at the lower chamber. Following an incubation at 37° C. (90-minute for CCR2), during which cells migrated against the chemokine gradient, the assay was terminated by removing the cell drops from atop the filter. To quantify cells migrated across the membrane, 5 μL of 7× CyQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. IC$_{50}$ calculation was further performed by non-linear squares regression analysis using Graphpad Prism (Graphpad Software, San Diego, Calif.).

In Vivo Efficacy

Evaluation of Compounds in a Rat Model of Collagen-Induced Arthritis

A 17-day study of type II collagen-induced arthritis can be conducted to evaluate the effects of compounds of the invention on arthritis-induced clinical ankle swelling. Rat collagen-induced arthritis is an experimental model of polyarthritis that has been widely used for preclinical testing of numerous anti-arthritic agents (see Trentham et al., J. Exp. Med. 146(3):857-868 (1977), Bendele et al., Toxicologic Pathol. 27:134-142 (1999), Bendele et al., Arthritis Rheum. 42:498-506 (1999)). The hallmarks of this model are reliable onset and progression of robust, easily measurable polyarticular inflammation, marked cartilage destruction in association with pannus formation and mild to moderate bone resorption and periosteal bone proliferation. Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17-day study. Compound is dosed daily by sub-cutaneous injection from day 9 to day 17 at a dose of, for instance, 100 mg/kg and a volume of 1 mL/kg in an appropriate vehicle. Caliper measurements of the ankle joint diameter are taken daily, and reducing joint swelling is taken as a measure of efficacy.

Evaluation of Compounds in Animal Models of Human Ulcerative Colitis

A murine model described by Panwala and coworkers (Panwala, et al., J Immunol., 161(10):5733-44 (1998)) involves genetic deletion of the murine multi-drug resistant gene (MDR). MDR knockout mice (MDR−/−) are susceptible to developing a severe, spontaneous intestinal inflammation when maintained under specific pathogen-free facility conditions. The intestinal inflammation seen in MDR−/− mice has a pathology similar to that of human inflammatory bowel disease (IBD) and is defined by Th1 type T cells infiltration into the lamina propria of the large intestine.

Another murine model for IBD has been described by Powrie et al., Int Immunol., 5(11): 1461-71 (1993), in which a subset of CD4+ T cells (called CD45RB(high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

Evaluation of Compounds in Animal Models of Human Crohn's Disease

The TNF ARE(−/−) model. The role of TNF in Crohn's disease in human has been demonstrated more recently by success of treatment using anti-TNF alpha antibody by Targan et al., N Engl J Med., 337(15): 1029-35 (1997). Mice with aberrant production of TNF-alpha due to genetic alteration in the TNF gene (ARE−/−) develop Crohn's-like inflammatory bowel diseases (see Kontoyiannis et al., Immunity, 10(3):387-98 (1999)).

The SAMP/yit model. This model is described by Kosiewicz et al., J Clin Invest., 107(6):695-702 (2001). The mouse strain. SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Evaluation of Compounds in a Mouse Model of Thioglycollate-Induced Peritoneal Inflammation A 2-day study of thioglycollate-induced inflammation was conducted to evaluate the effects of the test compound, Compound 53 (FIG. 1). The hallmarks of this model are reliable onset and progression of robust, easily measurable inflammatory cellular infiltrate. For the induction of inflammatory peritonitis in Lewis rats, Brewer-Thioglycollate (1.0 mL, 4% solution in distilled water) was injected intra peritoneal (i.p.). Before this injection, the treatment group received test compound, 4-chloro-3-trifluoromethyl-N-[5-chloro-2-(2-methanesulfonyl-benzoyl)-pyridin-3-yl]-benzenesulfonamide, or vehicle and the control group received the same volume of PBS as i.p. injection. After 2 days, a peritoneal lavage was performed with ice-cold PBS containing 1 mM EDTA. The recovered cells were counted with a cell counter (Coulter Counter; Coulter Pharmaceutical, Palo Alto, Calif.) and monocytes/macrophages were identified by flow cytometry using light-scatter properties.

The test compound significantly and specifically inhibited the number of inflammatory macrophages elicited following thioglycollate injection.

Evaluation of Compounds in a Mouse Model of Bacterial Infection

A 1-day study of *Streptococcus pneumoniae* infection can be conducted to evaluate the effects of the test compound. The model measures bacterial infection and spread in an animal following pulmonary infection with live bacterial cultures, measured by inflammatory cellular infiltrate, and assessment of bacterial burden. C57/B6 mice are inoculated intra nasally with LD50 400 CFU at day 0. Groups are either compound or vehicle control treated 1 day prior to bacterial inoculation and twice daily throughout the study. Bacterial burden is measured at 24 hours by plating serial dilutions of homogenized lung tissue on agar plates and counting colonies.

Evaluation of Compounds in a Mouse Model of Lung Carcinoma

Many tumor models in animals are known in the art, and may be employed to evaluate a compound of instance. For instance, in a lung carcinoma xenograft study, A549 tumor fragments (30-40 mg) are implanted into the sub cutaneous space in nude mice. Tumors are permitted to grow until approximately 150 mg in size (between 100 and 200 mg) at which point mice are enrolled in the study and treatment begins. Mice are treated with a compound of interest or the vehicle control. Melphalan may be included as a positive control (9 mpk/dose, ip administration, Q4Dx3). Tumors are measured twice weekly with a caliper in two dimensions and converted to tumor mass using the formula for a prolate ellipsoid (a x b2/2), where a is the longer dimension and b is the shorter dimension, and assuming unit density (1 mm3=1 mg). Body weights may also be measured twice weekly to assess any adverse effects of compound dosing. Antitumor activity is assessed by the delay in tumor growth of the treated group in comparison to the vehicle-treated control group.

Evaluation of Compounds in a Mouse Model of Glioblastoma

Many tumor models in animals are known in the art, and may be employed to evaluate a compound of instance. For instance, in a murine glioblastoma model, 1×106 U251MG cells are implanted by stereotactic injection into the into the brains of nude mice. After 20 days tumors are irradiated with between 1-15 Gy of radiation. Following irradiation mice are treated (eg via subcutaneous, intraperitoneal, oral, parenteral or other route) with compound or vehicle control and tumors are allowed to progress. Tumor growth and/or mortality are monitored for the remainder of the study. Tumors are measured twice weekly with a caliper in two dimensions and converted to tumor mass using the formula for a prolate ellipsoid (a x b2/2), where a is the longer dimension and b is the shorter dimension, and assuming unit density (1 mm3=1 mg). Body weights may also be measured twice weekly to assess any adverse effects of compound dosing. Antitumor activity is assessed by the delay in tumor growth of the treated group in comparison to the vehicle-treated control group.

Evaluation of Compounds in a Mouse Model of Pancreatic Cancer

Many tumor models in animals are known in the art, and may be employed to evaluate a compound of instance. For instance, in a murine pancreatic cancer model, panco2 cells (NCI) were implanted orthotopically in the pancreas of C57bl/6 mice. Tumors were allowed to progress for three weeks, then animals were treated with either Compound 53

(FIG. 1) or vehicle control by subcutaneous injection once daily for three weeks. Compound efficacy was assessed by analysis of tumor growth. Animals treated with compound Compound 53 (FIG. 1) displayed significantly smaller tumors than vehicle treated animals.

Evaluation of Compounds in a Mouse Model of Polycystic Kidney Disease

In a mouse model of polycystic kidney disease Pkd1flox/flox:Pkhd1-Cre mice (Jackson Labs, ME) these mice spontaneously develop polycystic kidney disease due to a kidneyselective genetic deficiency of the mouse ortholog of the human PKD1 gene, mutations in which are responsible for the most common and most severe form of ADPKD. Disease is allowed to develop, and at day 10 animals are treated with compound o the invention or the vehicle control by subcutaneous injection once daily until day 26. At this time animals are sacrificed and kidney mass, blood urea and kidney cystic counts are performed. Efficacy is measured as an improvement of these measures when treated with compound Compound 53 (FIG. 1).

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A method for treating a mammal suffering from a disease or disorder selected from the group consisting of diabetic nephropathy, nonalcoholic statohepatitis, and pancreatic cancer, comprising administering to the mammal an effective amount of a compound selected from the group consisting of

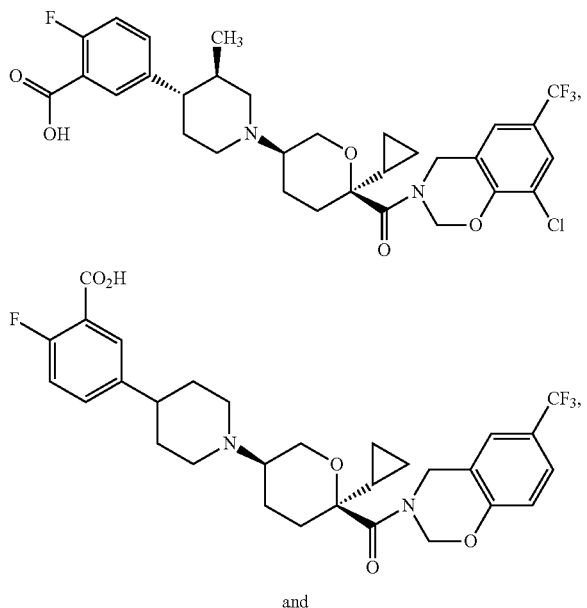

and

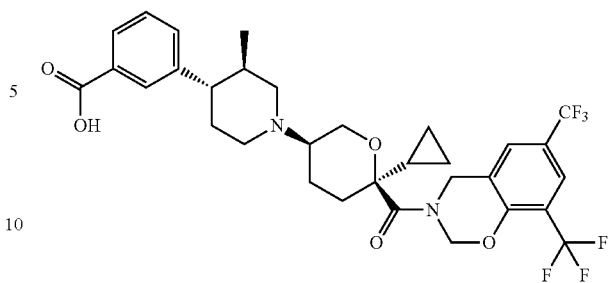

or a pharmaceutically acceptable salt thereof.

2. The method of claim 1, wherein said compound has the formula

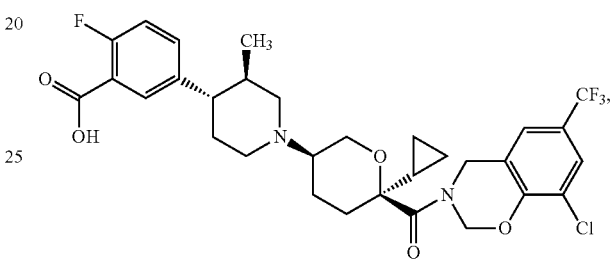

or a pharmaceutically acceptable salt thereof.

3. The method of claim 2, wherein said disease or disorder is diabetic nephropathy.

4. The method of claim 2, wherein said disease or disorder is nonalcoholic statohepatitis.

5. The method of claim 2, wherein said disease or disorder is pancreatic cancer.

6. The method of claim 1, wherein said compound has the formula

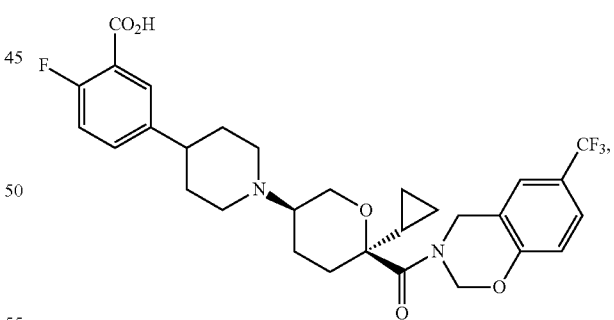

or a pharmaceutically acceptable salt thereof.

7. The method of claim 6, wherein said disease or disorder is diabetic nephropathy.

8. The method of claim 6, wherein said disease or disorder is nonalcoholic statohepatitis.

9. The method of claim 6, wherein said disease or disorder is pancreatic cancer.

10. The method of claim 1, wherein said compound has the formula

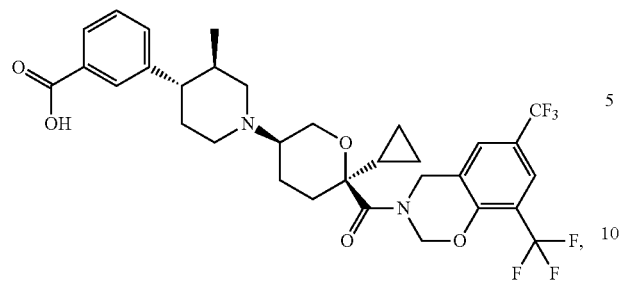
or a pharmaceutically acceptable salt thereof.
11. The method of claim 10, wherein said disease or disorder is diabetic nephropathy.
12. The method of claim 10, wherein said disease or disorder is nonalcoholic statohepatitis.
13. The method of claim 10, wherein said disease or disorder is pancreatic cancer.
* * * * *